(12) United States Patent
Ellwanger et al.

(10) Patent No.: US 11,572,415 B2
(45) Date of Patent: Feb. 7, 2023

(54) MULTIVALENT FV ANTIBODIES

(71) Applicant: Affimed GmbH, Heidelberg (DE)

(72) Inventors: Kristina Ellwanger, Heidelberg (DE); Ivica Fucek, Frankfurt am Main (DE); Thorsten Ross, Edingen-Neckarhausen (DE); Thomas Mueller, Planckstadt (DE); Erich Rajkovic, Schriesheim (DE); Uwe Reusch, Maikammer (DE); Martin Treder, Heidelberg (DE); Michael Weichel, Bischofsheim (DE)

(73) Assignee: AFFIMED GMBH, Heidelberg (DE)

( * ) Notice: Subject to any disclaimer, the term of this patent is extended or adjusted under 35 U.S.C. 154(b) by 817 days.

(21) Appl. No.: 15/950,733

(22) Filed: Apr. 11, 2018

(65) Prior Publication Data

US 2019/0040155 A1 Feb. 7, 2019

Related U.S. Application Data

(63) Continuation-in-part of application No. PCT/EP2016/074642, filed on Oct. 13, 2016.

(30) Foreign Application Priority Data

Oct. 13, 2015 (EP) .................... 15189665

(51) Int. Cl.
| | | |
|---|---|---|
| C07K 16/46 | (2006.01) | |
| C07K 16/28 | (2006.01) | |
| C07K 16/08 | (2006.01) | |
| C07K 16/30 | (2006.01) | |

(52) U.S. Cl.
CPC .......... C07K 16/468 (2013.01); C07K 16/08 (2013.01); C07K 16/2803 (2013.01); C07K 16/283 (2013.01); C07K 16/2878 (2013.01); C07K 16/3076 (2013.01); C07K 2317/31 (2013.01); C07K 2317/35 (2013.01); C07K 2317/56 (2013.01); C07K 2317/62 (2013.01); C07K 2317/622 (2013.01); C07K 2317/626 (2013.01)

(58) Field of Classification Search
None
See application file for complete search history.

(56) References Cited

U.S. PATENT DOCUMENTS

| | | | | |
|---|---|---|---|---|
| 2004/0220388 A1* | 11/2004 | Mertens | ................. | C07K 16/00 530/388.8 |
| 2010/0150927 A1* | 6/2010 | Kimura | ................... | A61P 37/02 435/375 |
| 2012/0237442 A1 | 9/2012 | Rossi et al. | | |
| 2013/0109593 A1* | 5/2013 | Hartmann | ................ | A61P 37/06 435/69.6 |
| 2013/0216476 A1* | 8/2013 | Boumsell | ......... | A61K 39/39558 424/1.49 |
| 2014/0303354 A1* | 10/2014 | Masternak | ........... | C07K 16/468 530/387.3 |
| 2015/0017120 A1* | 1/2015 | Wittrup | ................ | C12N 5/0636 424/85.2 |
| 2017/0037128 A1 | 2/2017 | Little et al. | | |

FOREIGN PATENT DOCUMENTS

| | | | | |
|---|---|---|---|---|
| EP | 1293514 A1 | 3/2003 | | |
| EP | 2 014 680 | 1/2009 | | |
| EP | 2 450 380 | 5/2012 | | |
| WO | WO-9518819 A1 * | 7/1995 | ....... | C07K 14/70575 |
| WO | 97/14719 A1 | 4/1997 | | |
| WO | 03/057829 A2 | 7/2003 | | |
| WO | 2012/088290 A2 | 6/2012 | | |
| WO | 2012/135345 | 10/2012 | | |
| WO | 2014/106015 A2 | 7/2014 | | |
| WO | 2015/158636 A1 | 10/2015 | | |
| WO | 2016/202457 | 12/2016 | | |
| WO | WO-2016202457 A1 * | 12/2016 | ......... | C07K 16/2866 |

OTHER PUBLICATIONS

Singer et al (Ji, 33(6):599-608, 2010).*
Gleason etal (MOT 11(22):2674-2684, 2012).*
Anegon et al (H-2 Antigens, editor David Chella, 1987, pp. 815, abstract only).*
Li et al (Ji, 189(9):4284-4294, 2012).*
Pazina et al (CIR, 7:1633-1646, 2019).*
Kipriyanov, et al. "Bispecific tandem diabody for tumor therapy with improved antigen binding and pharmacokinetics" Journal of Molecular Biology, Oct. 1999, 293(1):41-56.
Kiprijanov, Sergej M., Generation of bispecific and tandem diabodies. Methods in Molecular Biology, vol. 562: Antibody Phage Display, 2nd edition, Methods and Protocals, Humana Press (2009) 177-193.
International Search Report and Written Opinion of the International Searching Authority dated Jan. 18, 2017, which issued during prosecution of International Application No. PCT/EP2016/074642.
Reusch, et al. "A novel tetravalent bispecific TandAb (CD30/CD16A) efficiently recruits NK cells for the lysis of CD30+ tumor cells" MAbs, Mar. 2014, 6(3):727-738.
Roskopf, et al. "T cell-recruiting triplebody 19-3-19 mediates serial lysis of malignant B-lymphoid cells by a single T cell" Oncotarget, Jul. 2014, 5(15):6466-6483.

(Continued)

Primary Examiner — Brad Duffy

(74) Attorney, Agent, or Firm — Duane Morris LLP; Thomas J. Kowalski; Deborah L. Lu

(57) ABSTRACT

The application pertains to a trispecific antibody molecule which may comprise a diabody-unit integrated into a polypeptide chain having at least six variable domains linked one after another. In certain instances two single-chain Fv (scFv) fragments are distally connected to the diabody-unit providing two further antigen binding sites (FIGS. 1 and 2).

25 Claims, 17 Drawing Sheets

(8 of 17 Drawing Sheet(s) Filed in Color)

Specification includes a Sequence Listing.

(56) References Cited

OTHER PUBLICATIONS

Schubert, et al. "A dual-targeting triplebody mediates preferential redirected lysis of antigen double-positive over single-positive leukemic cells" MAbs, Jan. 2014, 6(1):286-296.

Schubert, et al. "A recombinant triplebody with specificity for CD19 and HLA-DR mediates preferential binding to antigen double-positive cells by dual-targeting" MAbs, Jan. 2012, 4(1):45-56.

Schubert, et al. "A single-chain triplebody with specificity for CD19 and CD33 mediates effective lysis of mixed lineage leukemia cells by dual targeting" MAbs, 2011, 3(1):21-30.

English tr nsl ion of Office Action dated Mar. 3. 2021 in co-pending Chinese Application No. 201680073236.5

\* cited by examiner

MULTIVALENT FV ANTIBODIES

RELATED APPLICATIONS AND INCORPORATION BY REFERENCE

This application is a continuation-in-part application of international patent application Serial No. PCT/EP2016/074642 filed 13 Oct. 2016, which published as PCT Publication No. WO 2017/064221 on 20 Apr. 2017, which claims benefit of European patent application Serial No. 15189665.1 filed 13 Oct. 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Apr. 11, 2018, is named 43488002005_SL.txt and is 202,915 bytes in size.

FIELD OF THE INVENTION

The present invention relates to a multivalent and multi-specific Fv-antibody derivative, in particular an Fv antibody molecule which may comprise a diabody-unit.

BACKGROUND OF THE INVENTION

Bispecific antibodies are used to engage two different therapeutic targets or perform two distinct functions. Such antibodies can be used for example to recruit an immune effector cell, e.g. T- or NK-cell, towards a particular target cell. Various antibody-fragment based molecules are known and under investigation, for example in cancer therapy.

Bispecific antibodies can be constructed using only antibody variable domains. For example, the linker sequence between the $V_H$ and $V_L$ domains can be shortened to such an extent that they cannot fold over and associate pairwise in an intramolecular fashion. Such short linkers, e.g. 2-12 residues, prevent said forming of a monomeric single chain variable fragment (scFv) molecule and favor intermolecular $V_H/V_L$ pairings between complementary variable domains of different polypeptide chains forming a dimeric "diabody" (Holliger et al., 1993, Proc. Natl. Acad. Sci. USA 90, 6444-6448). Such a diabody can be used to construct bispecific antibodies, which are obtained by non-covalent association of two single-chain polypeptide fusion products, each consisting of the $V_H$ domain from one antibody connected by a short linker to the $V_L$ domain of another antibody (or vice versa).

WO 03/025018 relates to a bispecific antigen-binding molecule with a structure formed by identical single-chain polypeptides with four binding domains. A $V_H$ and a $V_L$ domain at a terminal part of each polypeptide chain are linked by a short linker and associate intermolecularly with the corresponding $V_H$ and $V_L$ domains of another polypeptide chain, while the other $V_H$ and $V_L$ domains of each polypeptide chain bind intramolecularly to one another within the same chain resulting in an antigen-binding scFv unit. Such constructs are homodimers, i.e. they consist of identical single-chain polypeptides associating with one another in a pairwise fashion.

Further, desired are trispecific antibodies to target two tumor antigens which allow for greater selectivity for cancer cells, sparing healthy tissue and resulting in a wider dose range and therapeutic applicability within which the drug can be effective in eradicating cancer cells. For example, one trispecific antibody can be used for targeting two different tumor antigens and with a third specificity engage T-cells or NK-cells to exert a cytotoxic effect.

WO 2009/007124 relates to a trispecific fusion of single-chain Fv (scFv) designated as "triplebody" and consisting of three scFv fragments in tandem-arrangement having three different specificities (CD123 and CD33 for tumor markers and one for CD16 on NK-cells). The molecule is additionally stabilized by disulfide bonds at the centrally located scFv. Such molecules allow dual-targeting of double positive tumor cells and bind monovalently to CD16 on NK cells.

Citation or identification of any document in this application is not an admission that such document is available as prior art to the present invention.

SUMMARY OF THE INVENTION

The present invention relates to a multivalent Fv antibody which may comprise a diabody-unit consisting of two pairs of variable domains which associate to two antigen binding sites. A "antigen binding site" denotes a Fv antigen binding site of a pair of VH/VL domains, i.e, a VH/VL antigen binding site, or of a single domain antigen binding site. Each pair of variable domains is linked one after another in a polypeptide. The diabody-unit consists of one polypeptide (single chain diabody-unit) or two polypeptides (diabody-unit). At least one pair of variable domains is linked in the polypeptide to another variable domain located N-terminally to this pair of variable domains and to another variable domain C-terminally. Hence, such polypeptide may comprise at least four variable domains linked one after another, wherein two juxtaposed variable domains linked one after another are one pair of variable domains of the diabody-unit and one further variable domain is located N-terminally to the pair of variable domains of the diabody-unit and the other further variable domains is located C-terminally to the pair of variable domains of the diabody-unit. The variable domain linked N-terminally to the pair of variable domains of the diabody unit can be a variable light chain ($V_L$) domain or a variable heavy chain ($V_H$) domain as well as the domain linked C-terminally to the pair of variable domains of the diabody unit can be a variable light chain domain ($V_L$) or a variable heavy chain domain ($V_H$). Such polypeptide is an Fv polypeptide which may comprise at least four variable domains linked one after another, i.e., the N-terminally linked variable domain linked with the pair of variable domains of the diabody-unit which is linked to another variable domain C-terminally. In particular embodiments six, eight or ten variable domains are linked one after another in such Fv polypeptide.

The multivalent Fv antibody is at least tetravalent and may comprise at least four antigen binding sites. Hence, the Fv polypeptide of the Fv antibody which may comprise at least four variable domains, wherein two of the at least four variable domains is a pair of two juxtaposed variable domains of the diabody-unit associating with the other pair of variable domains of the diabody-unit to two (first and second) antigen binding sites has at least a further (third) variable domain at the N-terminus of the Fv polypeptide which associates with a corresponding variable domain to a further (third) antigen binding site and at least a further (fourth) variable domain at the C-terminus of the Fv polypeptide which associates with a corresponding variable domain to a further (fourth) antigen binding site. In certain embodiments the at least four antigen binding sites of the multivalent Fv antibody are formed between two Fv polypeptides and in other embodiments the at least four antigen binding sites are formed by intramolecular folding of a single Fv polypeptide.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 7 shows a hexavalent Fv antigen-binding molecule consisting of a first polypeptide having six variable domains linked one after another from the N-terminus 7 to the C-terminus 8 of the first polypeptide and a second polypeptide having six variable domains linked one after another from the N-terminus 7a to the C-terminus 8a of the second polypeptide. The domain orientation is only an example and other arrangements for each juxtaposed pair of variable domais are possible as indicated in the Figure. The Fv antigen binding molecule may comprise a dimeric diabody unit 10 formed by a first pair of two variable domains of the first polypeptide associated with a second pair of two variable domains in the second polypeptide. Each of the variable domains of the diabody unit 10 is linked to a scFv unit 2 in the first and second polypeptide. In each of the scFv units 2 the variable domains are linked by a long peptide linker 4. Each of the four scFv units 2 is linked by a peptide linker 5 to a variable domain of the diabody unit 10. This first pair of variable domains consists of two variable domains linked by a short peptide linker 3 and the second pair of variable domains of the diabody unit consists of two variable domains linked by a short linker 3a.

DETAILED DESCRIPTION OF THE INVENTION

Figure 1:
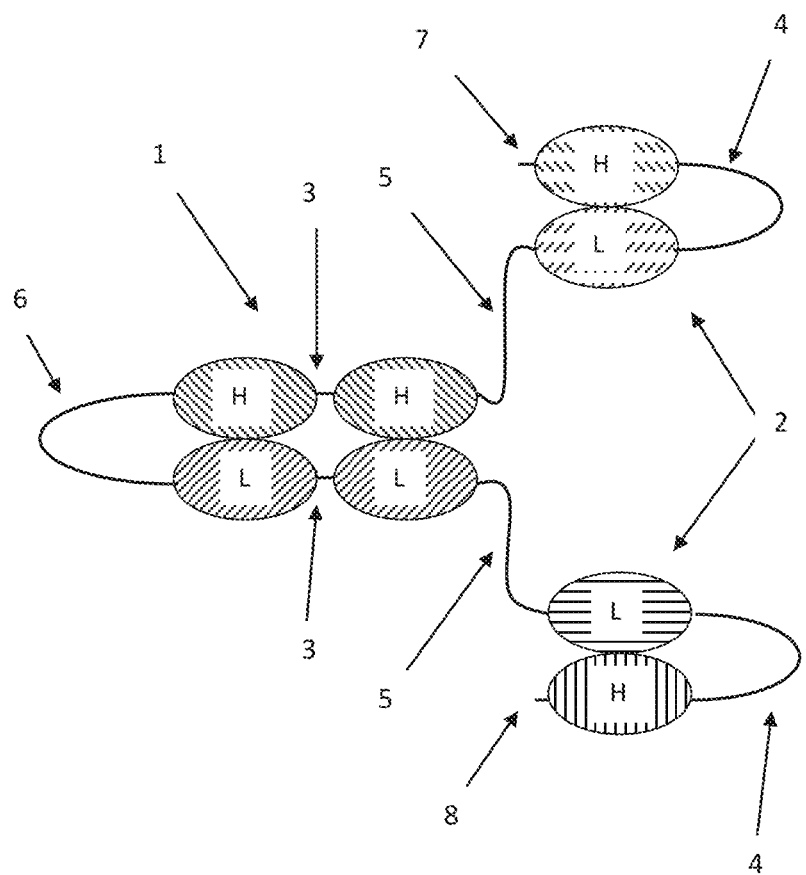
FIG. 1 shows a tetravalent, trispecific Fv antigen-binding molecule consisting of a single polypeptide having a eight variable domains linked one after another in the orientation $V_H$-$V_L$-$V_H$-$V_H$-$V_L$-$V_L$-$V_L$-$V_H$ from the N-terminus 7 to the C-terminus 8 of the polypeptide. Such domain orientation is only an example and other arrangements are possible as described above. Two single-chain Fv (scFv) units 2 are distally connected to a single chain diabody unit 1 by the peptide linkers 5, wherein a variable light chain ($V_L$) domain of one scFv unit 2 is linked C-terminally by a peptide linker 5 to the N-terminus of a variable heavy chain ($V_H$) domain of the first pair of variable domains of the diabody unit 1. The $V_L$ of the scFv unit 2 is N-terminally linked with the $V_H$ of the scFv unit by a long peptide linker 4. The $V_H$ of the first pair of variable domains is linked by a short peptide linker 3 to another $V_H$ domain of the first pair of variable domains. The first pair of variable domains is C-terminally linked by a long peptide linker 4 with the N-terminus of the second pair of variable domains of the diabody, which are both $V_L$ domains. The two $V_L$ domains of the second pair of variable domains are linked by a short peptide linker 3. The second pair of variable domains of the diabody is C-terminally connected with the N-terminus of a $V_L$ domain of another scFv unit 2 located at the C-terminus of the polypeptide. The scFv unit 2 at the C-terminus of the polypeptide consists of the $V_L$ domain linked by a long linker 4 with a $V_H$ domain. The two scFvs units 2 have antigen binding sites with different specificities and the diabody unit 1 has two antigen binding sites for the same specificity.

In certain embodiments each of the other variable domains linked N-terminally and C-terminally to the pair of variable domains of the diabody-unit in the same polypeptide is part of a further antigen binding site. Hence, one pair of variable domains of the diabody-unit (first pair) associates with the other pair of variable domains of the diabody-unit (second pair) to two antigen binding sites (first and second antigen binding site) and the further N-terminally located variable domain associates with a corresponding variable domain to a third antigen binding site and the C-terminally located further variable domain associates with a corresponding variable domain to a fourth antigen binding site. Therefore, such multivalent Fv antibody is at least tetravalent. In certain embodiments this antigen binding site which may comprise the further variable domain linked N-terminally and/or C-terminally to the pair of variable domains of the diabody-unit is a scFv-unit or a single-chain diabody-unit (scDb). In other embodiments the further variable domains linked N-terminally and C-terminally to the pair of variable domains of the diabody-unit in the same polypeptide (first polypeptide) is associated with corresponding $V_H$ or $V_L$ domains of another polypeptide (second polypeptide) which may comprise the second (other) pair of variable domains of the diabody-unit thereby forming another two $V_H/V_L$ (third and fourth) antigen binding sites between the variable domains of two (first and second) polypepetides.

In certain embodiments the two pairs of variable domains of the diabody-unit are a pair of variable light chain domains ($V_L$-$V_L$) linked one after another in a polypeptide and a pair of variable heavy chains ($V_H$-$V_H$) linked one after another in a polypeptide, wherein the $V_L$-$V_L$ pair and the $V_H$-$V_H$ pair associate to two $V_L/V_H$ (first and second) antigen binding sites.

In certain embodiments the multivalent antibody molecule may comprise a diabody-unit, i.e., a pair of variable domains of the diabody-unit, integrated into a polypeptide chain having at least six variable domains, e.g., six, eight or ten, linked one after another.

The diabody-unit consists of a pair of two variable domains linked one after another such that these domains cannot fold intramolecularly into a functional Fv unit, i.e., a $V_H/V_L$ antigen binding unit, and instead associate with another pair of two variable domains linked one after another to form a bivalent dimer, i.e. diabody, for providing two antigen binding sites. By linking a pair of variable light chain domains ($V_L$-$V_L$) one after another and a pair of variable heavy chain domains ($V_H$-$V_H$) one after another intramolecular pairing of the domains within each pair is prevented due to the same kind of domains, i.e., $V_H$-$V_H$ or $V_L$-$V_L$. The rigid and compact structure of the diabody-unit facilitates the manufacturing, correct folding of the multivalent antibody and increases the stability of the antibody. Such a diabody-unit generates two VHN/$V_L$ antigen binding sites within the antibody molecule by two non-covalently bonded $V_H$ and $V_L$ domains which is advantageous for the stability of the antibody molecule, because it leads to a more compact molecule. In certain embodiments the pair of two variable domains is linked by a short linker.

Figure 2:
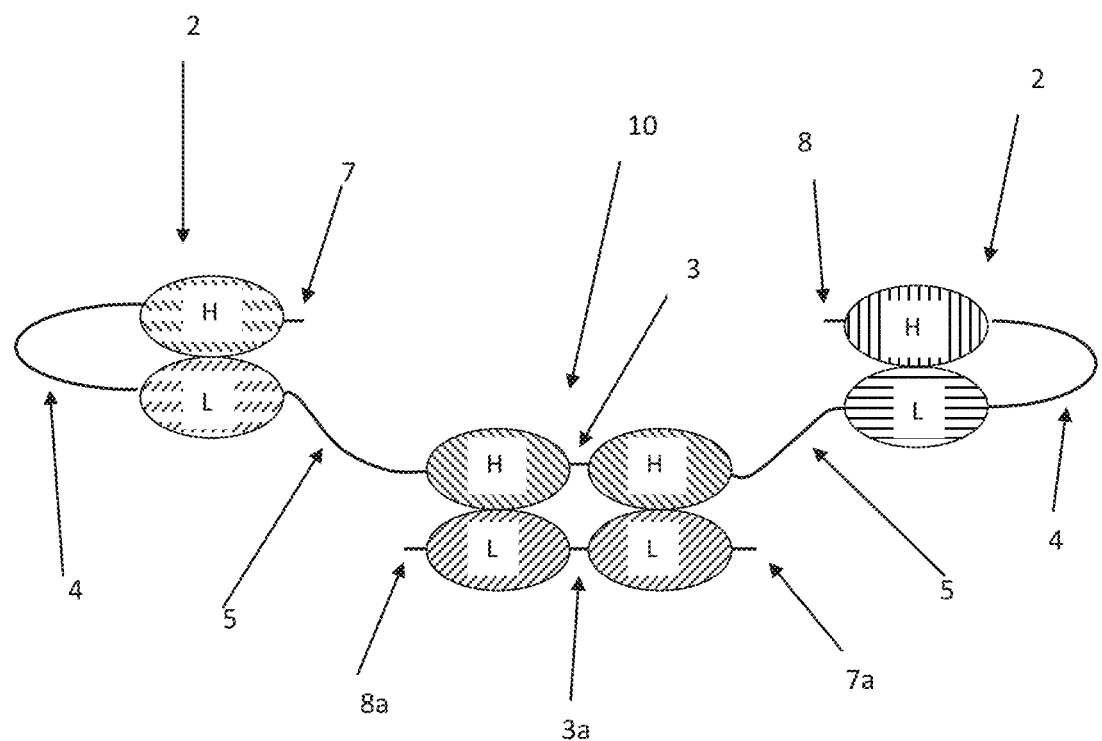
FIG. 2 shows a tetravalent, trispecific Fv antigen-binding molecule consisting of a first polypeptide having six variable domains linked one after another in the orientation $V_H$-$V_L$-$V_H$-$V_H$-$V_L$-$V_H$ from the N-terminus 7 to the C-terminus 8 of the first polypeptide and a second polypeptide having two variable domains linked one after another in the orientation $V_L$-$V_L$ from the N-terminus 7a to the C-terminus 8a of the second polypeptide. Such domain orientation is only an example and other arrangements are possible as described above. The Fv antigen binding molecule may comprise a dimeric diabody unit 1 formed by a first pair of two variable domains integrated in the first polypeptide associated with a second pair of two variable domains in the second polypeptide. Each of the two variable domains of the first pair of two variable domains integrated in the first polypeptide is linked to a scFv unit 2. In each of the scFv units 2 the variable domains are linked by a long peptide linker 4. The N-terminal scFv unit 2 is C-terminally linked by a peptide linker 5 to the N-terminus of the first pair of variable domains of the diabody unit 1. This first pair of variable domains consists of two $V_H$ domains linked by a short peptide linker 3. The first pair of variable domains of the diabody unit 1 is C-terminally linked by a peptide linker 5 to the N-terminus of a scFv unit 2 located at the C-terminus of the first polypeptide. The two scFvs units 2 have antigen binding sites with different specificities and the diabody unit 1 has two antigen binding sites for the same specificity.

In certain instances two single-chain Fv (scFv) fragments are distally connected to the diabody-unit providing two further $V_H/V_L$ antigen binding sites (FIGS. 1 and 2). Hence, such multivalent antibody molecule is at least tetravalent, because it provides at least four antigen binding sites; two by the diabody-unit and two by the two scFv-units. Each of the distally located scFv fragments may be arranged in the order $V_H$-$V_L$ or $V_L$-$V_H$ in the polypeptide.

Such tetravalent antibody molecules are advantageous for generating tetravalent, pentavalent or hexavalent trispecific antibodies. These novel trispecific antibodies can be used, for example, for recruiting immune effector cells to kill target cells, e.g. tumor cells, or virally infected cells. Because such trispecific antibodies according to the invention are at least tetravalent, they provide an increased functional activity relative to trivalent and trispecific single-chain fragments. Trispecific and tetravalent antibodies according to the invention bind bivalently by two of the four binding sites to both, the target cell as well as the immune effector cell. For instance, bivalent binding to the target cell does not only increase the avidity, but also increases the targeting specificity when the two of the three antigen specificities are for two different antigens, e.g. two different tumor antigens, on the cell surface of the target cell. On the other hand, the cytotoxic efficiency of the recruited immune effector cell can be modulated, in particular increased, when the antibody binds bivalently to the immune effector cell. In other instances, such trispecific antibody may have two specificities for different antigens on the effector cells and a third specificity for an antigen on a tumor cell, neuron, or virally infected cell or bind and eventually neutralize a soluble protein like growth-factor, cytokines or other non-cell-bound ligands.

In certain instances the variable domains of the diabody-unit which are linked by a short linker that prevents intramolecular pairing are both either variable light chain domains ($V_L$-$V_L$) or variable heavy chain domains ($V_H$-$V_H$) (FIGS. 1 and 2). It was found that this particular domain arrangement facilitates correct folding of multispecific and multivalent antibody molecules according to the invention. In particular for tetravalent, trispecific or tetraspecific Fv antibody molecules this measure can be taken for enabling a correct association of the Fv antibody molecule having variable domains for three or more different specificities and to prevent incorrect association within a single polypeptide (monomer) or homodimerization between two identical Fv polypeptides instead of correct heterodimerization of the first with the second polypeptide (Example 2). The inventors have obtained a correct association between the variable domains for three specificities and two different polypeptides providing the variable domains by integrating into the trispecific antibody molecule such a diabody-unit formed by a first pair of two variable heavy domains linked by a short linker associated with a second pair of two corresponding variable light domains linked by a short linker. Hence, such variable domain arrangement in the diabody-unit, i.e. $V_L$-$V_L$ in the first polypeptide of variable domains and $V_H$-$V_H$ in the second polypeptide of variable domains, enables the correct association and folding of a tetravalent and trispecific or tetraspecific Fv antibody. The inventors found that such $V_L$-$V_L$/$V_H$-$V_H$ arrangement in the diabody unit or single chain diabody unit forces the correct folding of a long polypeptide which may comprise more than six variable domains linked one after another to an Fv antibody molecule (e.g. FIG. 1) or the correct folding and heterodimerization of two polypeptides with different lengths to a functional dimeric Fv antibody molecule (e.g. FIGS. 2, 5, 6a, 6b).

Figure 4:
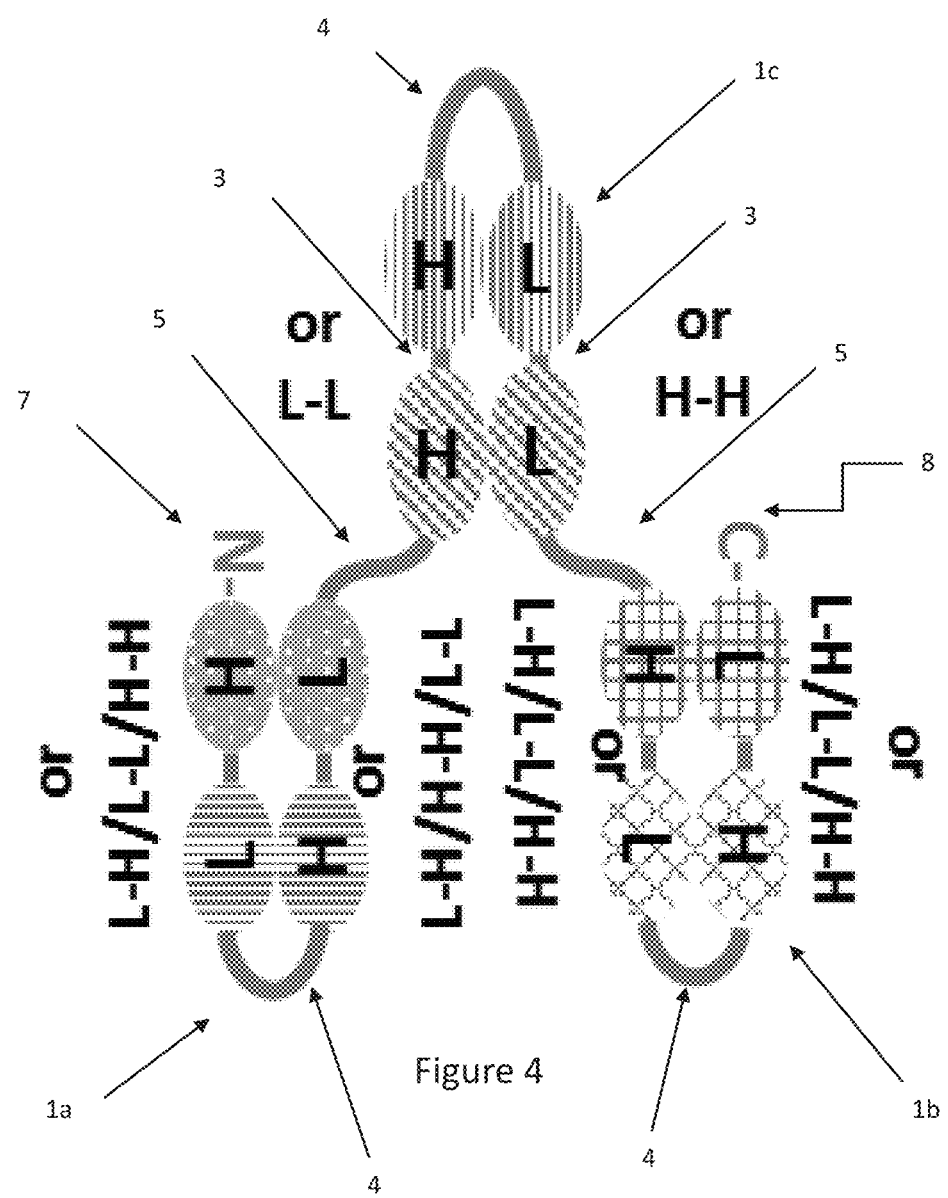
FIG. 4 shows a hexavalent Fv antigen-binding molecule consisting of a single polypeptide having twelve variable domains linked one after from the N-terminus 7 to the C-terminus 8 of the polypeptide. The domain orientation is only an example and other arrangements indicated for each pair of juxtaposed variable domains are possible. Two single chain diabody units 1a, 1b are distally connected to a single chain diabody unit 1c by the peptide linkers 5, wherein a variable domain of one single chain diabody unit 1a is linked C-terminally by a peptide linker 5 to the N-terminus of a variable domain of the first pair of variable domains of the diabody unit 1c and a variable domain of the single chain diabody unit 1b is N-terminally linked by a linker 5 to the C-terminus of the second pair of variable domains of single chain diabody unit 1c. The first and second pairs of variable domains of each of the three single chain diabody units 1a, 1b, 1c are linked with each other by a long peptide linker 4. In each of the single chain diabody units 1a, 1b, 1c one of the variable domains of the first pair of variable domains is linked by a short peptide linker 3 to the other variable domain of the first pair of variable domains and the two variable domains of the second pair of variable domains are linked by a short peptide linker 3.
Figure 5:
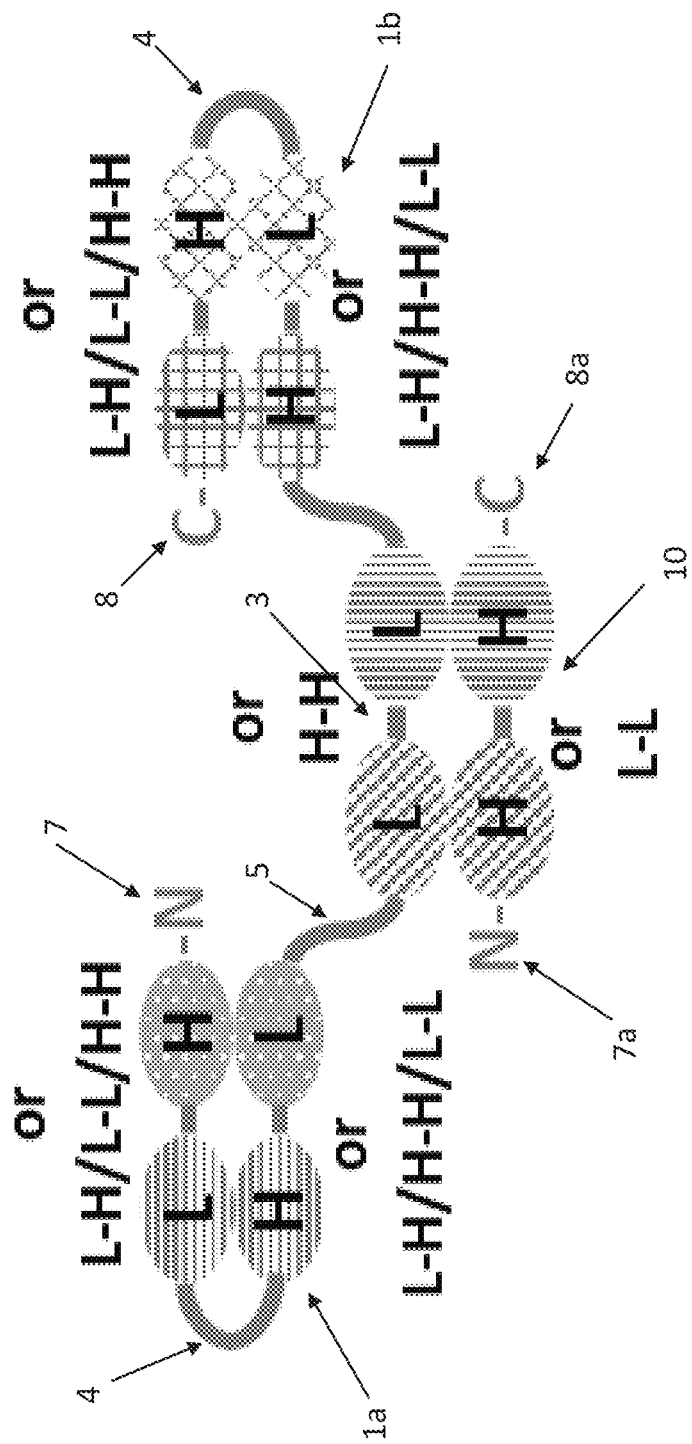
FIG. 5 shows a hexavalent Fv antigen binding molecule consisting of a first polypeptide having 10 variable domains linked one after another from the N-terminus 7 to the C-terminus 8 of the first polypeptide and a second polypeptide having two variable domains linked one after another from the N-terminus 7a to the C-terminus 8a of the second polypeptide. The particular domain orientation in the Figure is only an example and the other arrangements indicated for each of the pairs of juxtaposed variable domains are possible. The Fv antigen binding molecule may comprise a dimeric diabody unit 10 formed by a first pair of two variable domains of the first polypeptide associated with a second pair of two variable domains in the second polypeptide. Each of the two variable domains of the first pair of two variable domains of the first polypeptide is linked to a single chain diabody unit 1a, 1b. In each of the single chain diabody units 1a, 1b the two pairs of juxtaposed variable domains are linked by a long peptide linker 4. The N-terminal single chain diabody unit 1a is C-terminally linked by a peptide linker 5 to the N-terminus of the first pair of variable domains of the diabody unit 10. This first pair of variable domains consists of two $V_H$ domains linked by a short peptide linker 3. The first pair of variable domains of the diabody unit 10 is C-terminally linked by a peptide linker 5 to the N-terminus of a single chain diabody unit 1b located at the C-terminus of the first polypeptide.

In further embodiments at least one single-chain diabody-unit (scDb) is distally linked to the diabody-unit providing at least one further antigen binding site. Hence, at least one polypeptide of the diabody unit may comprise one pair of the variable domains of the diabody-unit linked to at least one scDb in the polypeptide. For example, two scDb units are distally linked to the diabody-unit providing further two antigen bindings sites per each single chain diabody-unit (FIGS. 4 and 5). Hence, such multivalent antibody molecule is at least tetravalent, because it provides at least four antigen binding sites. Such multivalent antibody is at least hexavalent in embodiments, where at least two scDb units are linked to the diabody-unit, because of the two distally oriented scDb units providing four antigen binding sites and two antigen binding sites provided by the diabody-unit. In each of the distally scDb-units the variable domains may be arranged in the order $V_H$-$V_L$-$V_H$-$V_L$, $V_L$-$V_H$-$V_L$-$V_H$, $V_L$-$V_L$-$V_H$-$V_H$ or $V_H$-$V_H$-$V_L$-$V_L$ in the polypeptide.

In certain embodiments the diabody-unit consists of two pairs of variable domains arranged on two polypeptides associated with one another, thereby forming two antigen-binding sites and each of the two polypeptides may comprise at least one other single-chain fragment and/or single-chain diabody fragment distally located to each of the two pairs of variable domains of the diabody unit. (FIGS. 6A, 6b, 7, 8a and 8b). Hence, such multivalent antibody molecule is at least heptavalent, because it provides at least five antigen binding sites; two binding sites by the diabody-unit, at least two binding sites by the two scFv-units or scDb-units N-terminally and C-terminally to the first pair of variable domains of the diabody unit and at least one binding site N-terminally or C-terminally to the other pair of variable domains of the diabody unit of the other polypeptide of the diabody unit.

In certain instances the present invention refers to a multivalent antibody molecule which may comprise a polypeptide which may comprise at least six variable domains linked one after another, wherein a diabody-unit which may comprise first two variable domains of said at least six variable domains is integrated into said polypeptide and said first two variable domains of the diabody-unit are associated with another two variable domains of the diabody-unit, i.e., second two variable domains, to form two antigen binding sites. The second two variable domains may be located in the same polypeptide with the first two variable domains or in a separate second polypeptide associated with the first polypeptide. The two antigen binding sites provided by the diabody unit are formed between the first and second variable domains, wherein each variable domain of the first pair of variable domains forms an antigen-binding site with another variable domain of the second pair of variable domains. Hence, the diabody-unit is formed by said first and second two variable domains, wherein the two variable domains are linked by a short peptide linker in the first as well as the second two variable domains for preventing intramolecular pairing.

Thus, in certain embodiments the present invention refers to a multivalent antibody molecule which may comprise a polypeptide having, i.e. which may comprise, at least six variable domains linked one after another, wherein two variable domains of the polypeptide are linked by a peptide linker preventing intramolecular pairing and said two variable domains are associated with another two corresponding variable domains linked by a peptide linker preventing intramolecular pairing, said four variable domains forming two antigen binding sites between said four variable domains. For example, such antibody is an Fv antibody, in particular a tetravalent and trispecific Fv antibody.

The antibody molecule is multivalent, i.e. possess more than one antigen binding site. It is tetravalent, when it has four antigen binding sites; pentavalent, when it has five antigen binding sites and hexavalent, when it has six antigen binding sites. "Tetravalent" refers to an antibody molecule which may comprise, in particular consisting of, four Fv antigen-binding sites, wherein each of the Fv antigen-binding sites may comprise a $V_H$/$V_L$ pair having a variable heavy chain ($V_H$) domain and a variable light chain ($V_L$) domain of the same antigen epitope specificity associated with one another. Thus, such tetravalent antibody molecule may comprise at least eight variable antibody domains, namely four variable heavy chain ($V_H$) domains and four variable light chain ($V_L$) domains. Because the tetravalent antigen-binding molecule may comprise at least eight antibody variable domains its molecular weight is above 100 kDa which results in a longer half-life of such a molecule compared with trivalent and trispecific single-chain Fv molecules.

In certain instances the antibody molecule is multispecific, i.e possess specificities for different antigen epitopes. In certain instances the antibody molecule is trispecific.

A trispecific and tetravalent antibody molecule may comprise an antigen-binding site having specificity against a first antigen epitope, an antigen-binding site having specificity against a second antigen epitope and two antigen-binding sites having specificity against a third antigen epitope. Thus, such trispecific and tetravalent antibody molecule has, i.e. may comprise, different specificities for three different antigen epitopes. For example, such antigen-binding molecule may comprise a first antigen-binding site having specificity against a first antigen epitope, a second antigen-binding site having specificity against a second antigen epitope, a third and a fourth antigen-binding sites having specificity against a third antigen epitope. A pentavalent and trispecfic antibody molecules may comprise two antigen binding sites having specificity against a first antigen epitope, two antigen-binding sites having specificity against a second antigen epitope and one antigen-binding site having specificity against a third antigen epitope. Alternatively, a pentavalent and trispecifc antibody molecule may comprise three antigen-binding sites against a first antigen epitope and one antigen-binding site against each of the second and third antigen epitope. A hexavalent and trispecific antibody molecule may comprise in certain embodiments two antigen-binding sites for each of the three antigen epitopes or, alternatively one to three antigen binding sites for each of the three antigen epitopes.

In certain instances the antibody molecule is an Fv antibody molecule. "Fv antibody" refers to an Fv-derivative of an immunglobulin which may comprise only variable (V) antibody domains, but is devoid of constant antibody regions or fragments thereof. Each variable light chain domain ($V_L$) associates with a corresponding variable heavy chain domain ($V_H$) forming an Fv antigen binding site ($V_H/V_L$ antigen binding site). The variable antibody domains are linked with one another by a peptide linker or a peptide bond into a fusion polypeptide. The Fv antibody, i.e., antigen-binding molecule, according to the invention can be a monomer of a single polypeptide or a multimeric polypeptide. A multimeric antigen-binding molecule, i.e. Fv antibody, in particular multivalent Fv antibody, can be, for example, a dimer having two polypeptides, a trimer having three polypeptides or a tetramer having four polypeptides. The dimer is heterodimeric, if it consists of two polypeptides having different amino acid compositions, or is homodimeric, if it consists of two identical polypeptides.

The term "polypeptide" refers to a polymer of amino acid residues linked by amide bonds. The polypeptide is, preferably, a single chain fusion protein which is not branched. Within the polypeptide the antibody variable (Fv) domains are linked one after another. A "Fv polypeptide" denotes a fusion polypeptide wherein antibody variable (Fv) domains are linked one after another. The polypeptide may have contiguous amino acid residues in addition N-terminal and/or C-terminal. For example, the polypeptide may contain a Tag sequence, preferably at the C-terminus which might be useful for the purification as well as detection of the polypeptide. Example of a Tag sequence are a His-Tag, e.g. a His-Tag consisting of six His-residues, a FLAG-Tag, e.g. a DYKDDDDK octapeptide (SEQ ID NO:38) or STREP® II-Tag, e.g a WSHPQFEK octapeptide (SEQ ID NO:39). or a C-Tag, e.g. an EPEA tetrapeptide (SEQ ID NO:40). For a multimeric antigen-binding molecule, different Tag sequences may be used for different polypeptides, e.g. a His-Tag for the first polypeptide and a FLAG-Tag for the second polypeptide of a dimeric molecule. In certain embodiments the polypeptide may comprise variable domains providing the antigen-binding sites and further constant antibody domains, for example $C_L$, $C_H$ and/or Fc-domains. For example, such embodiments may comprise an Fv polypeptide or Fv antibody fused to at least one constant antibody domain, for example a Fc domain. In further embodiments the polypeptide which may comprise the variable domains may be coupled to another agent, e.g. a toxin, an immune-modulating agent or a signal generating agent.

"Linker" refers to a peptide connecting two juxtaposed variable domains in the polypeptide between the C-terminus of one domain and the N-terminus of the other juxtaposed domain or vice versa. Regarding the amino acid composition a peptide is selected that do not interfere with the formation of Fv, i.e. $V_H/V_L$, antigen binding sites as well as do not interfere with the multimerization, e.g. dimerization of multispecific, e.g. trispecific, molecules. For example, a linker which may comprise glycine and serine residues generally provides protease resistance. In some embodiments $(G_2S)_x$ peptide linkers are used, wherein, for example, x=1-20, e.g. $(G_2S)$, $(G_2S)_2$, $(G_2S)_3$, $(G_2S)_4$, $(G_2S)_5$, $(G_2S)_6$, $(G_2S)_7$ or $(G_2S)_8$, or $(G_3S)_x$ peptide linkers are used, wherein, for example, x=1-15 or $(G_4S)_x$ peptide linkers are used, wherein, for example, x=1-10, preferably 1-6. The amino acid sequence of the linker can be optimized, for example, by phage-display methods to improve the antigen binding and production yield of the polypeptide.

The length of the linkers influences the flexibility of the antigen-binding polypeptide dimer. The desired flexibility of the antigen-binding polypeptide dimer depends on the target antigen density and the accessibility of the target antigen, i.e. epitopes on the target antigen. Longer linkers provide more flexible antigen-binding polypeptides with more agile antigen-binding sites. The effect of linker lengths on the formation of dimeric antigen-binding polypeptides is described, for example, in Todorovska et al., 2001 Journal of Immunological Methods 248:47-66; Perisic et al., 1994 Structure 2:1217-1226; Le Gall et al., 2004, Protein Engineering 17:357-366 and WO 94/13804.

A diabody-unit is integrated into the polypeptide of the antibody molecule. "Diabody unit" denotes a bivalent Fv-module consisting of two pairs of variable domains, a first pair and a second pair, which associate to two $V_L/V_H$ antigen binding sites. Each pair of variable domains is linked one after another in a polypeptide. In certain embodiments the bivalent Fv-module consists of a first and a second pair of two juxtaposed variable domains, wherein in each pair the two variable domains are fused by a short peptide linker that precludes intramolecular association between the variable domains connected by the short linker. The first pair of variable domains is forced to associate with the second pair of variable domains for forming two Fv antigen binding sites with the two pairs of variable domains. Hence, each of the two Fv antigen binding sites is formed by one variable domain of the first pair of variable domains and one variable domain of the second pair of variable domains. Therefore, such diabody-unit may comprise at least one antigen binding site of two variable domains which are not directly connected by a short peptide linker 3, 3a (FIGS. 1 and 2). The two pairs of juxtaposed variable domains are either located on two separated polypeptides forming a dimeric diabody unit (FIGS. 2, 3, 5-8) or the two pairs of juxtaposed variable domains are located on the same polypeptide forming a single-chain diabody unit (FIGS. 1, 4). In each pair of variable domains the short linker 3, 3a connects the C-terminus of one variable domain with the N-terminus of the other variable domain or vice versa. In each pair the variable domains can be oriented from the N- to the C-terminus as $V_L$-$V_H$, $V_H$-$V_L$, $V_H$-$V_H$ or $V_L$-$V_L$, wherein the two variable domains of the pair have different antigen epitope specificities or the same antigen epitope specificity. In certain instances the two variable domains are directly linked by a peptide bond between the N-terminus of one variable domain and the C-terminus of the other variable domain of the pair. The length of the short peptide linker connecting the two variable domains in each of the first and second pair of variable domains of the diabody-unit is such that an intramolecular association between the variable domains connected by the linker is precluded. Such linker are "short", i.e. consists of 0, 1, 2, 3, 4, 5, 6, 7, 8, 9, 10, 11 or about 12 amino acid residues In the case of 0 amino acid residues the linker is a peptide bond. Such short linker favors the correct dimerization between the two pairs of variable domains and formation of two Fv antigen binding sites. Shortening the linker to about 12 or less amino acid residues generally prevents adjacent domains of the same polypeptide chain from interacting with each other. In an embodiment of the invention these linkers consist of about 3 to about 12, for example 5 to 10, in particular 7 to 9 contiguous amino acid residues. The linker length may be adjusted to the particular domain orientation within the diabody-unit. For example, a (G$_2$S)$_2$ linker may be used for a V$_H$-V$_L$ pair or a V$_L$-V$_H$ pair and a (G$_2$S)$_3$ linker may be used for a V$_H$-V$_H$ pair or V$_L$-V$_L$ pair or a (G$_2$S)$_2$ linker may be used for a V$_H$-V$_H$ pair and a (G$_2$S)$_3$ linker may be used for a V$_L$-V$_L$ pair of a diabody unit (or vice versa). Besides, it is in principle possible that two polypeptides having a linker with more than 12 amino acid residues between the variable antibody domains of the pair correctly dimerize with one another (see for example Le Gall et al., 2004, Protein Engineering 17:357-366).

In certain embodiments the diabody-unit is a single chain diabody-unit (FIG. 1). A "single chain diabody-unit" consists of a first pair of variable domains connected to a second pair of variable domains by a long linker allowing intramolecular association of the first and second pairs of variable domains as defined as a "long linker" used in scFv units and described in the next paragraph. For example, such long linker may consist of more than 12, in particular about 15 to about 50, preferably about 15 to about 35, in particular from about 15 to about 25 contiguous amino acid residues.

In certain embodiments the domains of the single chain diabody linked one after another in a polypeptide may be arranged in the order V$_L$-V$_H$-V$_L$-V$_H$, V$_L$-V$_L$-V$_H$-V$_H$, V$_H$-V$_H$-V$_L$-V$_L$ or V$_H$-V$_L$-V$_H$-V$_L$ from the N-terminus to the C-terminus of the single chain diabody-unit.

In certain embodiments the antibody molecule of the invention consists of a single polypeptide which may comprise a single chain diabody-unit (FIGS. 1, 4). In particular embodiments the antibody molecule may comprise at least three single chain diabody-units linked one after another in a polypeptide (FIG. 4). In other embodiments the antibody molecule of the invention may comprise at least one single chain diabody-unit linked distally to a diabody-unit (FIG. 5).

A "single-chain Fv (scFv) unit" denotes an Fv antigen binding site formed by a fragment of a single polypeptide consisting of a variable light chain domain (V$_L$) and a variable heavy chain domain (V$_H$). The variable domains can be oriented as V$_L$-V$_H$ or V$_H$-V$_L$ from the N-terminus to the C-terminus of the scFv unit. The variable domains are connected between the C-terminus of one variable domain and the N-terminus of the other variable domain or vice versa by a peptide linker. The peptide linker is long and flexible (in general consisting of about 12 or more amino acid residues) for folding intramolecularly and forming the Fv antigen binding site. Additional amino acid residues provide extra flexibility. For example, such long linker may consist of more than 12, in particular about 15, to about 50, preferably about 15 to about 35, in particular from about 15 to about 25 contiguous amino acid residues. The linker length may be adjusted to the particular domain orientation from the N-terminus to the C-terminus within the scFv unit. For example, a (G$_2$S)$_6$ linker may be used for a V$_H$-V$_L$ scFv unit and a (G$_2$S)$_7$ linker may be used for a V$_L$-V$_H$ scFv unit.

The scFv unit is connected to the diabody-unit by a peptide linker between a variable domain of the scFv unit and a variable domain of the diabody unit. The length of the peptide linker is chosen to avoid steric hindrance between juxtaposed variable domains and to maintain stability of the molecule and may be, for example, from 5 to 50, in particular from 5 to 35, preferably have at least 6, 7, 8, 9, 10, 11, 12, 13, 14 or 15 contiguous amino acid residues.

Figure 6A:
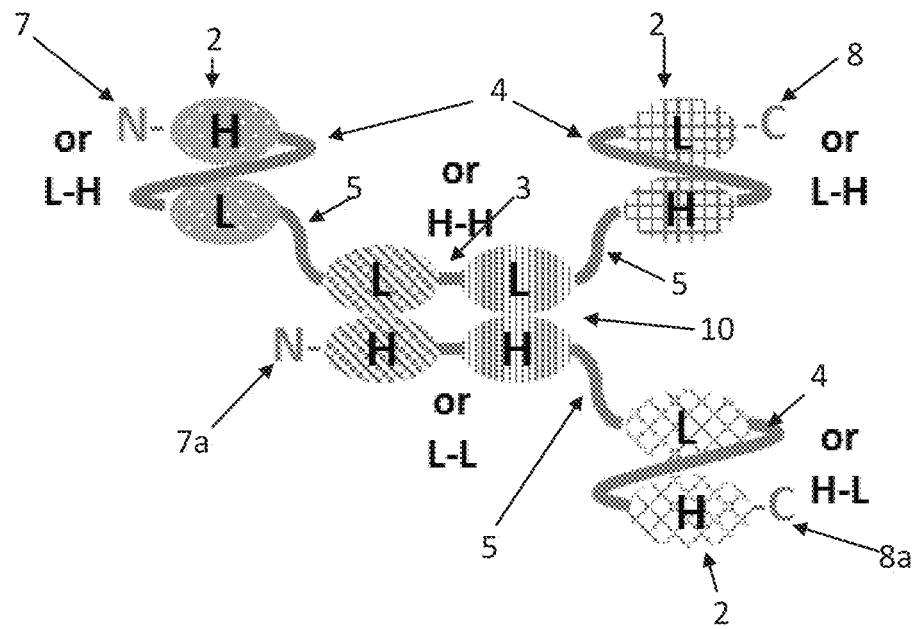
FIGS. 6a-6b shows a pentavalent Fv antigen-binding molecule consisting of a first polypeptide having six variable domains linked one after another from the N-terminus 7 to the C-terminus 8 of the first polypeptide and a second polypeptide having four variable domains linked one after another from the N-terminus 7a to the C-terminus 8a of the second polypeptide. The domain orientation is only an example and other arrangements for each juxtaposed pair of variable domais are possible as indicated in the Figure. The Fv antigen binding molecule may comprise a dimeric diabody unit 10 formed by a first pair of two variable domains of the first polypeptide associated with a second pair of two variable domains in the second polypeptide. Each of the two variable domains of the first pair of two variable domains of the first polypeptide is linked to a scFv unit 2. In each of the scFv units 2 the variable domains are linked by a long peptide linker 4. The N-terminal scFv unit 2 is C-terminally linked by a peptide linker 5 to the N-terminus of the first pair of variable domains of the diabody unit 10. This first pair of variable domains consists of two variable domains linked by a short peptide linker 3. The first pair of variable domains of the diabody unit 10 is C-terminally linked by a peptide linker 5 to the N-terminus of a scFv unit 2 located at the C-terminus of the first polypeptide. A) the second polypeptide which may comprise four variable domains consists of the second pair of variable domains of the diabody unit 10 linked with a scFv unit 2 C-terminally and B) the second polypeptide which may comprise four variable domains consists of the second pair of variable domains of the diabody unit 10 linked with a scFv unit 2 N-terminally.
Figure 6B:
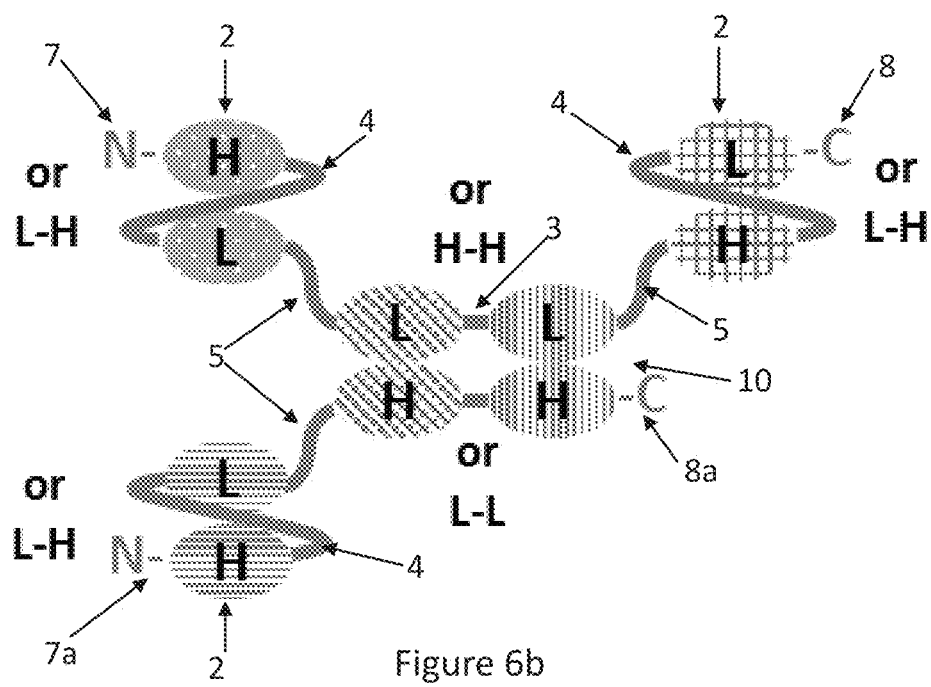
Figure 7:
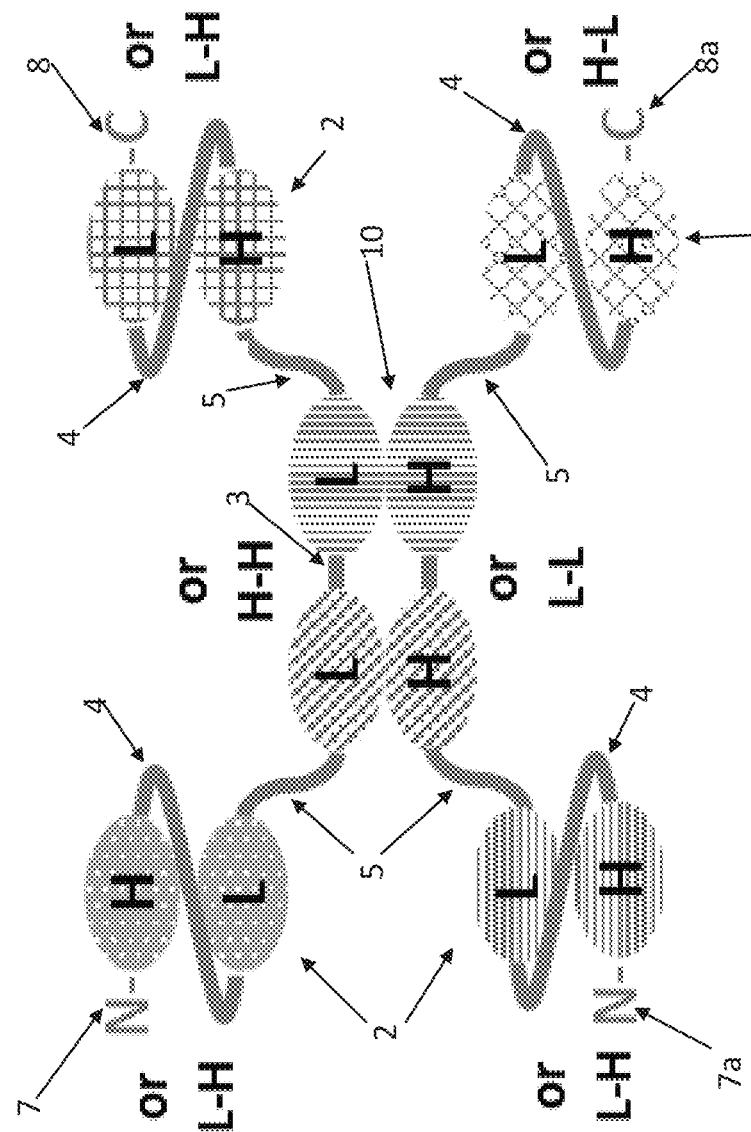

In certain instances the diabody-unit is centrally located within the antibody molecule for facilitating the folding and improving the stability of the antibody molecule. In such instances the diabody-unit is N-terminally and C-terminally connected with further distal variable domains. In certain embodiments the diabody-unit is connected with two (FIGS. 1, 2, 8a, 8b), three (FIGS. 6a, 6b) or four (FIG. 7) scFv-units. In certain instances the antibody molecule, in particular trispecific Fv antibody molecule, may comprise a polypeptide having at least six variable domains, wherein said polypeptide may comprise a scFv unit at the N-terminus, a scFv unit at the C-terminus and a first pair of two variable domains of a diabody-unit located between the two scFv units (FIGS. 1 and 2). This first pair of two variable domains of the diabody-unit does not associate to an Fv antigen-binding site. For instance, if the diabody-unit is a dimeric diabody-unit each of the two variable domains of the first pair of juxtaposed variable domains is linked to a further variable domain. In particular, each of the two variable domains of the first pair of juxtaposed variable domains is linked to a further variable domain of a scFv unit (FIG. 2). In further instances additionally one or both variable domains of the second pair of juxtaposed variable domains may be linked to a further variable domain (FIGS. 6a, 6b, 7). If the diabody-unit is a single-chain diabody unit the first pair of juxtaposed variable domains is N-terminally linked to a further variable domain and the second pair of juxtaposed variable domains is C-terminally linked to a further variable domain. In particular, the first pair of juxtaposed variable domains is N-terminally linked to a further variable domain of a scFv unit and the second pair of juxtaposed variable domains is C-terminally linked to a further variable domain of another scFv unit (FIG. 1). In other embodiments the first pair of variable domains of a first single chain diabody units is N-terminally linked to a further variable domain of a second single chain diabody unit and the second pair of variable domains of the first single chain diabody is C-terminally linked to a further variable domain of a third single chain diabody unit resulting in a polypeptide which may comprise three single chain diabody units linked one after another (FIG. 4). In further instances at least one further variable domain may be located between the first and the second pair of juxtaposed variable domains.

In certain instances where the diabody-unit is a single chain diabody unit, the multivalent antibody consists of a single polypeptide which may comprise two juxtaposed variable domains, i.e. the first pair of juxtaposed variable domains, associated with two other juxtaposed variable domains of this polypeptide, i.e. the second pair of variable domains (FIG. 1). Such antibody structure is favorable for providing multispecific, in particular bi-, tri-, or tetraspecific antibodies. In certain embodiments such multivalent, in particular trispecific Fv, antibody has at least eight variable domains linked one after another from the N-terminus to the C-terminus, a first and a second variable domain forming a scFv-unit at the N-terminus, said scFv-unit at the N-terminus is linked C-terminally to a third variable domain of a first pair of variable domains of a diabody-unit which may comprise the third variable domain and a forth variable domain, said fourth variable domain is linked C-terminally to a fifth variable domain of a second pair of variable domains of the diabody-unit which may comprise the fifth and a sixth variable domains, said sixth variable domain is linked C-terminally to a seventh variable domain of a scFv-unit at the C-terminus and said scFv-unit is formed by the seventh and a eight variable domains (FIG. 1). The variable domains may be arranged from the N-terminus to the C-terminus of the polypeptide, for example, in one of the following orientations: V$_H$-V$_L$-V$_L$-V$_H$-V$_L$-V$_H$-V$_L$-V$_H$, V$_H$-V$_L$-V$_H$-V$_H$-V$_L$-V$_L$-V$_L$-V$_H$, V$_L$-V$_H$-V$_L$-V$_H$-V$_L$-V$_H$-V$_H$-V$_L$ or V$_H$-V$_L$-V$_L$-V$_L$-V$_H$-V$_H$-V$_L$-V$_H$. In a particular embodiment one pair of variable domains of the diabody-unit has the orientation $V_H$-$V_H$ and the other pair of variable domains of the diabody unit has the orientation $V_L$-$V_L$ (FIG. 1).

Tetravalent embodiments of an antibody molecule consisting of a single polypeptide having eight variable domains as described in the foregoing are favorable for trispecific antibodies. For example, such trispecific antibodies can provide a first and second antigen specificity for a target cell, e.g. tumor cell, and a third specificity for an immune effector cell, e.g. T- or NK-cell. In other instances, such trispecific antibody may have two specificities for different antigens on the effector cells and a third specificity for an antigen on a tumor cell. In some embodiments the two distal scFv units may have the first and the second specificity for the target cell and the diabody unit between the two scFv units may have specificity for an immune effector cell; i.e., from the N-terminus to the C-terminus the first and second variable domain has the first specificity for the target cell; the third and fifth variable domains have the third specificity for the immune effector cell, the fourth and sixth variable domains have the third specificity for the immune effector cell and the seventh and eight variable domains have the second specificity for the target cell (FIG. 1). In other embodiments the two distal scFv units may have specificity for the immune effector cell and the two antigen binding sites formed by the diabody-unit may have two different specificities for the target cell; i.e. from the N-terminus to the C-terminus the first and the second as well as the seventh and the eight variable domains have the third specificity for the immune effector cell, the third and the fifth variable domains have the first specificity for the target cell and the fourth and the sixth variable domains have the second specificity for the target cell. In further alternative embodiments the single polypeptide may have more than eight variable domains, e.g. 10, 12 or more, and may comprise more than two scFv units and/or more than one diabody unit.

In further embodiments the multivalent antibody molecule consisting of one polypeptide may comprise three single chain diabody units linked one after another (FIG. 4). Such antibody molecule has at least 12 variable domains linked one after another from the N-terminus to the C-terminus. In a particular embodiment one pair of variable domains of the second single chain diabody-unit has the orientation $V_H$-$V_H$ and the other pair of variable domains of the second single-chain diabody unit has the orientation $V_L$-$V_L$ (FIG. 4). Such antibody molecule is hexavalent and may comprise antigen binding sites for one to six different antigen specificities, in particular two or three different antigen specificities.

In certain instances the antibody, in particular Fv antibody, molecule may comprise a diabody unit in the format of a dimeric diabody unit. In such instances the antibody molecule is a dimer of two polypeptides, wherein the first pair of two juxtaposed variable domains of the diabody unit is integrated into a first polypeptide having at least six variable domains linked one after another and said first pair of juxtaposed variable domains is associated with another second pair of juxtaposed two variable domains in a second polypeptide. Preferably, the first and second polypeptides are non-covalently associated (FIGS. 2, 3, 5, 6a, 6b, 7, 8a and 8b8b). However, in some instances the first and second polypeptide may be covalently bonded, e.g. by a disulfide bond or chemical linker.

In some embodiments the first polypeptide may comprise at least six variable domains and the second polypeptide may comprise at least two variable domains (FIG. 2). In such embodiments the second polypeptide is part of the diabody unit and is, preferably non-covalently, associated with the other pair of two juxtaposed variable domains integrated into the first polypeptide. In embodiments where the first polypeptide chain consists of six variable domains and the second polypeptide consists of two variable domains the variable domains may be arranged from the N-terminus to the C-terminus of the polypeptides, for example, in the following orientations: $V_H$-$V_L$-$V_H$-$V_H$-$V_L$-$V_H$ (first polypeptide) and $V_L$-$V_L$ (second polypeptide); $V_L$-$V_H$-$V_H$-$V_H$-$V_H$-$V_L$ (first polypeptide) and $V_L$-$V_L$ (second polypeptide); $V_H$-$V_L$-$V_L$-$V_L$-$V_H$-$V_L$ (first polypeptide) and $V_H$-$V_H$ (second polypeptide); $V_L$-$V_H$-$V_L$-$V_L$-$V_H$-$V_L$ (first polypeptide) and $V_H$-$V_H$ (second polypeptide) or $V_H$-$V_L$-$V_L$-$V_L$-$V_L$-$V_H$ (first polypeptide) and $V_H$-$V_H$ (second polypeptide). Diabody units having one pair of the two variable domains in the orientation $V_H$-$V_H$ and the other pair of the two variable domains in the orientation $V_L$-$V_L$ favor the correct folding, in particular of multispecific, e.g. trispecific, antibody molecules.

Tetravalent embodiments of an antibody molecule which may comprise a first polypeptide having at least six variable domains and a second polypeptide having at least two variable domains as described in the foregoing are favorable for trispecific antibodies. Due to the different sizes of the first and second polypeptides, the polypeptides can be easily separated from the supernatant. For example, such trispecific antibodies can provide a first and a second specificity for a target cell, e.g. tumor cell, and a third specificity for an immune effector cell, e.g. T- or NK-cell. In other embodiments the trispecific antibody molecules provide a first and a second specificity for a first and a second viral antigen or viral antigen epitope and a third specificicity for an effector cell, e.g. a T- or NK-cell. In further embodiments the trispecific antibody molecule provides a first specificity for a viral antigen, a second specificity for an antigen on a target cell and a third specificity for an effector cell, e.g. a T- or NK-cell. In other instances, such trispecific antibody may have a first and a second specificity for an effector cells, e.g., NK-cell or T cell, and a third specificity for a target cell, e.g. tumor antigen on a tumor cell or viral antigen. The first and second specificity for an effector cell may be different antigens or epitopes of the same antigen on the same type of effector cells.

In some embodiments the two distal scFv units formed in the first polypeptide may have the first and the second specificity for the target cell and the diabody-unit between the two scFv units and formed with the first and second polypeptide may have specificity for an immune effector cell; i.e., from the N-terminus to the C-terminus in the first polypeptide the first and second variable domain has the first specificity for the target cell; the third and fourth variable domains have the third specificity for the immune effector cell, the fifth and sixth variable domains have the second specificity for the target cell and in the second polypeptide the first and second variable domains have the third specificity for the immune effector cell (FIG. 2). In other embodiments the two distal scFv units in the first polypeptide having six variable domains may have specificity for the immune effector cell and the two antigen binding sites formed by the diabody unit of the first polypeptide as well as the two variable domains of the second polypeptide may have two different specificities for the target cell; i.e. from the N-terminus to the C-terminus in the first polypeptide the first and the second as well as the fifth and the sixth variable domains have the third specificity for the immune effector cell, the third variable domain has the first specificity for the target cell, the fourth variable domain has the second specificity for the target cell and in the second polypeptide the first variable domain has specificity for the second specificity of the target cell and the second variable domain has the first specificity for the target cell.

In further embodiments the first polypeptide may comprise at least six variable domains and the second polypeptide may comprise four (FIGS. 6a, 6b) or six (FIG. 7) variable domains. In such embodiments the first polypeptide may comprise the first pair of variable domains of the diabody-unit and the second polypeptide may comprise the second pair of variable domains of the diabody-unit which are, preferably non-covalently, associated with one another, thereby forming two antigen binding sites between the first and second polypeptide. In embodiments where the first polypeptide chain consists of six variable domains and the second polypeptide consists of four variable domains the pair of juxtaposed variable domains of the diabody unit in the second polypeptide is linked to a scFv unit providing a further antigen binding site either N-terminally or C-terminally of the second polypeptide (FIGS. 6a, 6b). Such embodiments are pentavalent and may comprise antigen binding sites for one to five different antigen specificities, in particular two or three different antigen specificities. Diabody-units having one pair of the two variable domains in the orientation $V_H$-$V_H$ in the first polypeptide and the other pair of the two variable domains in the orientation $V_L$-$V_L$ in the second polypeptide favor the correct folding, in particular of multispecific, e.g. trispecific, antibody molecules.

Figure 3:
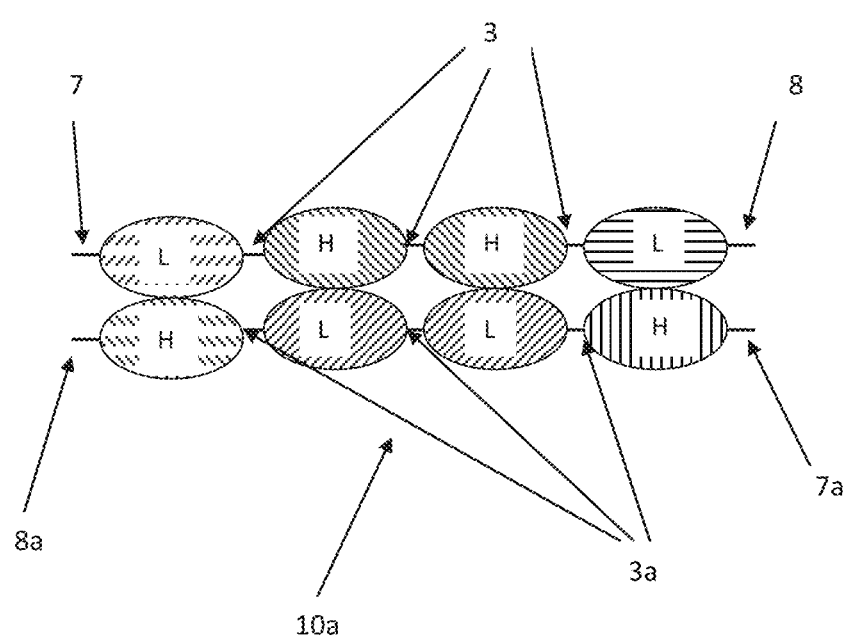
FIG. 3 shows a tetravalent, trispecific Fv antigen-binding molecule in the format of a trispecific tandem diabody consisting of a first and a second polypeptide forming a non-covalently associated heterodimer. The tandem diabody may comprise a dimeric diabody unit 1 formed by a pair of centrally located $V_H$-$V_H$ domains in the first polypeptide with a pair of centrally located $V_L$-$V_L$ domains in the second polypeptide. The variable domains in the first and second polypeptide are linked one after another by short peptide linkers 3, 3a from the N-terminus 7 to the C-terminus 8 in the orientation $V_L$-$V_H$-$V_H$-$V_L$ in the first polypeptide and from the N-terminus 7a to the C-terminus 8a in the orientation $V_H$-$V_L$-$V_L$-$V_H$ in the second polypeptide. The N-terminally and C-terminally located variable domains have antigen binding sites with different specificities at the N-terminus and the C-terminus and the centrally diabody unit 1 has two antigen binding sites for the same specificity.
Figure 8A:
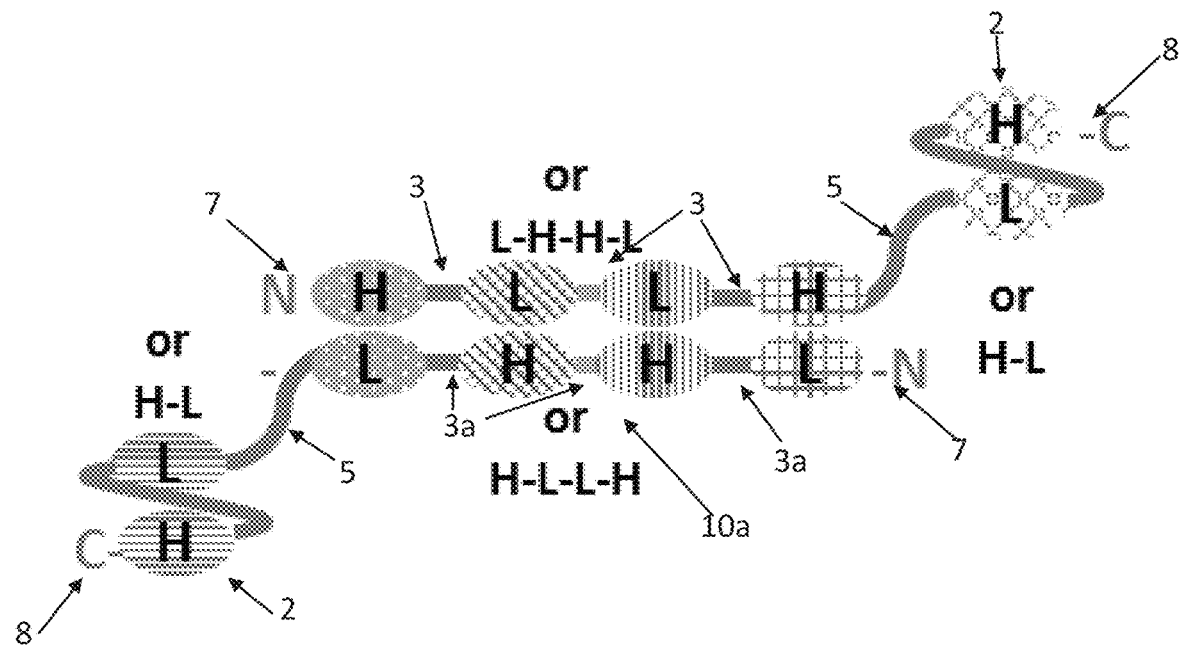
FIGS. 8a-8b shows a hexavalent Fv antigen-binding molecule which may comprise a tandem diabody unit consisting of a first and a second polypeptide forming a non-covalently associated dimer. The tandem diabody may comprise a dimeric diabody unit 10a formed by a pair of centrally located variable domains in the first polypeptide with a pair of centrally located variable domains in the second polypeptide. The variable domains in the first and second polypeptide are linked one after another by short peptide linkers 3, 3a from the N-terminus 7 to the C-terminus 8 in each polypeptide. The domain orientation is only an example and other arrangements for each juxtaposed pair of variable domais are possible as indicated in the Figure. Each of the first and second polypeptide may comprise a scFv unit 2 linked by a linker 5 to the tandem diabody unit. A) scFv units 2 linked C-terminally of first and second polypeptide. B) scFv units 2 linked N-terminally of first and second polypeptide.

In another embodiments where the first polypeptide chain consists of six variable domains and the second polypeptide consists of four variable domains the pair of juxtaposed variable domains of the diabody unit in the second polypeptide is linked N-terminally and C-terminally to scFv units providing two further antigen binding sites (FIG. 7). Such embodiments are hexavalent and may comprise antigen binding sites for one to six different antigen specificities, in particular two or three different antigen specificities. In particular embodiments the diabody unit has one pair of variable domains in the orientation $V_H$-$V_H$ in the first polypeptide and the other pair of variable domains in the orientation $V_L$-$V_L$ in the second polypeptide. In further alternative embodiments the multivalent, for example trispecific Fv antibody molecule may comprise more than one dimeric diabody units. In such alternative embodiments the first polypeptide may comprise at least six variable domains and the second polypeptide may comprise four (FIG. 3) or six (FIGS. 8a, 8b) variable domains. In embodiments where the first polypeptide may comprise at least six variable domains and the second polypeptide may comprise four variable domains, the four juxtaposed variable domains of the second polypeptide are associated with the corresponding four juxtaposed variable domains integrated into the first polypeptide thereby forming a tandem of two juxtaposed diabody-units. The remaining at least two further variable domains of the first polypeptide are located distally from the tandem diabody units and form a scFv unit (FIGS. 8a, 9b). In other embodiments where the first polypeptide may comprise six variable domains and the second polypeptide may comprise six variable domains, the six variable domains of the first polypeptide are associated with the corresponding six variable domains of the second polypeptide thereby forming a triple of juxtaposed diabody-units (FIG. 3). The latter embodiment consisting of a first and second polypeptide, wherein each polypeptide may comprise six variable domains has the advantage that it can provide a trispecific antibody in the format of a homodimer, i.e. two identical polypeptides are associated with one another and provide bivalent binding for each of the three antigen specificities.

In certain instances a tetravalent, trispecific Fv antibody is provided by a tandem diabody. Such trispecific Fv antibody molecule consists of a first and a second polypeptide, wherein each polypeptide may comprise four variable domains linked one after another. In such Fv antibody molecule the linker length is such that it precludes intramolecular pairing of the variable domains so that the molecule cannot fold back upon itself, but is forced to pair, i.e. associate, with the complementary domains of another polypeptide. The domains are arranged such that the corresponding $V_H$ and $V_L$ domains associate with each other during this dimerization. Despite the absence of intermolecular covalent bonds the dimer is highly stable once formed, remains intact and does not revert back to the monomeric form. In some embodiments the trispecific Fv antibody molecule may comprise a dimeric diabody unit, wherein one pair of two juxtaposed variable domains has the orientation $V_H$-$V_H$ and the other pair of two juxtaposed variable domains has the orientation $V_L$-$V_L$. Such orientation of the variable domains in the diabody unit facilitates the correct association of the two trispecific polypeptides. In particular, such orientation enables trispecific Fv antibody molecules in the format of a tandem diabody, because it is a heterodimer of two different polypeptides. Hence, such orientation favorably enables the correct heterodimerization of the trispecific tandem diabody. Hence, in some embodiments the trispecific Fv antibody molecule is a tandem diabody (FIG. 3). In such trispecific tandem diabodies the variable domains of the first and second polypeptide may be arranged from the N-terminus to the C-terminus of the polypeptides, for example, in the following orientations: $V_L$-$V_H$-$V_H$-$V_L$ (first polypeptide) and $V_H$-$V_L$-$V_L$-$V_H$ (second polypeptide) or vice versa (FIG. 3). Such trispecific antibodies in the format of a tandem diabody can provide a first and a second specificity for a target cell, e.g. tumor cell, and a third specificity for an immune effector cell, e.g. T- or NK-cell. In other instances, such trispecific antibody may have two specificities for different antigens on the effector cells and a third specificity for an antigen on a tumor cell. In some embodiments the variable domains located externally in the polypeptides may have the first and the second specificities for the target cell and the two variable domains centrally located in the polypeptide between the externally located variable domains have the third specificity for an immune effector cell; i.e., from the N-terminus to the C-terminus in the first polypeptide the first variable domain has the first specificity for the target cell; the second and the third variable domains have the third specificity for the immune effector cell, the fourth variable domain has the second specificity for the target cell, and in the second polypeptide the first variable domain has the second specificity for the target cell, the second and the third variable domains have the third specificity for the immune effector cell and the fourth variable domain has the first specificity for the target cell (FIG. 3). In other embodiments the variable domains located externally in the polypeptides may have the third specificity for an immune effector cell and the two variable domains centrally located in the polypeptide between the externally located variable domains may have the first and the second specificities for the target cell; i.e., from the N-terminus to the C-terminus in the first polypeptide the first variable domain has the third epitope specificity for the immune effector cell; the second variable domain has the first specificity for the target cell, the third variable domain has the second specificity for the target cell, the fourth variable domain has the third specificity for the immune effector cell, and in the second polypeptide the first variable domain has the third specificity for the immune effector cell, the second variable domain has the second specificity for the target cell, the third variable domain has the first specificity for the target cell and the fourth variable domain has the third specificity for the immune effector cell. In other embodiments the variable domains having the third specificity for the immune effector cell are laterally located in the antibody molecule; i.e., from the N-terminus to the C-terminus in the first polypeptide the first and second variable domains have the third specificity for the immune effector cell; the third variable domain has the first specificity for the target cell, the fourth variable domain has the second specificity for the target cell, and in the second polypeptide the first variable domain has the second specificity for the target cell, the second variable domain has the first specificity for the target cell and the third and fourth variable domains have the third specificity for the immune effector cell.

In further embodiments the tandem diabody is conjugated to at least one further antigen binding domain, in particular at least one scFv-unit N-terminally or C-terminally of the polypeptide. In preferred embodiments the tandem diabody is conjugated by a peptide linker to the at least one scFv-unit. In particular such antibody molecule consists of a first and a second polypeptide, wherein both polypeptides consist of six variable domains and each of the first polypeptide and the second polypeptide may comprise a scFv-unit either N-terminally of each polypeptide (FIG. 8b) or C-terminally of each polypeptide (FIG. 8a). Such antibody molecules are hexavalent and may comprise antigen binding sites for one to six different antigen specificities, in particular two or three different antigen specificities. In particular embodiments diabody-unit, centrally located within the antibody molecule, has one pair of variable domains in the orientation $V_H$-$V_H$ in the first polypeptide and the other pair of variable domains in the orientation $V_L$-$V_L$ in the second polypeptide. In certain instances the multivalent antibody molecule, in particular Fv antibody molecule described herein, is an at least trispecific and at least tetravalent antibody molecule. Such antibody molecule may comprise at least two antigen-binding sites having specificity for the same antigen epitope. Thereby the avidity is increased, i.e. the strength of interaction between the antigen epitope and antigen-binding molecule. The avidity of trispecific antibody molecules may be further increased by the pentavalent and hexavalent embodiments of the invention. Pentavalent molecules may offer at least two binding sites for two of the three epitope specificities of the trispecific antibody and hexavalent embodiments may offer two antigen-binding sites for each of the three epitope specificities. Alternatively, the multispecificity, i.e, number of specificitisspecificities, may be increased by tetravalent, pentavalent and hexavalent embodiments. For example, the antibody molecules may be tetraspecific. Advantages of the higher avidity are increased stability of interaction and retention on the target. For example, if the target is a cytotoxic immune effector cell such as a T-cell or a NK-cell, the higher avidity can result in an increased cytotoxic potential of the antibody molecule. In another example, if the target is a tumor cell, the higher avidity improves the retention time on the target and reduces the off-rates from the target. In a certain embodiment of the invention, the trispecific and tetravalent Fv antibody molecule may comprise first and second antigen-binding sites specific for two different antigen epitopes of the same kind of tumor cell and third and fourth antigen binding sites specific for an antigen epitope on an immune effector cell, such as a T-cell or a NK-cell. Such an antibody molecule leads to an increased specificity as well as avidity for a particular kind of tumor cell and to an increased avidity for activating or inhibiting a receptor on the immune effector cell which results in an advantageously increased specific cytotoxic potential of the antigen-binding molecule. The binding to two distinct tumor antigen epitopes leads to an increase in targeting specificity and to an extension of the therapeutic window by reducing off-target toxicities. Hence, the present invention provides multispecific antibody molecules, which favorably increased avidity and/or biological activity due to providing at least two antigen-binding sites for at least one of the epitope specificities, for example two binding sites for one, two or three epitope specificities, i.e. targets.

Importantly, despite the structural complexity, such multispecific, e.g. trispecific and multivalent, e.g., tetravalent, antibody molecule according to the invention is stable.

In other instances, such multispecific, e.g. trispecific, antibody may have two specificities for different antigens on the effector cell, e.g. NK-cell or T-cell, and a third specificity for an antigen on a tumor cell.

Therefore, the antibody molecule according to the invention can be utilized in different ways for redirecting the cytotoxic potential of immune effector cells to destroy tumor cells or infectious agents, such as, for example, virally infected cells. In some embodiments the multispecific, e.g., trispecific antibody molecule may bind to two different antigen epitopes on a target. For example, the two different epitopes may be on the same antigen to prevent escape mutants or to enhance efficacy or the two epitopes may be on two different antigens of the target. In other embodiments the trispecific antibody molecule may bind to two different antigen epitopes on immune effector cells. For example, a first antigen-binding site has specificity for an activating receptor, e.g. CD16, CD16A or CD3, and a second antigen-binding site has specificity for a co-stimulatory receptor, e.g, CD137, OX-40 or CD28. In another example, a first antigen-binding site has specificity for CD16 or CD16A and a second antigen-binding site for another activating receptor on NK-cells, e.g. NKG2D, DNAM, NCRs).

In another embodiment the trispecific, in particular Fv, antibody molecule has a first antigen-binding site having specificity for an antigen epitope on a tumor cell, a second antigen-binding site having specificity for an antigen epitope on an immune effector cell and a third antigen-binding site having specificity for an antigen epitope on a soluble protein selected from the group of growth factors, cytokines, chemokines, mitogens and albumins. Examples of such a soluble protein are IL-6, BAFF, APRIL, TGF-beta, IL-10, VEGF-A, TGF-alpha, EGF, HB-EGF, Heregulins, angiopoetin-2 and human serum albumin (HSA).

In an alternative embodiment the antibody molecule has one antigen-binding site having specificity for an antigen epitope of an antigen present on one type of cell and three antigen-binding sites having specificities of antigen epitopes on one or more other types of cells.

"Effector cells" are cells of the immune system which can stimulate or trigger cytotoxicity, phagocytosis, antigen presentation or cytokine release. Such effector cells are, for example but not limited to, T-cells, natural killer (NK)-cells, gamma delta (gd) T-cells, natural killer T (NKT)-cells, granulocytes, monocytes, macrophages, dendritic cells, innate lymphoid cells (ILC) and antigen-presenting cells. Examples of suitable specificities for effector cells include but are not limited to CD2, CD3 and CD3 subunits such as CD3ε, CD5, CD28 and other components of the T-cell receptor (TCR) or CD134 (OX40) for T-cells; CD16A, CD25, CD38, CD44, CD56, CD69, CD94, CD335 (NKp46), CD336 (NKp44), CD337 (NKp30), NKp80, NKG2A, NKG2C and NKG2D, DNAM, NCRs for NK-cells; CD18, CD64 and CD89 for granulocytes; CD18, CD32, CD47, CD64, CD89 and mannose receptor for monocytes and macrophages; CD64 and mannose receptor for dendritic cells; as well as CD35. In certain embodiments of the invention those specificities, i.e. cell surface molecules, of effector cells are suitable for mediating cell killing upon binding of a multispecific, e.g., trispecific, antibody molecule to such cell surface molecule and, thereby, inducing cytolysis or apoptosis.

CD3 antigen is a component of the T-cell receptor complex on T-cells. In the case where specificity for an effector cell is CD3, the binding of the antigen-binding molecule according to the invention to CD3 triggers the cytotoxic activity of T-cells. By binding of the antibody molecule to CD3 and to a target cell, e.g. tumor cell, cell lysis of the target cell may be induced.

The CD16A (FcγRIIIA) antigen is a receptor expressed on the surface of NK-cells. NK-cells possess an inherent cytoloytic activity and by binding of the antibody molecule according to the invention to CD16 or CD16A the cytotoxic activity of NK-cell towards the target can be triggered.

"Target" is the site on which the antigen epitope is located and to which the antibody molecule should bind to. Examples of targets are soluble agents, antigens on cells, infectious agents such as viral or bacterial antigens, for example derived from dengue virus, herpes simplex, influenza virus, HIV, HCV, CMV or antigens on cells which facilitate the entry of viruses and bacteria or cells, for example neurons, displaying antigens, or cells carrying autoimmune targets such as IL-2/IL2R, an autoimmune marker or an autoimmune antigen or tumor cells. In embodiments, wherein at least one of the antigen-binding sites has specificity for an effector cell, the target can be a tumor cell to which the effector cell should be redirected to induce or trigger the respective biological, e.g. immune, response.

Suitable specificities for tumor cells may be tumor antigens and cell surface antigens on the respective tumor cell, for example specific tumor markers. The term "tumor antigen" as used herein may comprise tumor associated antigen (TAA) and tumor specific antigen (TSA). A "tumor associated antigen" (TAA) as used herein refers to a protein which is present on tumor cells, and on normal cells during fetal life (onco-fetal antigens), and after birth in selected organs, but at much lower concentration than on tumor cells. A TAA may also be present in the stroma in the vicinity of the tumor cell but expressed at lower amounts in the stroma elsewhere in the body. In contrast, the term "tumor specific antigen" (TSA) refers to a protein expressed by tumor cells. The term "cell surface antigen" refers to a molecule any antigen or fragment thereof capable of being recognized by an antibody on the surface of a cell.

Examples of specificities for tumor cells include but are not limited to CD19, CD20, CD26, CD29, CD30, CD33, CD52, CD200, CD267, EGFR, EGFR2, EGFR3, EGFRvIII, HER2, HER3, IGFR, IGF-1R, Ep-CAM, PLAP, Thomsen-Friedenreich (TF) antigen, TNFRSF17, gpA33, MUC-1 (mucin), IGFR, CD5, IL4-R alpha, IL13-R, FcεRI, MHC class I/peptide complexes and IgE.

Antibody molecules according to the invention, wherein the tumor specificity is towards CD19 antigen may be used for immunotherapy of B-cell malignancies, because the CD19 antigen is expressed on virtually all B-lineage malignancies from lymphoblastic leukemia (ALL) to non-Hodgkin's lymphoma (NHL).

Antibody molecules according to the invention wherein the tumor specificity is towards CD30 may be particularly useful in treating Hodgkin's disease and T-cell lymphomas.

Antibody molecules according to the invention wherein the tumor specificity is towards epidermal growth factor receptor (EGFR) or EGFRvIII mutant may be used in treating tumors of glioma, breast, ovary, prostate, lung, head and neck; liver diseases, such as, for example, hepatocellular cancer, liver cirrhosis or chronic hepatitis, For increasing serum-half life of the antibody molecule according to the invention in the body, the antibody molecule, if desired, may be fused to albumin, e.g. human serum albumin (HSA), or pegylated, sialylated, pasylated or glycosylated (see, for example, Stork et al., 2008, J. Biol. Chem., 283:7804-7812). In some embodiments the antibody molecule is at least trispecific and may comprise at least one, e.g. one or two, antigen-binding sites having specificity for albumin, e.g. HSA. Such at least trispecific antibody molecule can be, for example, a tetravalent, pentavalent or hexavalent antibody molecule.

Variable domains having specificity for epitopes on target cells or effector cells can be obtained by selecting variable fragments (Fvs) that are specific for antigens of interest. This can be accomplished, for example, by screening single-chain Fv (scFv) phage display libraries or through hybridoma technology. For instance, IgM-based phage display libraries of human scFv sequences can be subjected to several rounds of in vitro selection to enrich for binders specific to the desired antigen. Affinities of selected scFvs may be further increased by affinity maturation.

In some embodiments of the invention at least one, preferably all, antibody variable domains are fully human, humanized or chimeric domains. Humanized antibodies can be produced by well-established methods such as, for example CDR-grafting (see, for example, Antibody engineering: methods and protocols/edited by Benny K. C. Lo; Benny K. C. II Series: Methods in molecular biology (Totowa, N.J.). Thus, a skilled person is readily able to make a humanized or fully human version of antigen-binding molecule and variable domains from non-human, e.g. murine or non-primate, sources with the standard molecular biological techniques known in the art for reducing the immunogenicity and improving the efficiency of the antigen-binding molecule in a human immune system. In a preferred embodiment of the invention all antibody variable domains are humanized or fully human; most preferred, the antibody molecule according to the invention is humanized or fully human. The term "Fully human" as used herein means that the amino acid sequences of the variable domains and the peptides linking the variable domains in the polypeptide originate or can be found in humans. In certain embodiments of the invention the variable domains may be human or humanized but not the peptides linking the antibody variable domains.

A skilled person will readily be able without undue burden to construct and obtain the antibody molecule described herein by utilizing established techniques and standard methods known in the art, see for example Sambrook, Molecular Cloning A Laboratory Manual, Cold Spring Harbor Laboratory (1989) N.Y.; The Protein Protocols Handbook, edited by John M. Walker, Humana Press Inc. (2002); or Antibody engineering: methods and protocols/edited by Benny K. C. Lo; Benny K. C. II Series: Methods in molecular biology (Totowa, N.J.); Antibody Engineering/edited by Roland E. Kontermann and Stefan Dübel, Springer Verlag Berlin Heidelberg (2010)).

The antibody molecule according to any one of the embodiments described herein may be produced by expressing polynucleotides encoding the individual polypeptide chains which form the antibody molecule. Therefore, further embodiments of the invention are polynucleotides, e.g. DNA or RNA, encoding the polypeptides of the antibody molecule as described herein above.

The polynucleotides may be constructed by methods known to the skilled person, e.g. by combining the genes encoding the antibody variable domains either separated by peptide linkers or directly linked by a peptide bond of the polypeptides, into a genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotides in the respective host cell.

The polynucleotides may be inserted into vectors, preferably expression vectors, which represent a further embodiment of the invention. These recombinant vectors can be constructed according to methods well known to the person skilled in the art.

A variety of expression vector/host systems may be utilized to contain and express the polynucleotides encoding the polypeptide chains of the present invention. Examples for expression vectors for expression in *E. coli* is pSKK (LeGall et al., J Immunol Methods. (2004) 285(1): 111-27) or pcDNA5 (Invitrogen) for the expression in mammal cells.

Thus, the antibody molecule as described herein may be produced by introducing a vector encoding the polypeptides as described above into a host cell and culturing said host cell under conditions whereby the polypeptides are expressed, may be isolated and, optionally, further purified.

In a further embodiment of the invention compositions, e.g., pharmaceutical compositions, which may comprise an antibody molecule as described herein above and at least one further component are provided.

In further embodiments the antibody molecules are for use as a medicament or diagnostic. In particular, the antibody molecules are for use in an immunotherapy. For example, the antibody molecules are for use in the treatment of a tumor, viral or neurodegenerative disease. Therefore, the invention further may comprise a method of treating an individual by an immunotherapy, in particular the individual is suffering from a diseases selected from a tumor, viral or neurodegenerative diseases which may comprise the step of administering the antibody molecule according to the invention.

The invention further provides a method wherein the antibody molecule, in particular, a composition which may comprise an antibody molecule as described herein above and at least one further component is administered in an effective dose to a subject, e.g., patient, for the treatment of cancer (e.g. non-Hodgkin's lymphoma; chronic lymphocytic leukaemia). The antigen-binding molecule according to the invention can be for use as a medicament.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The examples below further illustrate the invention without limiting the scope of the invention.

Example 1

Cloning of DNA Expression Constructs Encoding Tri-Specific Fv Antigen-Binding Molecules For expression of tri-specific constructs in CHO cells, coding sequences of all molecules were cloned as single-gene or double gene constructs into an accordingly modified mammalian expression system derived from the pcDNA5/FRT vector. A two promoter vector was used for the cloning and the expression of two gene constructs (heterodimeric trispecfic-constructs). For the trispecific one gene construct the normal pcDNA5/FRT expression vector was used. In brief, gene sequences encoding $V_H$ and $V_L$ domains separated by different linkers (long and short linkers) were synthesized by Life Technologies GeneArt (Regensburg, Germany) and subcloned. The resulting constructs are digested via different restriction enzymes (BamHI, HindIII, XhoI, EcoRV, PacI) or the different $V_H/V_L$ effector and target binding domains are amplified via PCR with corresponding primers. Afterwards the different overlapping DNA-fragments and the linearized backbone 2 promoter vector or pcDNA5/FRT vector are joined together via Gibson Assembly in one isothermal reaction. All expression constructs were designed to contain coding sequences for an N-terminal signal peptide and a C-terminal hexahistidine (6×His)-tag for the first gene cassette or a C-terminal FLAG-tag for the second gene cassette to facilitate antibody secretion and purification, respectively. Sequences of all constructs were confirmed by DNA sequencing at GATC (Konstanz, Germany) using the primer pair 5'-AGAGCTCGTTTAGTGAACCG-3' and 5'-TCATGTCTGGATCCGGCCTTG-3' for gene cassette 1 or 5'-GCCTGGAGACGCCATCC-3' and 5'-GCAGAATTCCACCACACTGG-3' for gene cassette 2.

Host Cell Culture

Flp-In CHO cells (Life Technologies), a derivative of CHO-K1 Chinese Hamster ovary cells (ATCC, CCL-61) (Kao and Puck, 1968), were cultured in Ham's F-12 Nutrient Mix supplemented with L-Glutamine, 10% FCS and 100 µg/mL Zeocin. Adherent cells were detached with 0.25% Trypsin-EDTA and subcultured according to standard cell culture protocols provided by Life Technologies.

For adaptation to growth in suspension, cells were detached from tissue culture flasks and placed in serum-free HyClone CDM4 CHO medium for subsequent incubation in shake flasks at 37° C., 5% $CO_2$ and 120 rpm. The standard medium for the culture of suspension-adapted Flp-In CHO Host cells was HyClone CDM4 CHO supplemented with L-Glutamine, HT Supplement, Penicillin/Streptomycin and 100 µg/mL Zeocin. Suspension-adapted cells were cryopreserved in medium with 10% DMSO and tested negative for *Mycoplasma* using MycoAlert *Mycoplasma* detection Kit (Lonza).

Generation of Stably Transfected Cell Pools

Recombinant Flp-In CHO cell lines stably expressing secreted single-gene or double-gene tri-specific antibodies were generated by transfection of suspension-adapted host cells. For this, cells were placed in standard medium without Zeocin one day prior to co-transfection with expression plasmids (2.5 µg) encoding the protein of interest (pcDNA5/

FRT) and the Flp recombinase (pOG44, Life Technologies) using Polyethylenimine (PEI). In brief, vector DNA and transfection reagent were mixed at a DNA:PEI ratio of 1:3 (µg/µg) in a total of 100 µL OptiMEM I medium and incubated for 10 minutes before addition to 2·10⁶ Flp-In CHO cells suspended in 1 mL of CHO—S-SFMII medium (Life Technologies). Following 24 h incubation, selection for stably transfected cells was started by addition of 500 µg/mL Hygromycin B subsequent to diluting cultures to a density of 0.1·10⁶ viable cells/mL in CHO—S-SFMII medium and seeding in T75 culture flasks. Flp recombinase mediates the insertion of the expression constructs into the Flp-In CHO cell's genome at the integrated FRT site through site-specific DNA recombination (O' Gorman et al 1991). During selection viable cell densities were measured twice a week, and cells were centrifuged and resuspended in fresh selection medium at a maximal density of 0.1·10⁶ viable cells/mL. Cell pools stably expressing recombinant protein products were recovered after 2-3 weeks of selection at which point cells were transferred to standard culture medium in shake flasks. Expression of recombinant secreted proteins was confirmed by protein gel electrophoresis of cell culture supernatants using Criterion Stain-Free (Bio-Rad) technology. Stable cell pools were cryopreserved in medium containing 50% ProFreeze (Lonza) and 7.5% DMSO.

Production of Recombinant Protein in Fed-Batch CHO Cell Suspension Cultures

Recombinant proteins were produced in 10-day fed-batch cultures of stably transfected CHO cell lines by secretion into the cell culture supernatant. For this, cell pools stably expressing tri-specific antibodies were seeded at starting densities of 6·10⁵ cells/mL in standard culture medium in polycarbonate Erlenmeyer flasks with gas permeable caps (Corning) and incubated at 37° C. and 5% $CO_2$ with agitation at 140 rpm. During fed-batch culture, media were supplemented with 40 mL/L ActiCHO Feed A (GE Healthcare) and 4 mL/L ActiCHO Feed B (GE Healthcare) on day 0 (starting day), and with double amounts on day 3, 5, and 7. Cell culture supernatants were harvested after 10 days at culture viabilities of typically >75%. Samples were collected from the production cultures every other day prior to feeding and cell density and viability was assessed. On the day of harvest, cell culture supernatants were cleared by centrifugation and vacuum filtration (0.22 µm) using Millipore Express PLUS Membrane Filters (Millipore) before further use.

Purification of Tri-Specific Fv Antibodies

Tri-specific antibodies were purified from clarified CHO cell culture supernatants in a two-step procedure comprising IMAC and preparative SEC. If necessary, a third chromatographic step (FLAG-affinity chromatography) was applied for further polishing. For IMAC the clarified supernatant was loaded on a HisTrap Sepharose column. After washing with Tris/NaCl buffer pH 7.5 protein was eluted in a three-step gradient with 15 mM, 125 mM, and 500 mM imidazole, respectively. The purity of fractions was analyzed using SE-HPLC and SDS-PAGE. Fractions exhibiting acceptable purity were pooled and subjected to preparative gel filtration using a Superdex 200 prep grade column. FLAG affinity chromatography was in some cases for further polishing. Therefore, the protein was loaded on the FLAG affinity column, washed with PBS and eluted using glycine/HCl buffer at pH 3.5. Eluate fractions containing purified tri-specific antibodies were pooled, dialyzed against 10 mM sodium acetate pH 5.0, and concentrated by ultrafiltration to a typical concentration of approx. 1 mg/mL. Purity and homogeneity (approx. 90%) of the final samples were assessed by SDS-PAGE under reducing and/or non-reducing conditions, followed by immunoblotting with His-tag as well as FLAG-Tag specific antibodies, as well as by analytical SE-HPLC. Purified proteins were stored as aliquots at −80° C. until further use.

Examples of biophysical data for trispecific Fv antibody molecules described in Example 3; aTriFlex_101 (Example 3a)), aTriFlex_102 (Example 3b)), aTriFlex_103 (Example 3c)) and aTriFlex_104 (Example 3d) is shown in Table 1. The SDS-PAGESs of the fractions is shown in FIG. 11: All trispecific, tetravalent Fv antibody molecules were expressed with acceptable titers, independent of the domain order, e.g., $V_H$-$V_L$-$V_H$-$V_H$-$V_L$-$V_H$ (aTriFlex_101) or $V_L$-$V_H$-$V_H$-$V_H$-$V_H$-$V_L$ (aTriFlex_102). Thermal as well as storage stability of the trispecific, tetravalent Fv antibody molecules is very good and comparable.

TABLE 1

Biophysical data of trispecific Fv antibody molecules

| Name | Approx. Expression Titer [mg/L] | Purification (IMAC/FLAG/SEC) | % Purity (SE-HPLC) | $T_M$ (DSF) [° C.] | % Purity T = 7 d; 5° C. (SE-HPLC) | % Purity T = 7 d; 25° C. (SE-HPLC) | % Purity 3 × FT (SE-HPLC) |
|---|---|---|---|---|---|---|---|
| aTriFlex_101 | 135 | IMAC/SEC | 92.2 | 46.7 | 91.2 | 94.9 | 69.7 |
| aTriFlex_102 | 103 | IMAC/SEC/FLAG | 94.7 | 52.7 | 94.8 | 95.5 | 92.5 |
| aTriFlex_103 | 130 | IMAC/SEC | 94.8 | 47.5 | 94.7 | 95.5 | 86.4 |
| aTriFlex_104 | 125 | IMAC/SEC | 87.8 | 48.7 | 92.3 | 93.8 | 77.8 |

Example 2

Manufacturing of Trispecific Antibody Molecule with Different Domain Orders of the Diabody Unit Four different Fv antibody molecules in the format according to FIG. 2 have been constructed as described in Example 1 which have different domain arrangements of the two pairs of variable domains in the diabody unit (N→C-terminus). The variable domains of the diabody unit are shown in bold letters in tables below:

aTriFlex_138: $V_H$-$V_L$/$V_H$-$V_L$ diabody unit:

| Polypeptide | SEQ ID NO | Domain Specificities (N -> C) | Domain Order (N -> C) |
|---|---|---|---|
| 1 | 32 | CD30-CD30-CD16-EGFRvIII-CD30-CD30-His | VH-VL-VH-VL-VH-VL |
| 2 | 33 | EGFRvIII-CD16A-FLAG | VH-VL | aTriFlex_139: $V_L$-$V_H$/$V_L$-$V_H$ diabody unit:

| Polypeptide | SEQ ID NO | Domain Specificities (N -> C) | Domain Order (N -> C) |
|---|---|---|---|
| 1 | 30 | CD30-CD30-CD16-EGFRvIII-CD30-CD30-His | VH-VL-VL-VH-VH-VL |
| 2 | 31 | EGFRvIII-CD16A-FLAG | VL-VH | aTriFlex_140: $V_L$-$V_L$/$V_H$-$V_H$ diabody unit:

| Polypeptide | SEQ ID NO | Domain Specificities (N -> C) | Domain Order (N -> C) |
|---|---|---|---|
| 1 | 36 | CD30-CD30-CD16-EGFRvIII-CD30-CD30-His | VH-VL-VL-VL-VH-VL |
| 2 | 37 | EGFRvIII-CD16A-FLAG | VH-VH | aTriFlex_142: $V_H$-$V_H$/$V_L$-$V_L$ diabody unit:

| Polypeptide | SEQ ID NO | Domain Specificities (N -> C) | Domain Order (N -> C) |
|---|---|---|---|
| 1 | 34 | CD30-CD30-CD16-EGFRvIII-CD30-CD30-His | VH-VL-VH-VH-VH-VL |
| 2 | 35 | EGFRvIII-CD16A-FLAG | VL-VL |

Figure 9A:
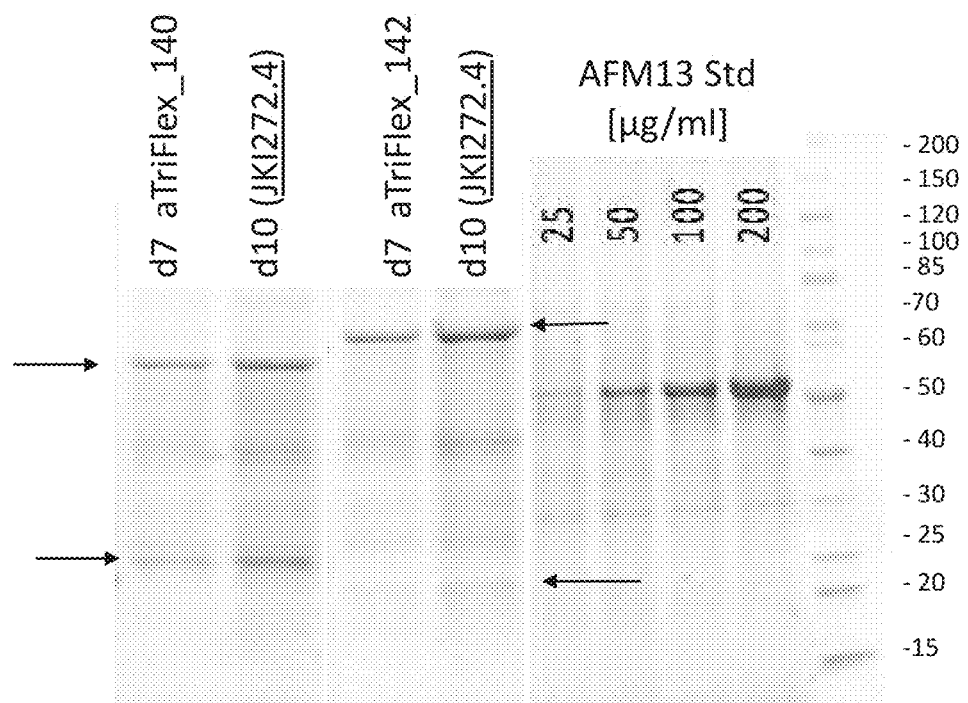
FIGS. 9a-9c shows SDS-PAGE analysis of aTriFlex-products. Long and short polypeptides are well expressed (arrows). a) aTriFlex_140 and aTriFlex_142, b) aTriFlex_138 and c) aTriFlex_139.
Figure 9B:
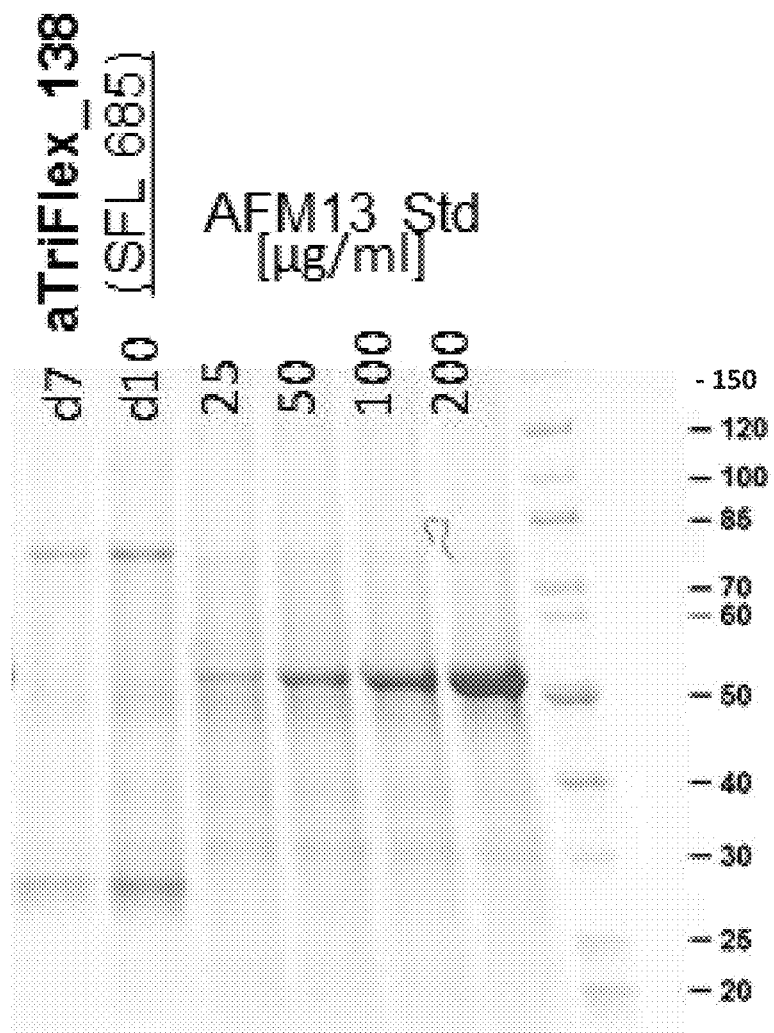
Figure 9C:
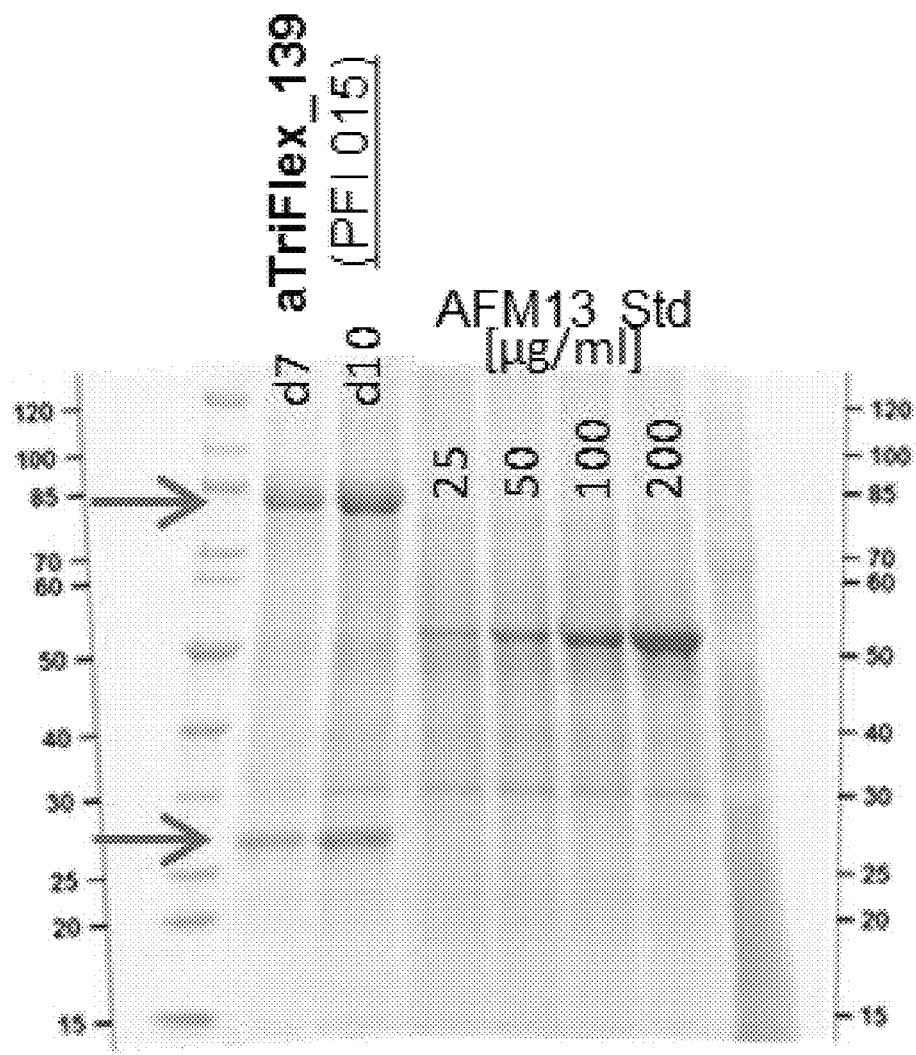

The Fv antibody molecules have been expressed in CHO cells and SDS-PAGE analysis of production cell culture supernatants show that the long polypeptides 1 and the short polypeptides 2 are well expressed and run as separate bands under denaturating conditions (FIGS. 9a, 9b, 9c).

Figure 10A:
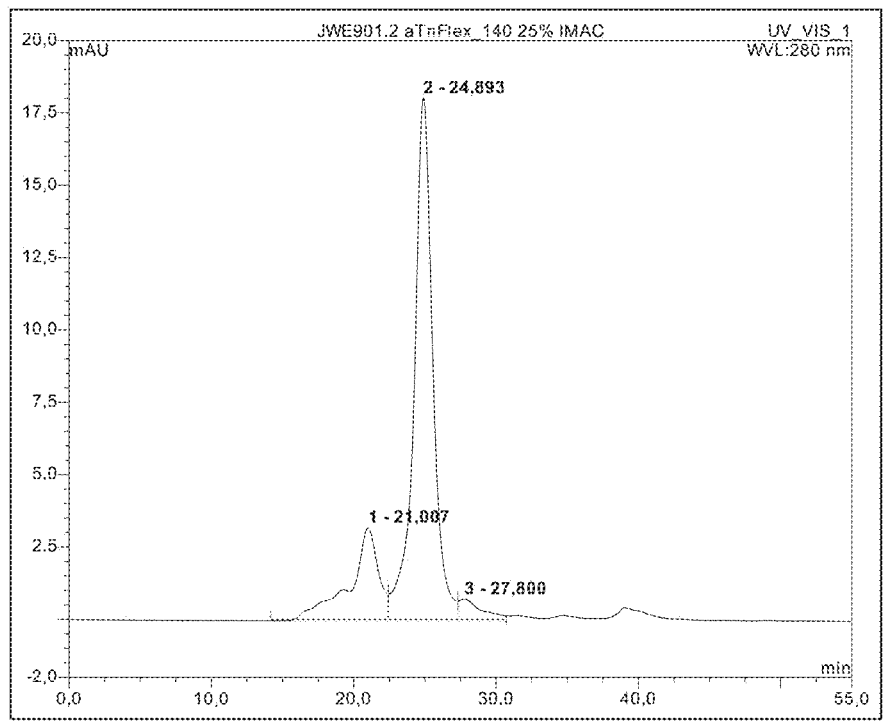
FIGS. 10a-10d shows IMAC purification of aTriFlex-products: a) aTriFlex_140, b) aTriFlex_138 and c) and aTriFlex_142 and d) aTriFlex_139.
Figure 10B:
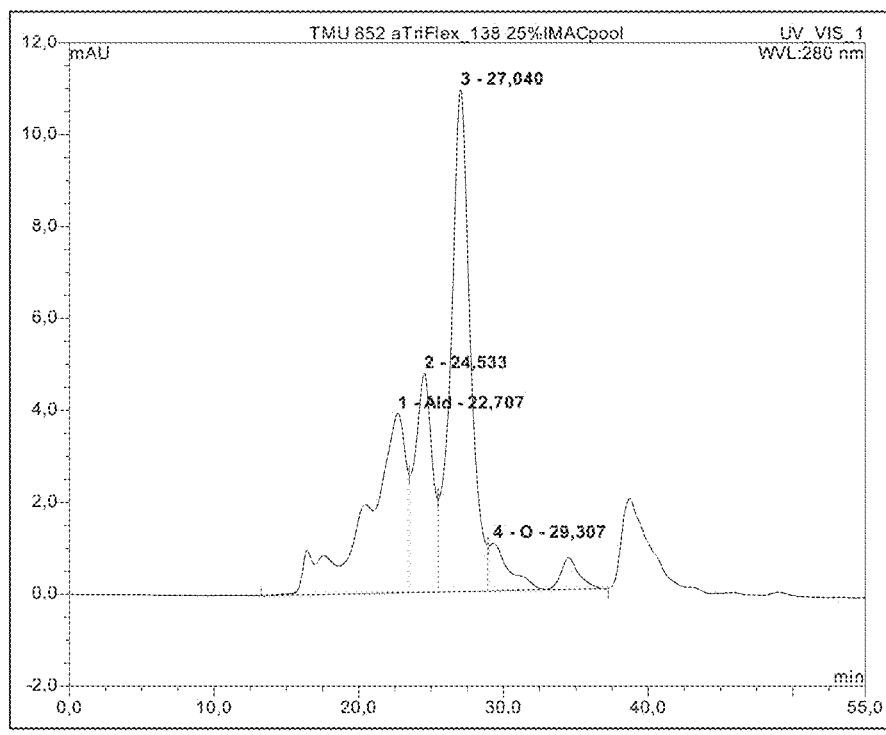
Figure 10C:
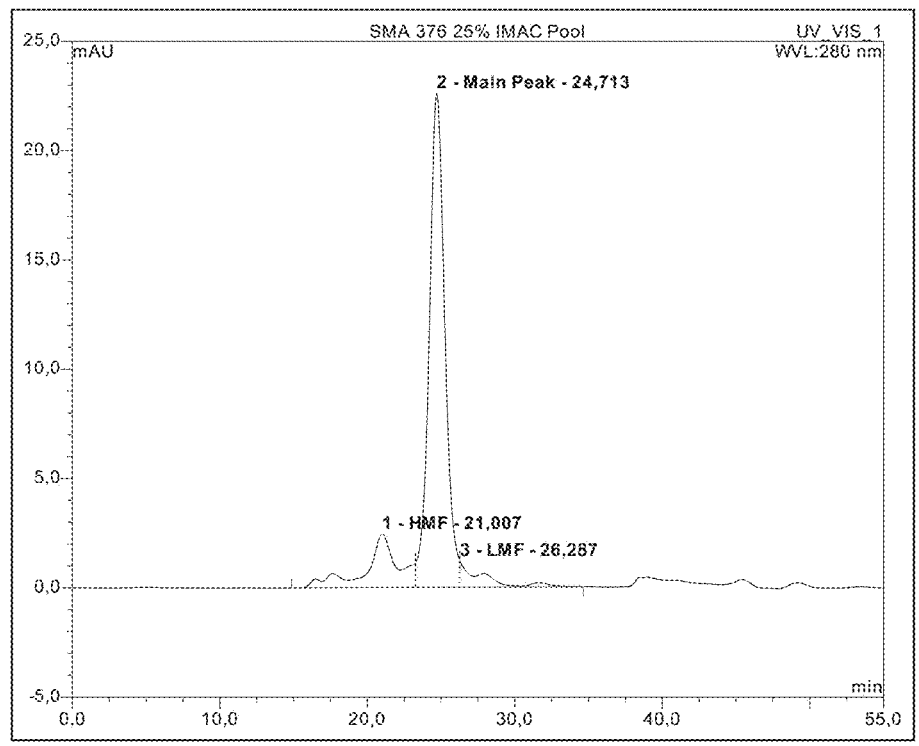
Figure 10D:
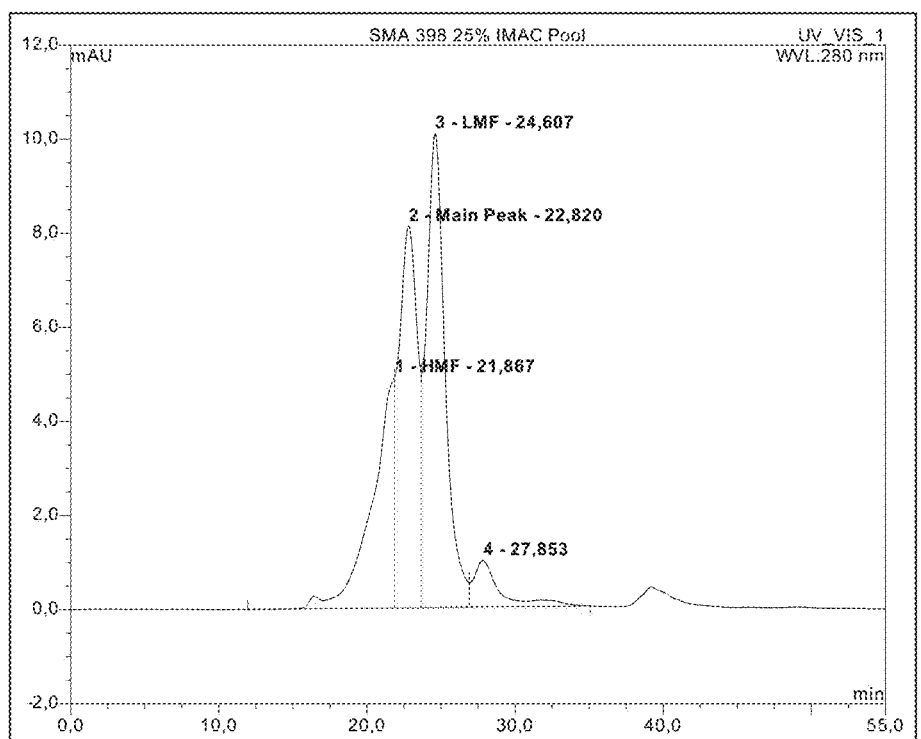
Figure 11A:
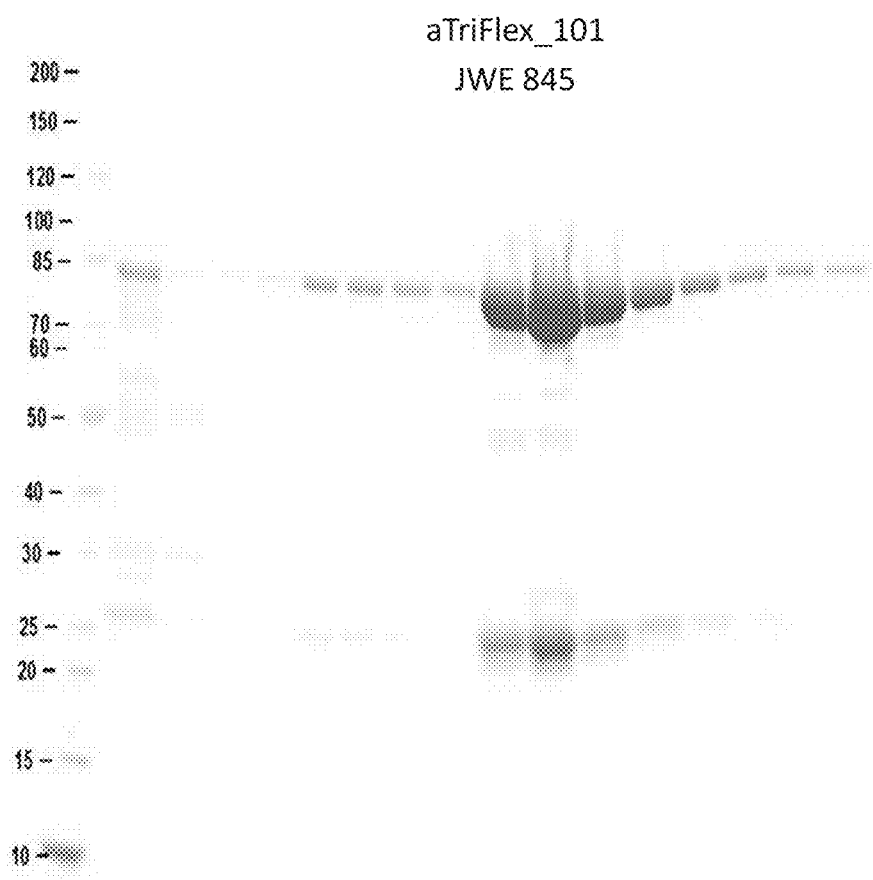
FIGS. 11A-11D shows SDS-PAGE analysis of aTriFlex-products. Long and short polypeptides are well expressed. A) aTriFlex_101, B) aTriFlex_102, C) aTriFlex_103 and D) aTriFlex_104.
Figure 11B:
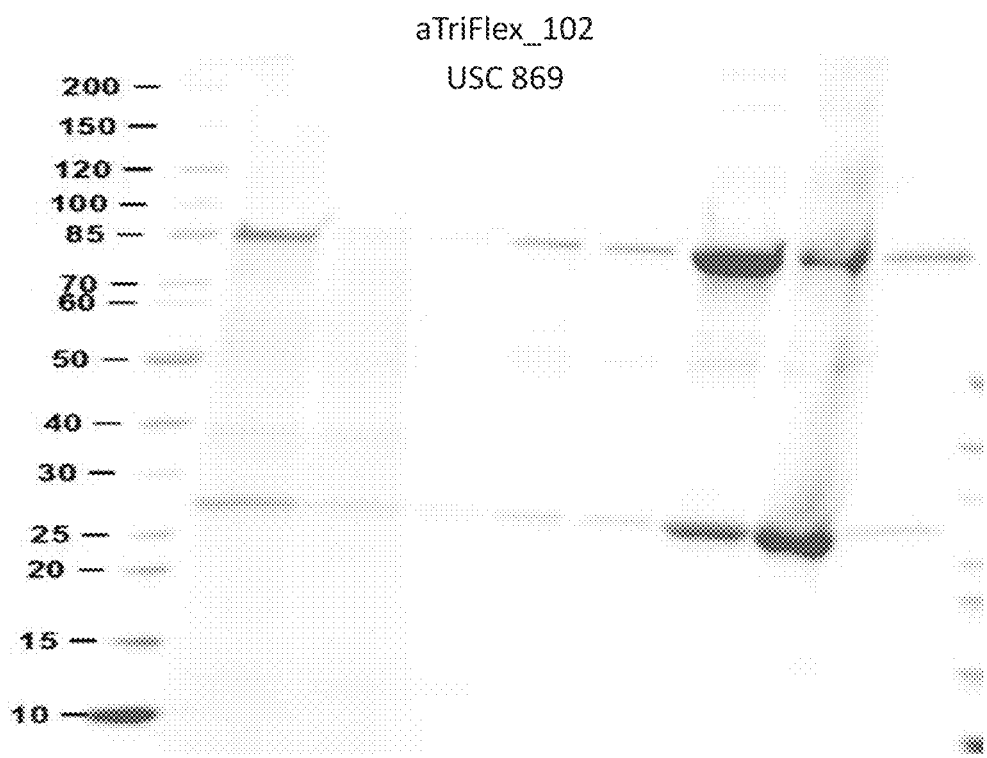
Figure 11C:
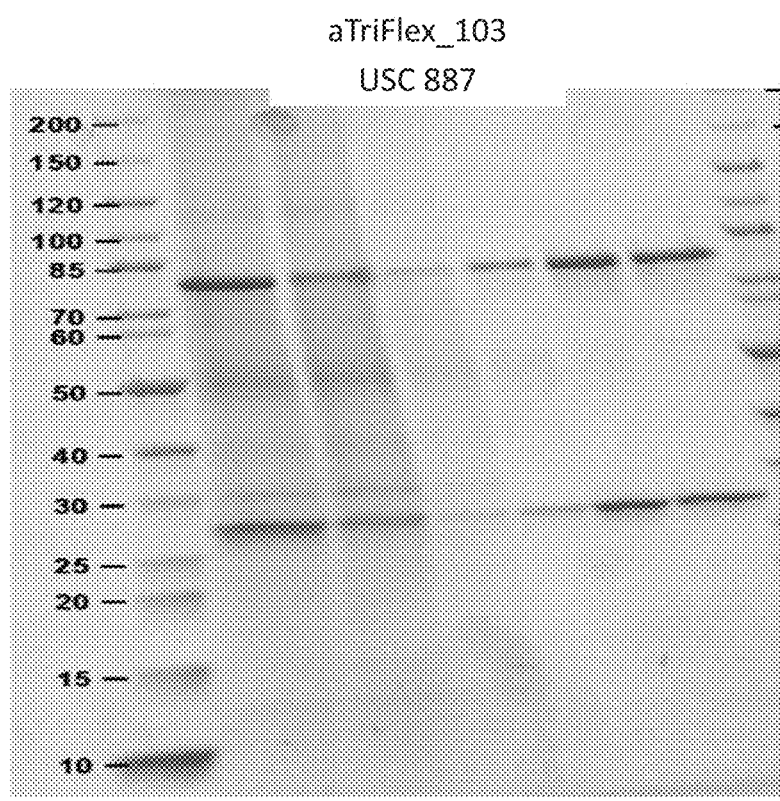
Figure 11D:
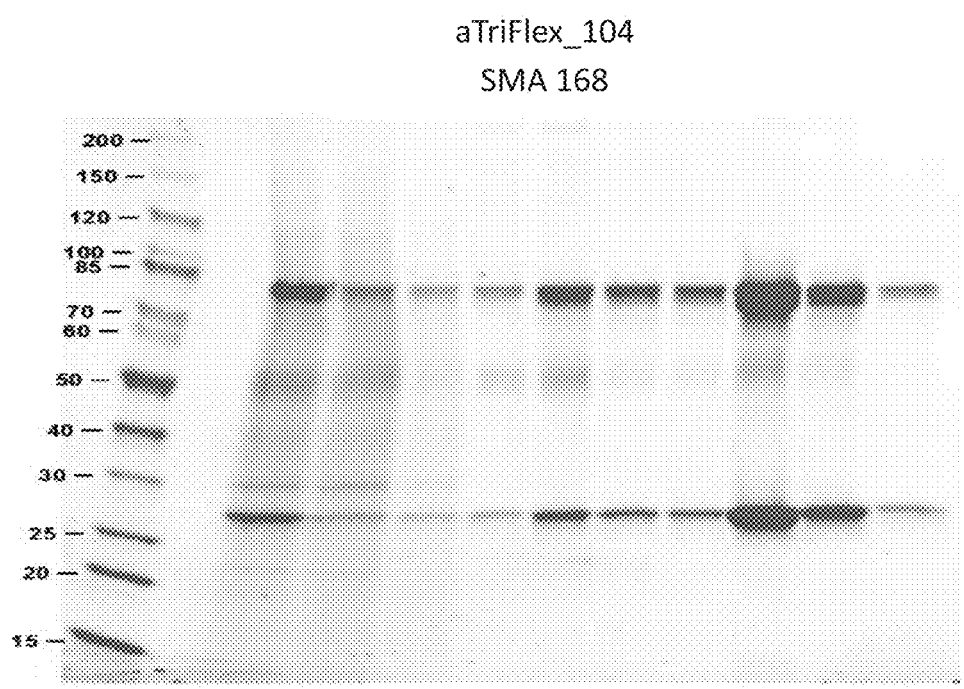

After purification by a single IMAC-step as described in Example 1 a purity of 76% was achieved for aTriFlex_140 (FIG. 10a) and a purity of 78% was achieved for aTriFlex_142 (FIG. 10c). Hence, multispecific Fv antibody molecules with a $V_L$-$V_L$/$V_H$-$V_H$ diabody unit (aTriFlex_140) or a $V_H$-$V_H$/$V_L$-$V_L$ diabody unit (aTriFlex_142) show a significant high proportion of correctly folded Fv antibody molecules. However, several overlapping molecular species were obtained and no heterodimeric antibody molecules were separable from aTriFlex_138 and aTriFlex_139 having alternating domain orders $V_H$-$V_L$/$V_H$-$V_L$ and $V_L$-$V_H$/$V_L$-$V_H$, respectively, in their diabody units (FIGS. 10b, 10d). Hence, the $V_L$-$V_L$/$V_H$-$V_H$ orientation of the variable domains in the diabody unit forces the two different polypeptides 1 and 2 to associate with each other and heterodimerize to a tetravalent, trispecific antibody molecule.

Example 3

The following multivalent antibody molecules comprising anti-CD16A, anti-CD19 and anti-CD30 antibody variable domains were produced:

Linkers:
The following peptide linkers were used in the examples:
Linker (4) in scFv-unit: $(G_2S)_6$ for $V_H$-$V_L$ and $(G_2S)_7$ for $V_L$-$V_H$
Linker (3, 3a) in diabody-unit: $(G_2S)_3$
Linker (5) connecting scFv-unit with diabody-unit: $(G_2S)_3$ a) A tetravalent, trispecific Fv antibody molecule (aTriFlex_101 as shown in FIG. 2) having specificities for CD30, CD19 and CD16A consisting of a first polypeptide having six variable domains and a C-terminal His-tag; and a second polypeptide having two variable domains and a C-terminal FLAG-tag. The centrally located dimeric diabody unit is formed by the pair of $V_H$-$V_H$ domains in the first polypeptide and the pair of $V_L$-$V_L$ domains in the second polypeptide which ensures the correct heterodimerization of polypeptide 1 and polypeptide 2.

| Polypetide | Domain Specificities (N -> C) | Domain Order (N -> C) |
|---|---|---|
| 1 | CD30-CD30-CD16A-CD16A-CD19-CD19-His | $V_H$-$V_L$-$V_H$-$V_H$-$V_L$-$V_H$ |
| 2 | CD16A-CD16A-FLAG | $V_L$-$V_L$ |

Amino Acid Sequences:

Polypeptide 1:
(SEQ ID NO: 1)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSQVQLVQSGAEVKKPGESLKVSCKASGYTFTSYYMHWVRQAPGQ

GLEWMGIINPSGGSTSYAQKFQGRVTMTRDTSTSTVYMELSSLRSEDTAV

YYCARGSAYYYDFADYWGQGTLVTVSSGGSGGSGGSQVQLVQSGAEVKKP

GESLKVSCKASGYTFTSYYMHWVRQAPGQGLEWMGIINPSGGSTSYAQKF

QGRVTMTRDTSTSTVYMELSSLRSEDTAVYYCARGSAYYYDFADYWGQGT

LVTVSSGGSGGSGGSSYVLTQPPSVSVAPGQTARITCGGNNIGSKTVHWY

QQKPGQAPVLVVYDDSDRPSGIPERFSGSNSGNTATLTISRVEAGDEADY

YCQVGTDWSDHLQVFGGGTKLTVLGGSGGSGGSGGSGGSGGSGGSEVQLV

QSGAEVKKPGESLKISCKGSGYSFTSNWIGWVRQMPGKGLEWMGMIWPGD

SDTMYSPSFQGQVTISADESINTAYLQWSSLKASDTAMYYCARRETTTVG

RYYYAMDYWGQGTLVTVSSAAAGSHHHHHH

Polypeptide 2:
(SEQ ID NO: 2)
SYVLTQPSSVSVAPGQTATISCGGHNIGSKNVHWYQQRPGQSPVLVIYQD

NKRPSGIPERFSGSNSGNTATLTISGTQAMDEADYYCQVWDNYSVLFGGG

TKLTVLGGSGGSGGSSYVLTQPSSVSVAPGQTATISCGGHNIGSKNVHWY

QQRPGQSPVLVIYQDNKRPSGIPERFSGSNSGNTATLTISGTQAMDEADY

YCQVWDNYSVLFGGGTKLTVLAAAGSDYKDDDDK b) A tetravalent, trispecific Fv antibody (aTriFlex_102) having specificities for CD30, CD19 and CD16A, and consisting of a first polypeptide having six variable domains and a C-terminal His-tag; and a second polypeptide having two variable domains and a C-terminal FLAG-tag. The centrally located dimeric diabody unit is formed by the pair of $V_H$-$V_H$ domains in the first polypeptide and the pair of $V_L$-$V_L$ domains in the second polypeptide.

| Polypeptide | Domain Specificities (N -> C) | Domain Order (N -> C) |
|---|---|---|
| 1 | CD19-CD19-CD16A-CD16A-CD30-CD30-His | $V_L$-$V_H$-$V_H$-$V_H$-$V_H$-$V_L$ |
| 2 | CD16A-CD16A-FLAG | $V_L$-$V_L$ |

Amino Acid Sequences:

Polypeptide 1:
(SEQ ID NO: 3)
SYVLTQPPSVSVAPGQTARITCGGNNIGSKTVHWYQQKPGQAPVLVVYDD
SDRPSGIPERFSGSNSGNTATLTISRVEAGDEADYYCQVGTDWSDHLQVF
GGGTKLTVLGGSGGSGGSGGSGGSGGSGGSEVQLVQSGAEVKKPGESLKI
SCKGSGYSFTSNWIGWVRQMPGKGLEWMGMIWPGDSDTMYSPSFQGQVTI
SADESINTAYLQWSSLKASDTAMYYCARRETTTVGRYYYAMDYWGQGTLV
TVSSGGSGGSGGSQVQLVQSGAEVKKPGESLKVSCKASGYTFTSYYMHWV
RQAPGQGLEWMGIINPSGGSTSYAQKFQGRVTMTRDTSTSTVYMELSSLR
SEDTAVYYCARGSAYYYDFADYWGQGTLVTVSSGGSGGSGGSQVQLVQSG
AEVKKPGESLKVSCKASGYTFTSYYMHWVRQAPGQGLEWMGIINPSGGST
SYAQKFQGRVTMTRDTSTSTVYMELSSLRSEDTAVYYCARGSAYYYDFAD
YWGQGTLVTVSSGGSGGSGGSQVQLQQSGAELARPGASVKMSCKASGYTF
TTYTIHWVRQRPGHDLEWIGYINPSSGYSDYNQNFKGKTTLTADKSSNTA
YMQLNSLTSEDSAVYYCARRADYGNYEYTWFAYWGQGTTVTVSSGGSGGS
GGSGGSGGSGGSDIVMTQSPKFMSTSVGDRVTVTCKASQNVGTNVAWFQQ
KPGQSPKVLIYSASYRYSGVPDRFTGSGSGTDFTLTISNVQSEDLAEYFC
QQYHTYPLTFGGGTKLEINAAAGSHHHHHH Polypeptide 2:
(SEQ ID NO: 4)
SYVLTQPSSVSVAPGQTATISCGGHNIGSKNVHWYQQRPGQSPVLVIYQD
NKRPSGIPERFSGSNSGNTATLTISGTQAMDEADYYCQVWDNYSVLFGGG
TKLTVLGGSGGSGGSSYVLTQPSSVSVAPGQTATISCGGHNIGSKNVHWY
QQRPGQSPVLVIYQDNKRPSGIPERFSGSNSGNTATLTISGTQAMDEADY
YCQVWDNYSVLFGGGTKLTVLAAAGSDYKDDDDK c) A tetravalent, trispecific Fv antibody (aTriFlex_103) having specificities for CD30, CD19 and CD16A consisting of a first polypeptide having six variable domains and a C-terminal FLAG-tag; and a second polypeptide having two variable domains and a C-terminal His-tag. The centrally located dimeric diabody unit is formed by the pair of $V_H$-$V_H$ domains in the first polypeptide and the pair of $V_L$-$V_L$ domains in the second polypeptide.

| Polypeptide | Domain Specificities (N -> C) | Domain Order (N -> C) |
|---|---|---|
| 1 | CD19-CD19-CD16A-CD16A-CD30-CD30-FLAG | $V_L$-$V_H$-$V_L$-$V_L$-$V_H$-$V_L$ |
| 2 | CD16A-CD16A-His | $V_H$-$V_H$ |

Amino Acid Sequences:

Polypeptide 1:
(SEQ ID NO: 5)
SYVLTQPPSVSVAPGQTARITCGGNNIGSKTVHWYQQKPGQAPVLVVYDD
SDRPSGIPERFSGSNSGNTATLTISRVEAGDEADYYCQVGTDWSDHLQVF
GGGTKLTVLGGSGGSGGSGGSGGSGGSGGSEVQLVQSGAEVKKPGESLKI
SCKGSGYSFTSNWIGWVRQMPGKGLEWMGMIWPGDSDTMYSPSFQGQVTI
SADESINTAYLQWSSLKASDTAMYYCARRETTTVGRYYYAMDYWGQGTLV
TVSSGGSGGSGGSSYVLTQPSSVSVAPGQTATISCGGHNIGSKNVHWYQQ
RPGQSPVLVIYQDNKRPSGIPERFSGSNSGNTATLTISGTQAMDEADYYC
QVWDNYSVLFGGGTKLTVLGGSGGSGGSSYVLTQPSSVSVAPGQTATISC
GGHNIGSKNVHWYQQRPGQSPVLVIYQDNKRPSGIPERFSGSNSGNTATL
TISGTQAMDEADYYCQVWDNYSVLFGGGTKLTVLGGSGGSGGSQVQLQQS
GAELARPGASVKMSCKASGYTFTTYTIHWVRQRPGHDLEWIGYINPSSGY
SDYNQNFKGKTTLTADKSSNTAYMQLNSLTSEDSAVYYCARRADYGNYEY
TWFAYWGQGTTVTVSSGGSGGSGGSGGSGGSGGSDIVMTQSPKFMSTSVG
DRVTVTCKASQNVGTNVAWFQQKPGQSPKVLIYSASYRYSGVPDRFTGSG
SGTDFTLTISNVQSEDLAEYFCQQYHTYPLTFGGGTKLEINAAAGSHHHH
HH Polypeptide 2:
(SEQ ID NO: 6)
QVQLVQSGAEVKKPGESLKVSCKASGYTFTSYYMHWVRQAPGQGLEWMGI
INPSGGSTSYAQKFQGRVTMTRDTSTSTVYMELSSLRSEDTAVYYCARGS
AYYYDFADYWGQGTLVTVSSGGSGGSGGSQVQLVQSGAEVKKPGESLKVS
CKASGYTFTSYYMHWVRQAPGQGLEWMGIINPSGGSTSYAQKFQGRVTMT
RDTSTSTVYMELSSLRSEDTAVYYCARGSAYYYDFADYWGQGTLVTVSSA
AAGSDYKDDDDK d) A tetravalent, trispecific Fv antibody (aTriFlex_104) having specificities for CD30, CD19 and CD16A and consisting of a first polypeptide having six variable domains and a C-terminal FLAG-tag; and a second polypeptide having two variable domains and a C-terminal His-tag. The centrally located dimeric diabody unit is formed by the pair of $V_H$-$V_H$ domains in the first polypeptide and the pair of $V_L$-$V_L$ domains in the second polypeptide.

| Polypeptide | Domain Specificities (N -> C) | Domain Order (N -> C) |
|---|---|---|
| 1 | CD30-CD30-CD16A-CD16A-CD19-CD19-FLAG | $V_H$-$V_L$-$V_L$-$V_L$-$V_L$-$V_H$ |
| 2 | CD16A-CD16A-His | $V_H$-$V_H$ |

Amino Acid Sequences:

Polypeptide 1:
(SEQ ID NO: 7)
QVQLQQSGAELARPGASVKMSCKASGYTFTTYTIHWVRQRPGHDLEWIGY
INPSSGYSDYNQNFKGKTTLTADKSSNTAYMQLNSLTSEDSAVYYCARRA
DYGNYEYTWFAYWGQGTTVTVSSGGSGGSGGSGGSGGSGGSDIVMTQSPK

```
FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSSYVLTQPSSVSVAPGQTATISCGGHNIGSKNVHWYQQRPGQSP

VLVIYQDNKRPSGIPERFSGSNSGNTATLTISGTQAMDEADYYCQVWDNY

SVLFGGGTKLTVLGGSGGSGGSSYVLTQPSSVSVAPGQTATISCGGHNIG

SKNVHWYQQRPGQSPVLVIYQDNKRPSGIPERFSGSNSGNTATLTISGTQ

AMDEADYYCQVWDNYSVLFGGGTKLTVLGGSGGSGGSSYVLTQPPSVSVA

PGQTARITCGGNNIGSKTVHWYQQKPGQAPVLVVYDDSDRPSGIPERFSG

SNSGNTATLTISRVEAGDEADYYCQVGTDWSDHLQVFGGGTKLTVLGGSG

GSGGSGGSGGSGGSGGSEVQLVQSGAEVKKPGESLKISCKGSGYSFTSNW

IGWVRQMPGKGLEWMGMIWPGDSDTMYSPSFQGQVTISADESINTAYLQW

SSLKASDTAMYYCARRETTTVGRYYYAMDYWGQGTLVTVSSAAAGSDYKD

DDDK
```

Polypeptide 2:
(SEQ ID NO: 8)
```
QVQLVQSGAEVKKPGESLKVSCKASGYTFTSYYMHWVRQAPGQGLEWMGI

INPSGGSTSYAQKFQGRVTMTRDTSTSTVYMELSSLRSEDTAVYYCARGS

AYYYDFADYWGQGTLVTVSSGGSGGSGGSQVQLVQSGAEVKKPGESLKVS

CKASGYTFTSYYMHWVRQAPGQGLEWMGIINPSGGSTSYAQKFQGRVTMT

RDTSTSTVYMELSSLRSEDTAVYYCARGSAYYYDFADYWGQGTLVTVSSA

AAGSHHHHHH
```

Despite the different sizes of polypeptide 1 (six variable domains) and polypeptide 2 (two variable domains) the antibody molecules a), b), c) and d) can be expressed satisfactorily. Thermal as well as storage stability of purified antibody molecules a)-d) is very good. All constructs a)-d) bind to primary NK cells, Raji, Karpas-299 and MEC-1 cell lines in flow cytometry.

e) A tetravalent, trispecific Fv antibody (TeTrisAb_1) as shown in FIG. 3 having specificities for CD30, CD19 and CD16A and consisting of a first polypeptide having four variable domains and a C-terminal His-tag; and a second polypeptide having four variable domains and a C-terminal FLAG-tag. The centrally located dimeric diabody unit is formed by the pair of $V_H$-$V_H$ domains in the first polypeptide and the pair of $V_L$-$V_L$ domains in the second polypeptide which orientation ensures the correct heterodimerization of the first and second polypeptide.

| Polypeptide | Domain Specificities (N -> C) | Domain Order (N -> C) |
|---|---|---|
| 1 | CD30-CD16A-CD16A-CD19-His | $V_L$-$V_H$-$V_H$-$V_L$ |
| 2 | CD19-CD16A-CD16A-CD30-FLAG | $V_H$-$V_L$-$V_L$-$V_H$ |

Amino Acid Sequences

Polypeptide 1:
(SEQ ID NO: 9)
```
DIVMTQSPKFMSTSVGDRVTVTCKASQNVGTNVAWFQQKPGQSPKVLIYS

ASYRYSGVPDRFTGSGSGTDFTLTISNVQSEDLAEYFCQQYHTYPLTFGG

GTKLEINGGSGGSGGSQVQLVQSGAEVKKPGESLKVSCKASGYTFTSYYM

HWVRQAPGQGLEWMGIINPSGGSTSYAQKFQGRVTMTRDTSTSTVYMELS

SLRSEDTAVYYCARGSAYYYDFADYWGQGTLVTVSSGGSGGSGGSQVQLV

QSGAEVKKPGESLKVSCKASGYTFTSYYMHWVRQAPGQGLEWMGIINPSG

GSTSYAQKFQGRVTMTRDTSTSTVYMELSSLRSEDTAVYYCARGSAYYYD

FADYWGQGTLVTVSSGGSGGSGGSSYVLTQPPSVSVAPGQTARITCGGNN

IGSKTVHWYQQKPGQAPVLVVYDDSDRPSGIPERFSGSNSGNTATLTISR

VEAGDEADYYCQVGTDWSDHLQVFGGGTKLTVLAAAGSHHHHHH
```

Polypeptide 2:
(SEQ ID NO: 10)
```
EVQLVQSGAEVKKPGESLKISCKGSGYSFTSNWIGWVRQMPGKGLEWMGM

IWPGDSDTMYSPSFQGQVTISADESINTAYLQWSSLKASDTAMYYCARRE

TTTVGRYYYAMDYWGQGTLVTVSSGGSGGSGGSSYVLTQPSSVSVAPGQT

ATISCGGHNIGSKNVHWYQQRPGQSPVLVIYQDNKRPSGIPERFSGSNSG

NTATLTISGTQAMDEADYYCQVWDNYSVLFGGGTKLTVLGGSGGSGGSSY

VLTQPSSVSVAPGQTATISCGGHNIGSKNVHWYQQRPGQSPVLVIYQDNK

RPSGIPERFSGSNSGNTATLTISGTQAMDEADYYCQVWDNYSVLFGGGTK

LTVLGGSGGSGGSQVQLQQSGAELARPGASVKMSCKASGYTFTTYTIHWV

RQRPGHDLEWIGYINPSSGYSDYNQNFKGKTTLTADKSSNTAYMQLNSLT

SEDSAVYYCARRADYGNYEYTWFAYWGQGTTVTVSSAAAGSDYKDDDDK
``` f) A tetravalent, trispecific Fv antibody (scTriFlex_2) as shown in FIG. 1 having specificity for CD30, CD19 and CD16A and consisting of a single polypeptide having eight variable domains and C-terminally a His-tag. The centrally located dimeric diabody unit is formed by a first pair of $V_H$-$V_H$ domains associated with a juxtaposed second pair of $V_L$-$V_L$ domains in the same polypeptide. The $V_H$-$V_H$ pair is connected with the $V_L$-$V_L$ pair by the linker $(G_2S)_6$.

| Domain Specificities (N -> C) | Domain Order (N -> C) |
|---|---|
| CD30-CD30-CD16A-CD16A-CD16A-CD16A-CD19-CD19-His | $V_H$-$V_L$-$V_H$-$V_H$-$V_L$-$V_L$-$V_L$-$V_H$ |

Amino acid sequence:
(SEQ ID NO: 11)
```
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSQVQLVQSGAEVKKPGESLKVSCKASGYTFTSYYMHWVRQAPGQ

GLEWMGIINPSGGSTSYAQKFQGRVTMTRDTSTSTVYMELSSLRSEDTAV

YYCARGSAYYYDFADYWGQGTLVTVSSGGSGGSGGSQVQLVQSGAEVKKP

GESLKVSCKASGYTFTSYYMHWVRQAPGQGLEWMGIINPSGGSTSYAQKF

QGRVTMTRDTSTSTVYMELSSLRSEDTAVYYCARGSAYYYDFADYWGQGT

LVTVSSGGSGGSGGSGGSGGSGGSSYVLTQPSSVSVAPGQTATISCGGHN
```

-continued
IGSKNVHWYQQRPGQSPVLVIYQDNKRPSGIPERFSGSNSGNTATLTISG

TQAMDEADYYCQVWDNYSVLFGGGTKLTVLGGSGGSGGSSYVLTQPSSVS

VAPGQTATISCGGHNIGSKNVHWYQQRPGQSPVLVIYQDNKRPSGIPERF

SGSNSGNTATLTISGTQAMDEADYYCQVWDNYSVLFGGGTKLTVLGGSGG

SGGSSYVLTQPPSVSVAPGQTARITCGGNNIGSKTVHWYQQKPGQAPVLV

VYDDSDRPSGIPERFSGSNSGNTATLTISRVEAGDEADYYCQVGTDWSDH

LQVFGGGTKLTVLGGSGGSGGSGGSGGSGGSGGSEVQLVQSGAEVKKPGE

SLKISCKGSGYSFTSNWIGWVRQMPGKGLEWMGMIWPGDSDTMYSPSFQG

QVTISADESINTAYLQWSSLKASDTAMYYCARRETTTVGRYYYAMDYWGQ

GTLVTVSSAAAGSHHHHHH g) A tetravalent, trispecific Fv antibody molecule (as shown in FIG. 2) having specificities for CD30, CD19 and CD16A consisting of a first polypeptide having six variable domains and a C-terminal His-tag; and a second polypeptide having two variable domains and a C-terminal FLAG-tag. The centrally located dimeric diabody unit is formed by the pair of $V_L$-$V_L$ domains in the first polypeptide and the pair of $V_H$-$V_H$ domains in the second polypeptide which ensures the correct heterodimerization of polypeptide 1 and polypeptide 2.

| Polypeptide | Domain Specificities (N -> C) | Domain Order (N -> C) |
|---|---|---|
| 1 | CD30-CD30-CD16A-CD16A-CD19-CD19-His | VH-VL-VL-VL-VH-VL |
| 2 | CD16A-CD16A-FLAG | VH-VH |

Polypeptide 1:
(SEQ ID NO: 12)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSSYVLTQPSSVSVAPGQTATISCGGHNIGSKNVHWYQQRPGQSP

VLVIYQDNKRPSGIPERFSGSNSGNTATLTISGTQAMDEADYYCQVWDNY

SVLFGGGTKLTVLGGSGGSGGSSYVLTQPSSVSVAPGQTATISCGGHNIG

SKNVHWYQQRPGQSPVLVIYQDNKRPSGIPERFSGSNSGNTATLTISGTQ

AMDEADYYCQVWDNYSVLFGGGTKLTVLGGSGGSGGSEVQLVQSGAEVKK

PGESLKISCKGSGYSFTSNWIGWVRQMPGKGLEWMGMIWPGDSDTMYSPS

FQGQVTISADESINTAYLQWSSLKASDTAMYYCARRETTTVGRYYYAMDY

WGQGTLVTVSSGGSGGSGGSGGSGGSGGSSYVLTQPPSVSVAPGQTARIT

CGGNNIGSKTVHWYQQKPGQAPVLVVYDDSDRPSGIPERFSGSNSGNTAT

LTISRVEAGDEADYYCQVGTDWSDHLQVFGGGTKLTVLAAAGSHHHHHH

Polypeptide 2:
(SEQ ID NO: 13)
QVQLVQSGAEVKKPGESLKVSCKASGYTFTSYYMHWVRQAPGQGLEWMGI

INPSGGSTSYAQKFQGRVTMTRDTSTSTVYMELSSLRSEDTAVYYCARGS

AYYYDFADYWGQGTLVTVSSGGSGGSGGSQVQLVQSGAEVKKPGESLKVS

CKASGYTFTSYYMHWVRQAPGQGLEWMGIINPSGGSTSYAQKFQGRVTMT

RDTSTSTVYMELSSLRSEDTAVYYCARGSAYYYDFADYWGQGTLVTVSSA

AAGSDYKDDDDK h) A pentavalent, tetraspecific Fv antibody molecule (as shown in FIG. 6a) having specificities for CD30, CD19, EGFRvIII and CD16A consisting of a first polypeptide having six variable domains and a C-terminal His-tag; and a second polypeptide having four variable domains and a C-terminal FLAG-tag. The dimeric diabody unit having two antigen binding sites for CD16A is formed by the pair of $V_L$-$V_L$ domains in the first polypeptide and the pair of $V_H$-$V_H$ domains in the second polypeptide which ensures the correct heterodimerization of polypeptide 1 and polypeptide 2.

| Polypeptide | Domain Specificities (N -> C) | Domain Order (N -> C) |
|---|---|---|
| 1 | CD30-CD30-CD16A-CD16A-CD19-CD19-His | VH-VL-VL-VL-VH-VL |
| 2 | CD16A-CD16A-EGFRvIII-EGFRvIII-FLAG | VH-VH-VL-VH |

Polypeptide 1:
(SEQ ID NO: 14)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSSYVLTQPSSVSVAPGQTATISCGGHNIGSKNVHWYQQRPGQSP

VLVIYQDNKRPSGIPERFSGSNSGNTATLTISGTQAMDEADYYCQVWDNY

SVLFGGGTKLTVLGGSGGSGGSSYVLTQPSSVSVAPGQTATISCGGHNIG

SKNVHWYQQRPGQSPVLVIYQDNKRPSGIPERFSGSNSGNTATLTISGTQ

AMDEADYYCQVWDNYSVLFGGGTKLTVLGGSGGSGGSEVQLVQSGAEVKK

PGESLKISCKGSGYSFTSNWIGWVRQMPGKGLEWMGMIWPGDSDTMYSPS

FQGQVTISADESINTAYLQWSSLKASDTAMYYCARRETTTVGRYYYAMDY

WGQGTLVTVSSGGSGGSGGSGGSGGSGGSSYVLTQPPSVSVAPGQTARIT

CGGNNIGSKTVHWYQQKPGQAPVLVVYDDSDRPSGIPERFSGSNSGNTAT

LTISRVEAGDEADYYCQVGTDWSDHLQVFGGGTKLTVLAAAGSHHHHHH

Polypeptide 2:
(SEQ ID NO: 15)
QVQLVQSGAEVKKPGESLKVSCKASGYTFTSYYMHWVRQAPGQGLEWMGI

INPSGGSTSYAQKFQGRVTMTRDTSTSTVYMELSSLRSEDTAVYYCARGS

AYYYDFADYWGQGTLVTVSSGGSGGSGGSQVQLVQSGAEVKKPGESLKVS

CKASGYTFTSYYMHWVRQAPGQGLEWMGIINPSGGSTSYAQKFQGRVTMT

RDTSTSTVYMELSSLRSEDTAVYYCARGSAYYYDFADYWGQGTLVTVSSG

GSGGSGGSSYELTQPPSVSVSPGQTARITCSGDALPKQYAYWYQQKPGQA

```
PVLVIYKDSERPSGIPERFSGSSSGTTVTLTISGVQAEDEADYYCQSADS

SGTPLIVFGTGTKLTVLGGSGGSGGSGGSGGSGGSGGSEVQLVQSGAEVK

KPGESLKISCKGSGYSFTSYWIGWVRQMPGKGLEWMGIIYPGDSDTRYSP

SFQGQVTISADKSISTAYLQWSSLKASDTAMYYCARLGSSWTNDAFDIWG

QGTMVTVSSAAAGSDYKDDDDK
``` i) A hexavalent, trispecifictetraspecific Fv antibody molecule (as shown in FIG. 5) having specificities for CD30, CD19 and CD16A consisting of a first polypeptide having ten variable domains and a C-terminal His-tag; and a second polypeptide having two variable domains and a C-terminal FLAG-tag. The centrally located dimeric diabody unit having two antigen binding sites for CD16A is formed by the pair of $V_L$-$V_L$ domains in the first polypeptide and the pair of $V_H$-$V_H$ domains in the second polypeptide which ensures the correct heterodimerization of polypeptide 1 and polypeptide 2

| Polypeptide | Domain Specificities (N -> C) | Domain Order (N -> C) |
|---|---|---|
| 1 | CD30-CD30-CD30-CD30-CD16A-CD16A-CD19-CD19-CD19-CD19-His | VH-VL-VH-VL-VL-VL-VH-VL-VH-VL |
| 2 | CD16A-CD16A-FLAG | VH-VH |

Polypeptide 1:
(SEQ ID NO: 16)
```
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSDIVMTQSPKFMSTSVGDR

VTVTCKASQNVGTNVAWFQQKPGQSPKVLIYSASYRYSGVPDRFTGSGSG

TDFTLTISNVQSEDLAEYFCQQYHTYPLTFGGGTKLEINGGSGGSGGSGG

SGGSGGSGGSQVQLQQSGAELARPGASVKMSCKASGYTFTTYTIHWVRQR

PGHDLEWIGYINPSSGYSDYNQNFKGKTTLTADKSSNTAYMQLNSLTSED

SAVYYCARRADYGNYEYTWFAYWGQGTTVTVSSGGSGGSGGSDIVMTQSP

KFMSTSVGDRVTVTCKASQNVGTNVAWFQQKPGQSPKVLIYSASYRYSGV

PDRFTGSGSGTDFTLTISNVQSEDLAEYFCQQYHTYPLTFGGGTKLEING

GSGGSGGSSYVLTQPSSVSVAPGQTATISCGGHNIGSKNVHWYQQRPGQS

PVLVIYQDNKRPSGIPERFSGSNSGNTATLTISGTQAMDEADYYCQVWDN

YSVLFGGGTKLTVLGGSGGSGGSSYVLTQPSSVSVAPGQTATISCGGHNI

GSKNVHWYQQRPGQSPVLVIYQDNKRPSGIPERFSGSNSGNTATLTISGT

QAMDEADYYCQVWDNYSVLFGGGTKLTVLGGSGGSGGSEVQLVQSGAEVK

KPGESLKISCKGSGYSFTSNWIGWVRQMPGKGLEWMGMIWPGDSDTMYSP

SFQGQVTISADESINTAYLQWSSLKASDTAMYYCARRETTTVGRYYYAMD

YWGQGTLVTVSSGGSGGSGGSSYVLTQPPSVSVAPGQTARITCGGNNIGS

KTVHWYQQKPGQAPVLVVYDDSDRPSGIPERFSGSNSGNTATLTISRVEA

GDEADYYCQVGTDWSDHLQVFGGGTKLTVLGGSGGSGGSGGSGGSGGSGG

SEVQLVQSGAEVKKPGESLKISCKGSGYSFTSNWIGWVRQMPGKGLEWMG

MIWPGDSDTMYSPSFQGQVTISADESINTAYLQWSSLKASDTAMYYCARR

ETTTVGRYYYAMDYWGQGTLVTVSSGGSGGSGGSSYVLTQPPSVSVAPGQ

TARITCGGNNIGSKTVHWYQQKPGQAPVLVVYDDSDRPSGIPERFSGSNS

GNTATLTISRVEAGDEADYYCQVGTDWSDHLQVFGGGTKLTVLAAAGSHH

HHHH
```

Polypeptide 2:
(SEQ ID NO: 17)
```
QVQLVQSGAEVKKPGESLKVSCKASGYTFTSYYMHWVRQAPGQGLEWMGI

INPSGGSTSYAQKFQGRVTMTRDTSTSTVYMELSSLRSEDTAVYYCARGS

AYYYDFADYWGQGTLVTVSSGGSGGSGGSQVQLVQSGAEVKKPGESLKVS

CKASGYTFTSYYMHWVRQAPGQGLEWMGIINPSGGSTSYAQKFQGRVTMT

RDTSTSTVYMELSSLRSEDTAVYYCARGSAYYYDFADYWGQGTLVTVSSA

AAGSDYKDDDDK
``` j) A hexavalent, tetraspecific Fv antibody molecule (as shown in FIG. 7) having specificities for CD30, CD19, EGFRvIII and CD16A consisting of a first polypeptide having six variable domains and a C-terminal His-tag; and a second polypeptide having six variable domains and a C-terminal FLAG-tag.

| Polypeptide | Domain Specificities (N -> C) | Domain Order (N -> C) |
|---|---|---|
| 1 | CD30-CD30-CD16A-CD16A-CD19-CD19-His | VH-VL-VL-VL-VH-VL |
| 2 | CD30-CD30-CD16A-CD16A-EGFRvIII-EGFRvIII-FLAG | VH-VL-VH-VH-VL-VH |

Polypeptide 1:
(SEQ ID NO: 18)
```
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSSYVLTQPSSVSVAPGQTATISCGGHNIGSKNVHWYQQRPGQSP

VLVIYQDNKRPSGIPERFSGSNSGNTATLTISGTQAMDEADYYCQVWDNY

SVLFGGGTKLTVLGGSGGSGGSSYVLTQPSSVSVAPGQTATISCGGHNIG

SKNVHWYQQRPGQSPVLVIYQDNKRPSGIPERFSGSNSGNTATLTISGTQ

AMDEADYYCQVWDNYSVLFGGGTKLTVLGGSGGSGGSEVQLVQSGAEVKK

PGESLKISCKGSGYSFTSNWIGWVRQMPGKGLEWMGMIWPGDSDTMYSPS

FQGQVTISADESINTAYLQWSSLKASDTAMYYCARRETTTVGRYYYAMDY

WGQGTLVTVSSGGSGGSGGSGGSGGSGGSSYVLTQPPSVSVAPGQTARIT

CGGNNIGSKTVHWYQQKPGQAPVLVVYDDSDRPSGIPERFSGSNSGNTAT

LTISRVEAGDEADYYCQVGTDWSDHLQVFGGGTKLTVLAAAGSHHHHHH
```

Polypeptide 2:
(SEQ ID NO: 19)
```
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA
```

-continued
DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSQVQLVQSGAEVKKPGESLKVSCKASGYTFTSYYMHWVRQAPGQ

GLEWMGIINPSGGSTSYAQKFQGRVTMTRDTSTSTVYMELSSLRSEDTAV

YYCARGSAYYYDFADYWGQGTLVTVSSGGSGGSGGSQVQLVQSGAEVKKP

GESLKVSCKASGYTFTSYYMHWVRQAPGQGLEWMGIINPSGGSTSYAQKF

QGRVTMTRDTSTSTVYMELSSLRSEDTAVYYCARGSAYYYDFADYWGQGT

LVTVSSGGSGGSGGSSYELTQPPSVSVSPGQTARITCSGDALPKQYAYWY

QQKPGQAPVLVIYKDSERPSGIPERFSGSSSGTTVTLTISGVQAEDEADY

YCQSADSSGTPLIVFGTGTKLTVLGGSGGSGGSGGSGGSGGSGGSEVQLV

QSGAEVKKPGESLKISCKGSGYSFTSYWIGWVRQMPGKGLEWMGIIYPGD

SDTRYSPSFQGQVTISADKSISTAYLQWSSLKASDTAMYYCARLGSSWTN

DAFDIWGQGTMVTVSSAAAGSDYKDDDDK k) A pentavalent, trispecific Fv antibody molecule (as shown in FIG. 6b) having specificities for CD30, CD19 and CD16A consisting of a first polypeptide having six variable domains and a C-terminal His-tag; and a second polypeptide having four variable domains and a C-terminal FLAG-tag. The dimeric diabody unit having two antigen binding sites for CD16A is formed by the pair of $V_L$-$V_L$ domains in the first polypeptide and the pair of $V_H$-$V_H$ domains in the second polypeptide which ensures the correct heterodimerization of polypeptide 1 and polypeptide 2

| Polypeptide | Domain Specificities (N -> C) | Domain Order (N -> C) |
|---|---|---|
| 1 | CD30-CD30-CD16A-CD16A-CD19-CD19-His | VH-VL-VL-VL-VH-VL |
| 2 | CD30-CD30-CD16A-CD16A-FLAG | VH-VL-VH-VH |

Polypeptide 1:
(SEQ ID NO: 20)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSSYVLTQPSSVSVAPGQTATISCGGHNIGSKNVHWYQQRPGQSP

VLVIYQDNKRPSGIPERFSGSNSGNTATLTISGTQAMDEADYYCQVWDNY

SVLFGGGTKLTVLGGSGGSGGSSYVLTQPSSVSVAPGQTATISCGGHNIG

SKNVHWYQQRPGQSPVLVIYQDNKRPSGIPERFSGSNSGNTATLTISGTQ

AMDEADYYCQVWDNYSVLFGGGTKLTVLGGSGGSGGSEVQLVQSGAEVKK

PGESLKISCKGSGYSFTSNWIGWVRQMPGKGLEWMGMIWPGDSDTMYSPS

FQGQVTISADESINTAYLQWSSLKASDTAMYYCARRETTTVGRYYYAMDY

WGQGTLVTVSSGGSGGSGGSGGSGGSGGSSYVLTQPPSVSVAPGQTARIT

-continued
CGGNNIGSKTVHWYQQKPGQAPVLVVYDDSDRPSGIPERFSGSNSGNTAT

LTISRVEAGDEADYYCQVGTDWSDHLQVFGGGTKLTVLAAAGSHHHHHH

Polypeptide 2:
(SEQ ID NO: 21)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSQVQLVQSGAEVKKPGESLKVSCKASGYTFTSYYMHWVRQAPGQ

GLEWMGIINPSGGSTSYAQKFQGRVTMTRDTSTSTVYMELSSLRSEDTAV

YYCARGSAYYYDFADYWGQGTLVTVSSGGSGGSGGSQVQLVQSGAEVKKP

GESLKVSCKASGYTFTSYYMHWVRQAPGQGLEWMGIINPSGGSTSYAQKF

QGRVTMTRDTSTSTVYMELSSLRSEDTAVYYCARGSAYYYDFADYWGQGT

LVTVSSAAAGSDYKDDDDK l) A tetravalent, trispecific Fv antibody as shown in FIG. 3 having specificities for CD30, CD19 and CD16A and consisting of a first polypeptide having four variable domains and a C-terminal His-tag; and a second polypeptide having four variable domains and a C-terminal FLAG-tag. The centrally located dimeric diabody unit is formed by the pair of $V_L$-$V_L$ domains in the first polypeptide and the pair of $V_H$-$V_H$ domains in the second polypeptide which orientation ensures the correct heterodimerization of the first and second polypeptide.

| Polypeptide | Domain Specificities (N -> C) | Domain Order (N -> C) |
|---|---|---|
| 1 | CD30-CD16A-CD16A-CD19-His | VH-VL-VL-VH |
| 2 | CD19-CD16A-CD16A-CD30-FLAG | VL-VH-VH-VL |

Polypeptide 1:
(SEQ ID NO: 22)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSSYVLTQPSSVSVAPGQTA

TISCGGHNIGSKNVHWYQQRPGQSPVLVIYQDNKRPSGIPERFSGSNSGN

TATLTISGTQAMDEADYYCQVWDNYSVLFGGGTKLTVLGGSGGSGGSSYV

LTQPSSVSVAPGQTATISCGGHNIGSKNVHWYQQRPGQSPVLVIYQDNKR

PSGIPERFSGSNSGNTATLTISGTQAMDEADYYCQVWDNYSVLFGGGTKL

TVLGGSGGSGGSEVQLVQSGAEVKKPGESLKISCKGSGYSFTSNWIGWVR

QMPGKGLEWMGMIWPGDSDTMYSPSFQGQVTISADESINTAYLQWSSLKA

SDTAMYYCARRETTTVGRYYYAMDYWGQGTLVTVSSAAAGSHHHHHH

Polypeptide 2:
(SEQ ID NO: 23)
SYVLTQPPSVSVAPGQTARITCGGNNIGSKTVHWYQQKPGQAPVLVVYDD

SDRPSGIPERFSGSNSGNTATLTISRVEAGDEADYYCQVGTDWSDHLQVF

GGGTKLTVLGGSGGSQVQLVQSGAEVKKPGESLKVSCKASGYTFTSYYMH

```
WVRQAPGQGLEWMGIINPSGGSTSYAQKFQGRVTMTRDTSTSTVYMELSS

LRSEDTAVYYCARGSAYYYDFADYWGQGTLVTVSSGGSGGSGGSQVQLVQ

SGAEVKKPGESLKVSCKASGYTFTSYYMHWVRQAPGQGLEWMGIINPSGG

STSYAQKFQGRVTMTRDTSTSTVYMELSSLRSEDTAVYYCARGSAYYYDF

ADYWGQGTLVTVSSGGSGGSGGSDIVMTQSPKFMSTSVGDRVTVTCKASQ

NVGTNVAWFQQKPGQSPKVLIYSASYRYSGVPDRFTGSGSGTDFTLTISN

VQSEDLAEYFCQQYHTYPLTFGGGTKLEINAAAGSDYKDDDDK
``` m) A hexavalent, tetraspecific Fv antibody as shown in FIG. 8a having specificities for CD30, CD19, EGFRvIII and CD16A and consisting of a first polypeptide having six variable domains and a C-terminal His-tag; and a second polypeptide having six variable domains and a C-terminal FLAG-tag. Each of the first and second polypeptide comprises a scFv unit C-terminally.

| Polypeptide | Domain Specificities (N -> C) | Domain Order (N -> C) |
|---|---|---|
| 1 | CD30-CD16A-CD16A-CD19-EGFRvIII-EGFRvIII-His | VH-VL-VL-VH-VL-VH |
| 2 | CD19-CD16A-CD16A-CD30-EGFRvIII-EGFRvIII-FLAG | VL-VH-VH-VL-VL-VH |

```
Polypeptide 1:
                                    (SEQ ID NO: 24)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSSYVLTQPSSVSVAPGQTA

TISCGGHNIGSKNVHWYQQRPGQSPVLVIYQDNKRPSGIPERFSGSNSGN

TATLTISGTQAMDEADYYCQVWDNYSVLFGGGTKLTVLGGSGGSGGSSYV

LTQPSSVSVAPGQTATISCGGHNIGSKNVHWYQQRPGQSPVLVIYQDNKR

PSGIPERFSGSNSGNTATLTISGTQAMDEADYYCQVWDNYSVLFGGGTKL

TVLGGSGGSGGSEVQLVQSGAEVKKPGESLKISCKGSGYSFTSNWIGWVR

QMPGKGLEWMGMIWPGDSDTMYSPSFQGQVTISADESINTAYLQWSSLKA

SDTAMYYCARRETTTVGRYYYAMDYWGQGTLVTVSSGGSGGSGGSSYELT

QPPSVSVSPGQTARITCSGDALPKQYAYWYQQKPGQAPVLVIYKDSERPS

GIPERFSGSSSGTTVTLTISGVQAEDEADYYCQSADSSGTPLIVFGTGTK

LTVLGGSGGSGGSGGSGGSGGSEVQLVQSGAEVKKPGESLKISCKGS

GYSFTSYWIGWVRQMPGKGLEWMGIIYPGDSDTRYSPSFQGQVTISADKS

ISTAYLQWSSLKASDTAMYYCARLGSSWTNDAFDIWGQGTMVTVSSAAAG

SHHHHHH

Polypeptide 2:
                                    (SEQ ID NO: 25)
SYVLTQPPSVSVAPGQTARITCGGNNIGSKTVHWYQQKPGQAPVLVVYDD

SDRPSGIPERFSGSNSGNTATLTISRVEAGDEADYYCQVGTDWSDHLQVF

GGGTKLTVLGGSGGSQVQLVQSGAEVKKPGESLKVSCKASGYTFTSYYMH

WVRQAPGQGLEWMGIINPSGGSTSYAQKFQGRVTMTRDTSTSTVYMELSS

LRSEDTAVYYCARGSAYYYDFADYWGQGTLVTVSSGGSGGSGGSQVQLVQ

SGAEVKKPGESLKVSCKASGYTFTSYYMHWVRQAPGQGLEWMGIINPSGG

STSYAQKFQGRVTMTRDTSTSTVYMELSSLRSEDTAVYYCARGSAYYYDF

ADYWGQGTLVTVSSGGSGGSGGSDIVMTQSPKFMSTSVGDRVTVTCKASQ

NVGTNVAWFQQKPGQSPKVLIYSASYRYSGVPDRFTGSGSGTDFTLTISN

VQSEDLAEYFCQQYHTYPLTFGGGTKLEINGGSGGSGGSSYELTQPPSVS

VSPGQTARITCSGDALPKQYAYWYQQKPGQAPVLVIYKDSERPSGIPERF

SGSSSGTTVTLTISGVQAEDEADYYCQSADSSGTPLIVFGTGTKLTVLGG

SGGSGGSGGSGGSGGSGGSEVQLVQSGAEVKKPGESLKISCKGSGYSFTS

YWIGWVRQMPGKGLEWMGIIYPGDSDTRYSPSFQGQVTISADKSISTAYL

QWSSLKASDTAMYYCARLGSSWTNDAFDIWGQGTMVTVSSAAAGSDYKDD

Figure 8B:
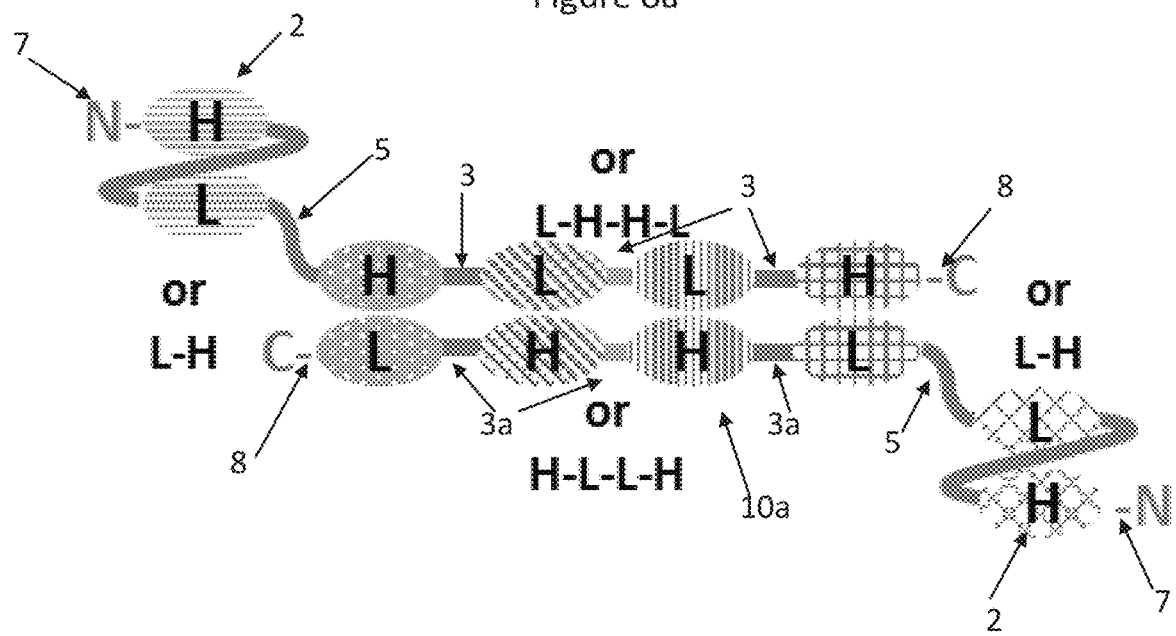

DDK
``` n) A hexavalent, tetraspecific Fv antibody as shown in FIG. 8b having specificities for CD30, CD19, EGFRvIII and CD16A and consisting of a first polypeptide having six variable domains and a C-terminal His-tag; and a second polypeptide having six variable domains and a C-terminal FLAG-tag. Each of the first and second polypeptide comprises a scFv unit N-terminally.

| Polypeptide | Domain Specificities (N -> C) | Domain Order (N -> C) |
|---|---|---|
| 1 | EGFRvIII-EGFRvIII-CD30-CD16A-CD16A-CD19-His | VH-VL-VH-VL-VL-VH |
| 2 | EGFRvIII-EGFRvIII-CD19-CD16A-CD16A-CD30-FLAG | VH-VL-VL-VH-VH-VL |

```
Polypeptide 1:
                                    (SEQ ID NO: 26)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARLG

SSWTNDAFDIWGQGTMVTVSSGGSGGSGGSGGSGGSGGSSYELTQPPSVS

VSPGQTARITCSGDALPKQYAYWYQQKPGQAPVLVIYKDSERPSGIPERF

SGSSSGTTVTLTISGVQAEDEADYYCQSADSSGTPLIVFGTGTKLTVLGG

SGGSGGSQVQLQQSGAELARPGASVKMSCKASGYTFTTYTIHWVRQRPGH

DLEWIGYINPSSGYSDYNQNFKGKTTLTADKSSNTAYMQLNSLTSEDSAV

YYCARRADYGNYEYTWFAYWGQGTTVTVSSGGSGGSGGSSYVLTQPSSVS

VAPGQTATISCGGHNIGSKNVHWYQQRPGQSPVLVIYQDNKRPSGIPERF

SGSNSGNTATLTISGTQAMDEADYYCQVWDNYSVLFGGGTKLTVLGGSGG

SGGSSYVLTQPSSVSVAPGQTATISCGGHNIGSKNVHWYQQRPGQSPVLV

IYQDNKRPSGIPERFSGSNSGNTATLTISGTQAMDEADYYCQVWDNYSVL

FGGGTKLTVLGGSGGSGGSEVQLVQSGAEVKKPGESLKISCKGSGYSFTS

NWIGWVRQMPGKGLEWMGMIWPGDSDTMYSPSFQGQVTISADESINTAYL

QWSSLKASDTAMYYCARRETTTVGRYYYAMDYWGQGTLVTVSSAAAGSHH

HHHH
```

Polypeptide 2:
(SEQ ID NO: 27)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARLG

SSWTNDAFDIWGQGTMVTVSSGGSGGSGGSGGSGGSGGSSYELTQPPSVS

VSPGQTARITCSGDALPKQYAYWYQQKPGQAPVLVIYKDSERPSGIPERF

SGSSSGTTVTLTISGVQAEDEADYYCQSADSSGTPLIVFGTGTKLTVLGG

SGGSGGSSYVLTQPPSVSVAPGQTARITCGGNNIGSKTVHWYQQKPGQAP

VLVVYDDSDRPSGIPERFSGSNSGNTATLTISRVEAGDEADYYCQVGTDW

SDHLQVFGGGTKLTVLGGSGGSQVQLVQSGAEVKKPGESLKVSCKASGYT

FTSYYMHWVRQAPGQGLEWMGIINPSGGSTSYAQKFQGRVTMTRDTSTST

VYMELSSLRSEDTAVYYCARGSAYYYDFADYWGQGTLVTVSSGGSGGSGG

SQVQLVQSGAEVKKPGESLKVSCKASGYTFTSYYMHWVRQAPGQGLEWMG

IINPSGGSTSYAQKFQGRVTMTRDTSTSTVYMELSSLRSEDTAVYYCARG

SAYYYDFADYWGQGTLVTVSSGGSGGSGGSDIVMTQSPKFMSTSVGDRVT

VTCKASQNVGTNVAWFQQKPGQSPKVLIYSASYRYSGVPDRFTGSGSGTD

FTLTISNVQSEDLAEYFCQQYHTYPLTFGGGTKLEINAAAGSDYKDDDDK o) A tetravalent, trispecific Fv antibody as shown in FIG. 1 having specificity for CD30, CD19 and CD16A and consisting of a single polypeptide having eight variable domains and C-terminally a His-tag. The centrally located single chain diabody unit is formed by a first pair of $V_H$-$V_H$ domains associated with a juxtaposed second pair of $V_L$-$V_L$ domains in the same polypeptide. The $V_H$-$V_H$ pair is connected with the $V_L$-$V_L$ pair by the linker $(G_2S)_6$.

| Polypeptide | Domain Specificities (N -> C) | Domain Order (N -> C) |
|---|---|---|
| 1 | CD30-CD30-CD16A-CD16A-CD16A-CD16A-CD19-CD19--His | VH-VL-VH-VH-VL-VL-VL-VH |

Polypeptide 1
(SEQ ID NO: 28)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSGGSGGSGGSDIVMTQSPK

FMSTSVGDRVTVTCKASQNVGTNVAWFQQKPGQSPKVLIYSASYRYSGVP

DRFTGSGSGTDFTLTISNVQSEDLAEYFCQQYHTYPLTFGGGTKLEINGG

SGGSGGSQVQLVQSGAEVKKPGESLKVSCKASGYTFTSYYMHWVRQAPGQ

GLEWMGIINPSGGSTSYAQKFQGRVTMTRDTSTSTVYMELSSLRSEDTAV

YYCARGSAYYYDFADYWGQGTLVTVSSGGSGGSGGSQVQLVQSGAEVKKP

GESLKVSCKASGYTFTSYYMHWVRQAPGQGLEWMGIINPSGGSTSYAQKF

QGRVTMTRDTSTSTVYMELSSLRSEDTAVYYCARGSAYYYDFADYWGQGT

LVTVSSGGSGGSGGSGGSGGSGGSSYVLTQPSSVSVAPGQTATISCGGHN

IGSKNVHWYQQRPGQSPVLVIYQDNKRPSGIPERFSGSNSGNTATLTISG

TQAMDEADYYCQVWDNYSVLFGGGTKLTVLGGSGGSGGSSYVLTQPSSVS

VAPGQTATISCGGHNIGSKNVHWYQQRPGQSPVLVIYQDNKRPSGIPERF

SGSNSGNTATLTISGTQAMDEADYYCQVWDNYSVLFGGGTKLTVLGGSGG

SGGSEVQLVQSGAEVKKPGESLKISCKGSGYSFTSNWIGWVRQMPGKGLE

WMGMIWPGDSDTMYSPSFQGQVTISADESINTAYLQWSSLKASDTAMYYC

ARRETTTVGRYYYAMDYWGQGTLVTVSSGGSGGSGGSGGSGGSGGSSYVL

TQPPSVSVAPGQTARITCGGNNIGSKTVHWYQQKPGQAPVLVVYDDSDRP

SGIPERFSGSNSGNTATLTISRVEAGDEADYYCQVGTDWSDHLQVFGGGT

KLTVLAAAGSHHHHHH p) A hexavalent tetravalent tetravalent, trispecific Fv antibody as shown in FIG. 4 having specificity for CD30, CD19 and CD16A and consisting of a single polypeptide having 12 variable domains and C-terminally a His-tag. The polypeptide comprises three single chain diabody units linked one after another.

| Polypeptide | Domain Specificities (N -> C) | Domain Order (N -> C) |
|---|---|---|
| 1 | CD30-CD30-CD30-CD30-CD16A-CD16A-CD16A-CD16A-CD19-CD19-CD19-CD19-His | VH-VL-VH-VL-VH-VH-VL-VL-VH-VL-VH-VL |

Polypeptide 1
(SEQ ID NO: 29)
QVQLQQSGAELARPGASVKMSCKASGYTFTTYTIHWVRQRPGHDLEWIGY

INPSSGYSDYNQNFKGKTTLTADKSSNTAYMQLNSLTSEDSAVYYCARRA

DYGNYEYTWFAYWGQGTTVTVSSGGSGGSGGSDIVMTQSPKFMSTSVGDR

VTVTCKASQNVGTNVAWFQQKPGQSPKVLIYSASYRYSGVPDRFTGSGSG

TDFTLTISNVQSEDLAEYFCQQYHTYPLTFGGGTKLEINGGSGGSGGSGG

SGGSGGSGGSQVQLQQSGAELARPGASVKMSCKASGYTFTTYTIHWVRQR

PGHDLEWIGYINPSSGYSDYNQNFKGKTTLTADKSSNTAYMQLNSLTSED

SAVYYCARRADYGNYEYTWFAYWGQGTTVTVSSGGSGGSGGSDIVMTQSP

KFMSTSVGDRVTVTCKASQNVGTNVAWFQQKPGQSPKVLIYSASYRYSGV

PDRFTGSGSGTDFTLTISNVQSEDLAEYFCQQYHTYPLTFGGGTKLEING

GSGGSGGSQVQLVQSGAEVKKPGESLKVSCKASGYTFTSYYMHWVRQAPG

QGLEWMGIINPSGGSTSYAQKFQGRVTMTRDTSTSTVYMELSSLRSEDTA

VYYCARGSAYYYDFADYWGQGTLVTVSSGGSGGSGGSQVQLVQSGAEVKK

PGESLKVSCKASGYTFTSYYMHWVRQAPGQGLEWMGIINPSGGSTSYAQK

FQGRVTMTRDTSTSTVYMELSSLRSEDTAVYYCARGSAYYYDFADYWGQG

TLVTVSSGGSGGSGGSGGSGGSGGSSYVLTQPSSVSVAPGQTATISCGGH

NIGSKNVHWYQQRPGQSPVLVIYQDNKRPSGIPERFSGSNSGNTATLTIS

GTQAMDEADYYCQVWDNYSVLFGGGTKLTVLGGSGGSGGSSYVLTQPSSV

SVAPGQTATISCGGHNIGSKNVHWYQQRPGQSPVLVIYQDNKRPSGIPER

FSGSNSGNTATLTISGTQAMDEADYYCQVWDNYSVLFGGGTKLTVLGGSG

GSGGSEVQLVQSGAEVKKPGESLKISCKGSGYSFTSNWIGWVRQMPGKGL

-continued
```
EWMGMIWPGDSDTMYSPSFQGQVTISADESINTAYLQWSSLKASDTAMYY

CARRETTTVGRYYYAMDYWGQGTLVTVSSGGSGGSGGSSYVLTQPPSVSV

APGQTARITCGGNNIGSKTVHWYQQKPGQAPVLVVYDDSDRPSGIPERFS

GSNSGNTATLTISRVEAGDEADYYCQVGTDWSDHLQVFGGGTKLTVLGGS

GGSGGSGGSGGSGGSGGSEVQLVQSGAEVKKPGESLKISCKGSGYSFTSN

WIGWVRQMPGKGLEWMGMIWPGDSDTMYSPSFQGQVTISADESINTAYLQ

WSSLKASDTAMYYCARRETTTVGRYYYAMDYWGQGTLVTVSSGGSGGSGG

SSYVLTQPPSVSVAPGQTARITCGGNNIGSKTVHWYQQKPGQAPVLVVYD

DSDRPSGIPERFSGSNSGNTATLTISRVEAGDEADYYCQVGTDWSDHLQV

FGGGTKLTVLAAAGSHHHHHH
```

Example 4

Assessment of Cell-Binding and Cytotoxic Activity Mediated by Trispecific Antibody Molecules

Study Procedures:

Cells and Cell Culture

CD19$^+$/CD30$^+$ MEC-1 (DSMZ, cat.: ACC 497), CD19$^+$/CD30$^-$ Raji (DSMZ, cat.: ACC 319), and CD19$^-$/CD30$^+$ KARPAS-299 (DSMZ, cat.: ACC 31) cells were cultured under standard conditions in RPMI 1640 (cat.: 21875-034) or IMDM (cat.: 12440-053) medium supplemented with 10% heat-inactivated fetal calf serum (FCS) (cat.: 10270-106), 100 U/mL penicillin G, 100 µg/mL streptomycin (cat: 1540-122), and 2 mM L-glutamine (cat: 25030-024; all Invitrogen, Karlsruhe, Germany) herein referred to as complete RPMI medium, as recommended by the supplier of the cell lines.

PBMCs were isolated from healthy volunteers' buffy coats (German Red Cross, Mannheim, Germany) by density gradient centrifugation. The buffy coat samples were diluted with a two-to-threefold volume of PBS (Invitrogen, cat.: 14190-169), layered on a cushion of Histopaque-1077 (Stemcell Technologies, cat.: 07861), and centrifuged at 800×g for 25 min at room temperature without brake. PBMC located at the interface were collected and washed 3 times with PBS before they were used for the enrichment of NK cells. NK cells were enriched from the PBMC population using the EasySep™ Human NK Cell Enrichment Kit Stemcell Technologies, cat.: 19055) for the immunomagnetic isolation of untouched human NK cells and the Big Easy EasySep™ Magnet according to the manufacturer's instructions.

Cell-Binding Assays and Flow Cytometric Analysis

Aliquots of the indicated cell lines were incubated with 100 L of serial dilutions of His-tagged antibodies in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min on ice. Staining of NK-cells was performed in FACS buffer supplemented with 1 mg/mL polyclonal human antibody (Gammanorm, Octapharma, Langenfeld, Germany, cat.: PZN-2451445) to block binding of antibodies to Fc☐ receptors.

After repeated washing with FACS buffer, cell-bound antibodies were detected with 10 µg/mL anti-His mAb 13/45/31-2 (Dianova, Hamburg, Germany, cat.: DIA910-1MG) followed by 15 µg/mL FITC-conjugated goat anti-mouse antibody (Dianova, cat.: 115-095-062). The cells were then washed again and resuspended in 0.2 mL of FACS buffer containing 2 µg/mL propidium iodide (PI) (Sigma, cat.: P4170) in order to exclude dead cells. The fluorescence of 2-5×10$^3$ living cells was measured using a Beckman-Coulter FC500 MPL flow cytometer using the MXP software (Beckman-Coulter, Krefeld, Germany) or a Millipore Guava EasyCyte flow cytometer (Merck Millipore, Schwalbach, Germany). Mean fluorescence intensities of the cell samples were calculated using CXP software (Beckman-Coulter) or Incyte software (Merck Millipore, Schwalbach, Germany). After subtracting the fluorescence intensity values of the cells stained with the secondary and tertiary reagents alone, the values were used for analysis using the GraphPad Prism (GraphPad Prism version 6.00 for Windows, GraphPad Software, La Jolla Calif. USA). For the calculation of $K_D$, the equation for one-site-binding (hyperbolic) was used.

Cytotoxicity Assay

For the calcein-release cytotoxicity assay, target cells were labeled with 10 µM calcein AM (Invitrogen, cat.: C3100MP) for 30 min in RPMI 1640 medium at 37° C., washed, and 1×10$^4$ cells were seeded, in individual wells of a 96-well micro plate, together with effector cells in a total volume of 200 µL at an effector-to-target (E:T) ratio of 5:1 in the presence of increasing antibody concentrations. After incubation for the indicated time periods at 37° C. in a humidified 5% CO$_2$ atmosphere, the fluorescence (F) of calcein released into the supernatant was measured by a plate reader at 520 nm (Victor 3, Perkin Elmer, Turku Finland, cat.: 1420-012). The specific cell lysis was calculated as: [F(sample)−F(spontaneous)]/[F(maximum)−F(spontaneous)]×100%. F(spontaneous) represents fluorescence released from target cells in the absence of effector cells and antibodies, and F(maximum) represents that released after total cell lysis induced by addition of 1% Triton X 100 (Roth, Karlsruhe, Germany, cat.: 3051.2). Regression curves were fit to calculate EC$_{50}$ (GraphPad Prism version 6.00 for Windows, GraphPad Software, La Jolla Calif. USA).

Activity of Trispecific Antibody Molecules

Figure 12:
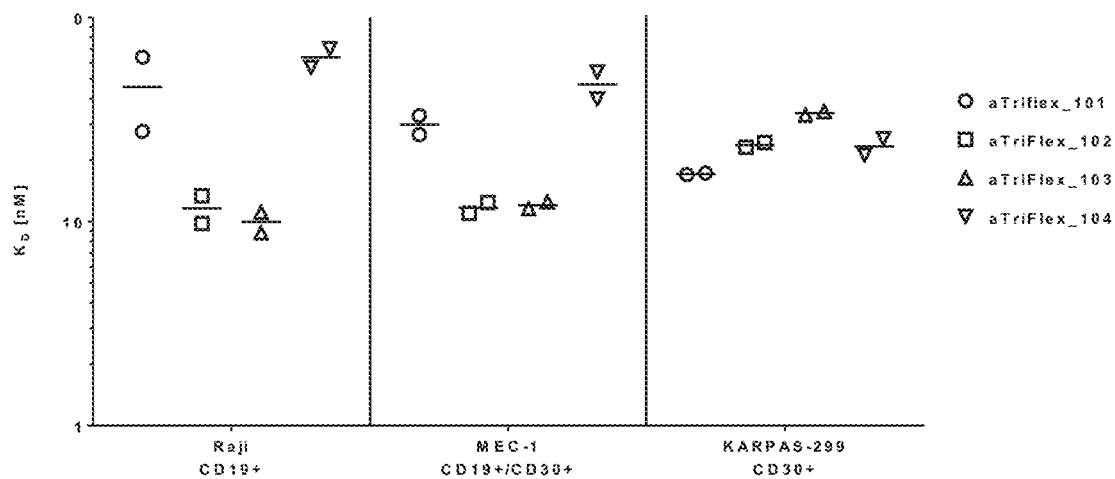
FIG. 12 shows binding of trispecific antibody molecules to single- or double-positive cell lines. Single-positive CD19+/CD30− Raji and CD19−/CD30+ KARPAS-299 cells as well as double-positive CD19+/CD30+ MEC-1 were stained with serial dilutions of the trispecific antibody molecules and cell surface bound antibodies were detected by mAb anti-His followed by FITC-conjugated goat anti-mouse IgG. Mean fluorescence intensities determined by flow cytometry were used to calculate $K_D$ values by non-linear regression. $K_D$ values for trispecific antibody molecules were determined in two independent experiments.

Binding of the trispecific antibody molecules, aTriFlex_101, aTriFlex_102, aTriFlex_103 and aTriFlex_104 described in Example 3, representing a trispecific antibody molecule as illustrated in FIG. 2 comprising the same antibody variable domains arranged in different orientations (see Example 3a), 3b), 3c) and 3d)) was demonstrated on single positive CD19+/CD30− Raji and CD19−/CD30+ KARPAS-299 cells as well as to double-positive CD19+/CD30+ MEC-1 cells using flow cytometry. Dissociation constants for CD19 were in the range of 6 to 64 nM and for CD30 between 16 and 45 nM (FIG. 12). On double-positive MEC-1 cells dissociation constants in the range of 9 to 47 nM were observed, generally confirming the data obtained for single-positive Raji and KARPAS-299 cells, respectively.

Figure 13:
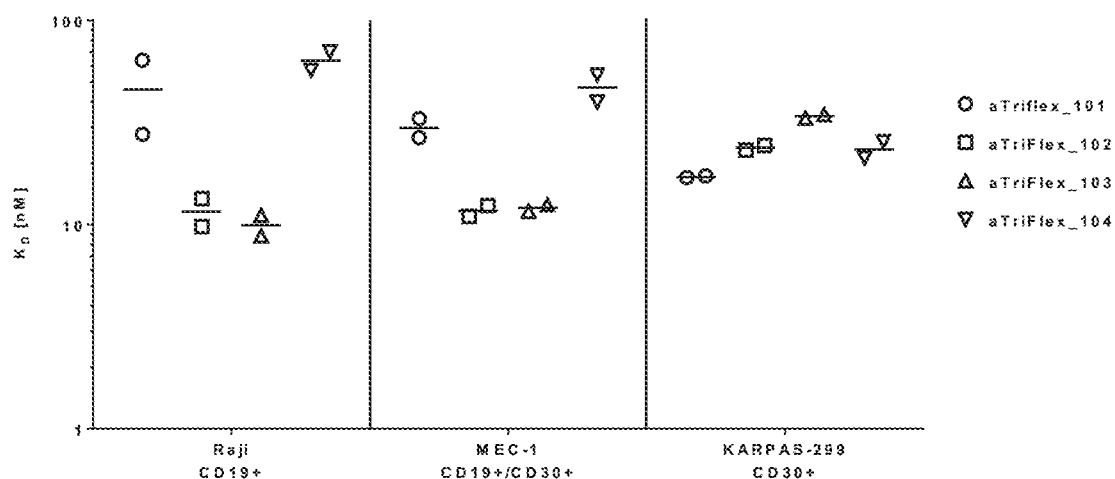
FIG. 13 shows cytotoxic activity of trispecific antibody molecules on single- or double-positive target cell lines. 4 h calcein-release cytotoxicity assays were performed on single-positive CD19+/CD30− Raji and CD19−/CD30+ KARPAS-299 cells as well as double-positive CD19+/CD30+ MEC-1 target cells with enriched NK-cells as effector cells in the presence of serial dilutions of the indicated trispecific antibody molecules. The fluorescent calcein released from lysed target cells was used to calculate antibody-mediated target cell lysis and modelling of sigmoidal dose-response curves for the determination of $EC_{50}$ values by non-linear regression. $EC_{50}$ values for aTriFlex constructs were determined in two independent experiments and plotted.

In cytotoxicity assays EC$_{50}$ values in the range of 89-580 pM on single positive CD30+/CD19-Raji and 155-952 pM on CD19-/CD30+ KARPAS-299 cells were observed. On double-positive CD19+/CD30+ MEC-1 cells EC$_{50}$ values in the range of 67-235 pM were observed indicating up to 11-fold improvement in activity (FIG. 13).

Overall, trispecific antibody molecules showed similar activity on the cell lines tested in this study; however, for other antigen pairs the influence of antigen density and geometry on the cell surface may have stronger impact on the activity of the constructs leading to a more pronounced increase in apparent affinity on double-positive cells compared to single-positive cells.

The invention is further described by the following numbered paragraphs:

1. A multivalent Fv antibody comprising a diabody-unit consisting of two pairs of variable domains, wherein one pair is a pair of variable light chain domains ($V_L$-$V_L$) linked one after another in a polypeptide and the other pair is a pair of variable heavy chains ($V_H$-$V_H$) linked one after another in a polypeptide, wherein the $V_L$-$V_L$ pair and the $V_H$-$V_H$ pair associate to two antigen binding sites and at least one pair of variable domains is linked in a polypeptide comprising at least four variable domains to at least two further variable domains, wherein one of said further variable domains is located N-terminally to said pair of variable domains and the other further variable domain is located C-terminally to said pair of variable domains in the polypeptide.

2. The multivalent Fv antibody according to paragraph 1, wherein the Fv antibody is at least tetravalent.

3. The multivalent Fv antibody according to paragraph 2, wherein the $V_L$-$V_L$ pair and the $V_H$-$V_H$ pair of the diabody-unit associate to two antigen binding sites and the further N-terminally located variable domain associates with a corresponding variable domain to a third antigen binding site and the C-terminally located variable domain associates with a corresponding variable domain to a fourth antigen-binding site.

4. The multivalent Fv antibody according to paragraph 2 comprising a polypeptide having at least six variable domains linked one after another, wherein a pair of variable domains of the diabody-unit (1, 1c, 10, 10a) is integrated into said polypeptide.

5. The multivalent Fv antibody according to any one of paragraphs 1 to 4, wherein the two variable domains in the pair of variable domains $V_L$-$V_L$ and the pair of variable domains $V_H$-$V_H$ are linked by a peptide linker (3, 3a) consisting of 12 or less amino acid residues.

6. The multivalent Fv antibody according to any one of paragraphs 1 to 5, wherein the antibody is heptavalent or hexavalent.

7. The multivalent Fv antibody molecule according to any one of paragraphs 1 to 6, wherein said pair of two variable domains of the diabody-unit in the polypeptide having at least six variable domains is associated with another pair of two variable domains of said polypeptide.

8. The multivalent Fv antibody molecule according to any one of paragraphs 1 to 7, wherein said pair of variable domains of the diabody-unit in the polypeptide is non-covalently associated with another pair of variable domains of another polypeptide.

9. The multivalent Fv antibody molecule according to paragraph 8, wherein said other polypeptide comprises at least two variable domains.

10. The multivalent Fv antibody molecule according to any one of paragraphs 1 to 9, wherein said polypeptide having at least six variable domains comprises a scFv-unit at its N-terminus and a scFv-unit at its C-terminus.

11. The multivalent Fv antibody molecule according to any one of paragraphs 1 to 9, wherein said polypeptide having at least six variable domains comprises a single chain diabody-unit at its N-terminus and a single chain diabody-unit at its C-terminus.

12. The multivalent Fv antibody molecule according to paragraph 10, wherein said Fv antibody molecule consists of a single polypeptide.

13. The multivalent Fv antibody molecule according to paragraph 11, wherein said Fv antibody molecule consists of a first polypeptide comprising ten variable domains and a second polypeptide comprising two variable domains, wherein the first polypeptide comprises a single chain diabody unit at the N-terminus and a single chain diabody unit at the C-terminus and the second polypeptide is associated with the first polypeptide to a diabody unit.

14. The multivalent Fv antibody molecule according to paragraph 8 or 9, wherein said polypeptide has six variable domains linked one after another from the N-terminus to the C-terminus, a first and a second variable domain forming a scFv-unit at the N-terminus, said scFv-unit at the N-terminus is linked C-terminally to a third variable domain, said third variable domain is linked by a peptide linker consisting of 12 or less amino acid residues to a fourth variable domain, said fourth variable domain is linked C-terminally to a scFv-unit at the C-terminus and said scFv-unit is formed by a fifth and sixth variable domain.

15. The multivalent Fv antibody molecule according to paragraph 7, wherein said polypeptide has eight variable domains linked one after another from the N-terminus to the C-terminus, a first and a second variable domain forming a scFv-unit at the N-terminus, said scFv-unit at the N-terminus is linked C-terminally to a third variable domain, said third variable domain is linked by a peptide linker consisting of 12 or less amino acid residues to a fourth variable domain, said fourth variable domain is linked C-terminally to a fifth variable domain, said fifth variable domain is linked C-terminally to a sixth variable domain by a linker consisting of 12 or less amino acid residues, said sixth variable domain is linked C-terminally to a scFv-unit at the C-terminus and said scFv-unit is formed by a seventh and a eight variable domain.

16. The multivalent Fv antibody molecule according to paragraph 1, wherein the pair of variable light chain domains ($V_L$-$V_L$) is linked in a first polypeptide comprising at least four variable domains to another variable domain N-terminally and to another variable domain C-terminally and the pair of variable heavy chains ($V_H$-$V_H$) is linked in a second polypeptide comprising at least four variable domains to another variable domain N-terminally and to another variable domain C-terminally.

17. The multivalent Fv antibody according to paragraph 16, wherein the first and the second polypeptides comprise six variable domains and each of the polypeptides comprises a scFv unit C-terminally or N-terminally.

18. The multivalent Fv antibody molecule according to any one of paragraphs 1 to 17, wherein said variable domains in said diabody-unit have the same epitope specificity or different epitope specificities.

19. The multivalent Fv antibody molecule according to any one of paragraphs 1 to 18, wherein the Fv antibody molecule has a specificity for an antigen present on an immune effector cell.

20. The multivalent Fv antibody molecule according to paragraph 19, wherein the Fv antibody comprises two antigen binding sites having specificity to the same kind of immune effector cell.

21. The multivalent Fv antibody molecule according to any one of paragraphs 1 to 20, wherein the Fv antibody comprises at least one specificity for a tumor antigen.

22. The multivalent Fv antibody molecule according to paragraph 21, wherein the Fv antibody comprises specificities for two tumor antigens.

23. The multivalent Fv antibody molecule according to any one of paragraphs 19 to 22, wherein the Fv antibody comprises at least one specificity for a viral antigen.

24. The multivalent Fv antibody according to paragraph 7, wherein said polypeptide having at least six variable domains is associated with another polypeptide having at least six variable domains.

25. The multivalent Fv antibody according to any one of paragraphs 1 to 24 for use as a medicament.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A trispecific and tetravalent Fv antibody comprising a, first polypeptide consisting of six variable domains and a second polypeptide consisting of two variable domains,
wherein the first polypeptide comprises a first and a second variable domain forming a scFv-unit at the N-terminus,
said scFv-unit at the N-terminus is linked C-terminally to a third variable domain,
said third variable domain is linked C-terminally to a fourth variable domain,
said fourth variable domain is linked to a scFv-unit at the C-terminus, and
said scFv-unit is formed by a fifth and sixth variable domain, wherein the third and fourth variable domains of the first polypeptide associate with the two variable domains of the second polypeptide to form a diabody unit consisting of two pairs of variable domains,
wherein one pair is a pair of variable light chain domains ($V_L$-$V_L$),
the other pair is a pair of variable heavy chains ($V_H$-$V_H$) and
the diabody consists of two antigen binding sites and both antigen binding sites bind an antigen present on an immune effector cell.

2. The trispecific and tetravalent Fv antibody according to claim 1, wherein the two variable domains in the pair of variable domains $V_L$-$V_L$ and the pair of variable domains $V_H$-$V_H$ are linked by a peptide linker consisting of 12 or less amino acid residues.

3. A trispecific and tetravalent Fv antibody comprising a diabody-unit consisting of two pairs of variable domains, wherein one pair is a pair of variable light chain domains ($V_L$-$V_L$), the other pair is a pair of variable heavy chains ($V_H$-$V_H$) and the diabody consists of two antigen binding sites and both antigen binding sites bind an antigen present on an immune effector cell, wherein one pair of variable domains is in a polypeptide comprising variable domains linked one after another, wherein said pair of two variable domains of the diabody-unit in the polypeptide comprising variable domains is associated with another pair of two variable domains of the polypeptide, wherein the polypeptide has eight variable domains linked one after another from the N-terminus to the C-terminus comprising, a first and a second variable domain forming a scFv-unit at the N-terminus,
said scFv-unit at the N-terminus is linked C-terminally to a third variable domain,
said third variable domain is linked by a peptide linker consisting of 12 or less amino acid residues to a fourth variable domain,
said fourth variable domain is linked C-terminally to a fifth variable domain, said fifth variable domain is linked C-terminally to a sixth variable domain by a linker consisting of 12 or less amino acid residues, said sixth variable domain is linked C-terminally to a scFv-unit at the C-terminus and said scFv-unit is formed by a seventh and an eight variable domain.

4. A trispecific Fv antibody molecule comprising a diabody-unit consisting of two pairs of variable domains, wherein one pair is a pair of variable light chain domains ($V_L$-$V_L$) and the other pair is a pair of variable heavy chains ($V_H$-$V_H$) and the diabody consists of two antigen binding sites and both antigen binding sites bind an antigen present on an immune effector cell, wherein one pair of variable domains is in a polypeptide consisting of ten variable domains linked one after another and said one pair of juxtaposed variable domains is associated with the other pair of juxtaposed variable domains in a second polypeptide which consists of two variable domains, wherein the first polypeptide comprises a single chain diabody-unit at its N-terminus and a single chain diabody-unit at its C-terminus.

5. The trispecific and tetravalent Fv antibody molecule according to claim 1,
wherein
a Tag sequence is fused to the first polypeptide and a different Tag sequence is fused to the second polypeptide.

6. The multivalent Fv antibody molecule according to claim 3, wherein said polypeptide has eight variable domains linked one after another from the N-terminus to the C-terminus, a first and a second variable domain forming a scFv-unit at the N-terminus, said scFv-unit at the N-terminus is linked C-terminally to a third variable domain, said third variable domain is linked by a peptide linker consisting of 12 or less amino acid residues to a fourth variable domain, said fourth variable domain is linked C-terminally to a fifth variable domain, said fifth variable domain is linked C-terminally to a sixth variable domain by a linker consisting of 12 or less amino acid residues, said sixth variable domain is linked C-terminally to a scFv-unit at the C-terminus and said scFv-unit is formed by a seventh and a eight variable domain.

7. The trispecific and tetravalent Fv antibody molecule according to claim 1, wherein said variable domains in said diabody-unit have the same epitope specificity or different epitope specificities.

8. The trispecific and tetravalent Fv antibody molecule according to claim 1, wherein the immune effector cell is selected from the group consisting of T cell, natural killer (NK) cell, gamma delta (gd) T cell, natural killer T (NKT) cell, granulocyte, monocyte, macrophage, dendritic cell, innate lymphoid cell (ILC) and antigen presenting cell.

9. The trispecific and tetravalent Fv antibody molecule according to claim 1, wherein the Fv antibody comprises at least one specificity for a tumor antigen.

10. The trispecific and tetravalent Fv antibody molecule according to claim 9, wherein the Fv antibody comprises specificities for two tumor antigens.

11. The trispecific and tetravalent Fv antibody molecule according to claim 1, wherein the Fv antibody comprises at least one specificity for a viral antigen.

12. A medicament comprising the trispecific and tetravalent Fv antibody according to claim 1.

13. The trispecific and tetravalent Fv antibody molecule according to claim 8, wherein the antigen is selected from the group consisting of CD3, CD16 and CD16A.

14. The trispecific and tetravalent Fv antibody according to claim 1, wherein the variable domains are arranged from the N-terminus to the C-terminus in an orientation selected from:
- (a) $V_H\text{-}V_L\text{-}V_H\text{-}V_H\text{-}V_L\text{-}V_H$ (first polypeptide) and $V_L\text{-}V_L$ (second polypeptide);
- (b) $V_L\text{-}V_H\text{-}V_H\text{-}V_H\text{-}V_H\text{-}V_L$ (first polypeptide) and $V_L\text{-}V_L$ (second polypeptide);
- (c) $V_H\text{-}V_L\text{-}V_L\text{-}V_L\text{-}V_H\text{-}V_L$ (first polypeptide) and $V_H\text{-}V_H$ (second polypeptide);
- (d) $V_L\text{-}V_H\text{-}V_L\text{-}V_L\text{-}V_H\text{-}V_L$ (first polypeptide) and $V_H\text{-}V_H$ (second polypeptide); or
- (e) $V_H\text{-}V_L\text{-}V_L\text{-}V_L\text{-}V_L\text{-}V_H$ (first polypeptide) and $V_H\text{-}V_H$ (second polypeptide).

15. The trispecific and tetravalent Fv antibody molecule according to claim 9, wherein the antibody molecule has an antigen-binding site specific for an antigen epitope on a soluble protein selected from the group consisting of growth factors, cytokines, chemokines, mitogens and albumins.

16. The trispecific and tetravalent Fv antibody molecule according to claim 5, wherein the Tag sequences are selected from the group consisting of a His-Tag and SEQ ID NOs: 38-40.

17. The trispecific and tetravalent Fv antibody molecule according to claim 16, wherein the Tag sequences are a His-Tag and SEQ ID NO: 38.

18. The trispecific and tetravalent Fv antibody molecule according to claim 5, wherein the Fv antibody comprises at least one specificity for a tumor antigen.

19. The trispecific and tetravalent Fv antibody molecule according to claim 18, wherein the Fv antibody comprises specificities for two tumor antigens.

20. The trispecific and tetravalent Fv antibody molecule according to claim 5, wherein the immune effector cell is selected from the group consisting of T cell, natural killer (NK) cell, gamma delta (gd) T cell, natural killer T (NKT) cell, granulocyte, monocyte, macrophage, dendritic cell, innate lymphoid cell (ILC) and antigen presenting cell.

21. The trispecific and tetravalent Fv antibody molecule according to claim 20, wherein the antigen is selected from the group consisting of CD3, CD16 and CD16A.

22. The trispecific and tetravalent Fv antibody according to claim 5, wherein the variable domains are arranged from the N-terminus to the C-terminus in an orientation selected from:
- (a) $V_H\text{-}V_L\text{-}V_H\text{-}V_H\text{-}V_L\text{-}V_H$ (first polypeptide) and $V_L\text{-}V_L$ (second polypeptide);
- (b) $V_L\text{-}V_H\text{-}V_H\text{-}V_H\text{-}V_H\text{-}V_L$ (first polypeptide) and $V_L\text{-}V_L$ (second polypeptide);
- (c) $V_H\text{-}V_L\text{-}V_L\text{-}V_L\text{-}V_H\text{-}V_L$ (first polypeptide) and $V_H\text{-}V_H$ (second polypeptide);
- (d) $V_L\text{-}V_H\text{-}V_L\text{-}V_L\text{-}V_H\text{-}V_L$ (first polypeptide) and $V_H\text{-}V_H$ (second polypeptide); or
- (e) $V_H\text{-}V_L\text{-}V_L\text{-}V_L\text{-}V_L\text{-}V_H$ (first polypeptide) and $V_H\text{-}V_H$ (second polypeptide).

23. The trispecific Fv antibody molecule according to claim 4, wherein the diabody consists of two antigen binding sites and both antigen binding sites bind an antigen present on an immune effector cell.

24. The trispecific Fv antibody molecule according to claim 23, wherein the immune effector cell is selected from the group consisting of T cell, natural killer (NK) cell, gamma delta (gd) T cell, natural killer T (NKT) cell, granulocyte, monocyte, macrophage, dendritic cell, innate lymphoid cell (ILC) and antigen presenting cell.

25. The trispecific Fv antibody molecule according to claim 24, wherein the antigen is selected from the group consisting of CD3, CD16 and CD16A.

* * * * *

SEQUENCE LISTING

```
<160> NUMBER OF SEQ ID NOS: 40

<210> SEQ ID NO 1
<211> LENGTH: 780
<212> TYPE: PRT
<213> ORGANISM: artificial sequence
<220> FEATURE:
<223> OTHER INFORMATION: Fv polypeptide

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Gln Val Gln Leu Val Gln Ser Gly Ala Glu Val Lys Lys Pro Gly
            260                 265                 270

Glu Ser Leu Lys Val Ser Cys Lys Ala Ser Gly Tyr Thr Phe Thr Ser
        275                 280                 285

Tyr Tyr Met His Trp Val Arg Gln Ala Pro Gly Gln Gly Leu Glu Trp
    290                 295                 300

Met Gly Ile Ile Asn Pro Ser Gly Gly Ser Thr Ser Tyr Ala Gln Lys
305                 310                 315                 320
```

```
Phe Gln Gly Arg Val Thr Met Thr Arg Asp Thr Ser Thr Val
            325                 330                 335

Tyr Met Glu Leu Ser Ser Leu Arg Ser Glu Asp Thr Ala Val Tyr Tyr
            340                 345                 350

Cys Ala Arg Gly Ser Ala Tyr Tyr Asp Phe Ala Asp Tyr Trp Gly
            355                 360                 365

Gln Gly Thr Leu Val Thr Val Ser Ser Gly Gly Ser Gly
            370                 375             380

Gly Ser Gln Val Gln Leu Val Gln Ser Gly Ala Glu Val Lys Lys Pro
385                 390                 395                 400

Gly Glu Ser Leu Lys Val Ser Cys Lys Ala Ser Gly Tyr Thr Phe Thr
                405                 410                 415

Ser Tyr Tyr Met His Trp Val Arg Gln Ala Pro Gly Gln Gly Leu Glu
            420                 425                 430

Trp Met Gly Ile Ile Asn Pro Ser Gly Gly Ser Thr Ser Tyr Ala Gln
            435                 440                 445

Lys Phe Gln Gly Arg Val Thr Met Thr Arg Asp Thr Ser Thr Ser Thr
450                 455                 460

Val Tyr Met Glu Leu Ser Ser Leu Arg Ser Glu Asp Thr Ala Val Tyr
465                 470                 475                 480

Tyr Cys Ala Arg Gly Ser Ala Tyr Tyr Asp Phe Ala Asp Tyr Trp
                485                 490                 495

Gly Gln Gly Thr Leu Val Thr Val Ser Ser Gly Gly Ser Gly Gly Ser
                500                 505                 510

Gly Gly Ser Ser Tyr Val Leu Thr Gln Pro Pro Ser Val Ser Val Ala
            515                 520                 525

Pro Gly Gln Thr Ala Arg Ile Thr Cys Gly Gly Asn Asn Ile Gly Ser
530                 535                 540

Lys Thr Val His Trp Tyr Gln Gln Lys Pro Gly Gln Ala Pro Val Leu
545                 550                 555                 560

Val Val Tyr Asp Asp Ser Asp Arg Pro Ser Gly Ile Pro Glu Arg Phe
                565                 570                 575

Ser Gly Ser Asn Ser Gly Asn Thr Ala Thr Leu Thr Ile Ser Arg Val
                580                 585                 590

Glu Ala Gly Asp Glu Ala Asp Tyr Tyr Cys Gln Val Gly Thr Asp Trp
                595                 600                 605

Ser Asp His Leu Gln Val Phe Gly Gly Gly Thr Lys Leu Thr Val Leu
            610                 615                 620

Gly Gly Ser Gly Gly Ser Gly Gly Ser Gly Gly Ser Gly Gly Ser Gly
625                 630                 635                 640

Gly Ser Gly Gly Ser Glu Val Gln Leu Val Gln Ser Gly Ala Glu Val
                645                 650                 655

Lys Lys Pro Gly Glu Ser Leu Lys Ile Ser Cys Lys Gly Ser Gly Tyr
            660                 665                 670

Ser Phe Thr Ser Asn Trp Ile Gly Trp Val Arg Gln Met Pro Gly Lys
            675                 680                 685

Gly Leu Glu Trp Met Gly Met Ile Trp Pro Gly Asp Ser Asp Thr Met
            690                 695                 700

Tyr Ser Pro Ser Phe Gln Gly Gln Val Thr Ile Ser Ala Asp Glu Ser
705                 710                 715                 720

Ile Asn Thr Ala Tyr Leu Gln Trp Ser Ser Leu Lys Ala Ser Asp Thr
                725                 730                 735
```

```
Ala Met Tyr Tyr Cys Ala Arg Arg Glu Thr Thr Thr Val Gly Arg Tyr
                740                 745                 750

Tyr Tyr Ala Met Asp Tyr Trp Gly Gln Gly Thr Leu Val Thr Val Ser
            755                 760                 765

Ser Ala Ala Ala Gly Ser His His His His His His
        770                 775                 780

<210> SEQ ID NO 2
<211> LENGTH: 234
<212> TYPE: PRT
<213> ORGANISM: artificial sequence
<220> FEATURE:
<223> OTHER INFORMATION: Fv polypeptide

<400> SEQUENCE: 2

Ser Tyr Val Leu Thr Gln Pro Ser Ser Val Ser Val Ala Pro Gly Gln
1               5                   10                  15

Thr Ala Thr Ile Ser Cys Gly Gly His Asn Ile Gly Ser Lys Asn Val
                20                  25                  30

His Trp Tyr Gln Gln Arg Pro Gly Gln Ser Pro Val Leu Val Ile Tyr
            35                  40                  45

Gln Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu Gly Gly Ser Gly Gly Ser
            100                 105                 110

Gly Gly Ser Ser Tyr Val Leu Thr Gln Pro Ser Ser Val Ser Val Ala
        115                 120                 125

Pro Gly Gln Thr Ala Thr Ile Ser Cys Gly Gly His Asn Ile Gly Ser
    130                 135                 140

Lys Asn Val His Trp Tyr Gln Gln Arg Pro Gly Gln Ser Pro Val Leu
145                 150                 155                 160

Val Ile Tyr Gln Asp Asn Lys Arg Pro Ser Gly Ile Pro Glu Arg Phe
                165                 170                 175

Ser Gly Ser Asn Ser Gly Asn Thr Ala Thr Leu Thr Ile Ser Gly Thr
            180                 185                 190

Gln Ala Met Asp Glu Ala Asp Tyr Tyr Cys Gln Val Trp Asp Asn Tyr
        195                 200                 205

Ser Val Leu Phe Gly Gly Gly Thr Lys Leu Thr Val Leu Ala Ala Ala
    210                 215                 220

Gly Ser Asp Tyr Lys Asp Asp Asp Lys
225                 230

<210> SEQ ID NO 3
<211> LENGTH: 780
<212> TYPE: PRT
<213> ORGANISM: artificial sequence
<220> FEATURE:
<223> OTHER INFORMATION: Fv polypeptide

<400> SEQUENCE: 3

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
                20                  25                  30
```

```
His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Gly Thr Asp Trp Ser Asp His
                 85                  90                  95

Leu Gln Val Phe Gly Gly Thr Lys Leu Thr Val Leu Gly Gly Ser
                100                 105                 110

Gly Gly Ser Gly Gly Ser Gly Ser Gly Gly Ser Gly Gly Ser Gly
            115                 120                 125

Gly Ser Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Asn Trp Ile Gly Trp Val Arg Gln Met Pro Gly Lys Gly Leu Glu
                165                 170                 175

Trp Met Gly Met Ile Trp Pro Gly Asp Ser Asp Thr Met Tyr Ser Pro
            180                 185                 190

Ser Phe Gln Gly Gln Val Thr Ile Ser Ala Asp Glu Ser Ile Asn Thr
                195                 200                 205

Ala Tyr Leu Gln Trp Ser Ser Leu Lys Ala Ser Asp Thr Ala Met Tyr
    210                 215                 220

Tyr Cys Ala Arg Arg Glu Thr Thr Val Gly Arg Tyr Tyr Tyr Ala
225                 230                 235                 240

Met Asp Tyr Trp Gly Gln Gly Thr Leu Val Thr Val Ser Ser Gly Gly
                245                 250                 255

Ser Gly Gly Ser Gly Gly Ser Gln Val Gln Leu Val Gln Ser Gly Ala
            260                 265                 270

Glu Val Lys Lys Pro Gly Glu Ser Leu Lys Val Ser Cys Lys Ala Ser
    275                 280                 285

Gly Tyr Thr Phe Thr Ser Tyr Tyr Met His Trp Val Arg Gln Ala Pro
290                 295                 300

Gly Gln Gly Leu Glu Trp Met Gly Ile Ile Asn Pro Ser Gly Gly Ser
305                 310                 315                 320

Thr Ser Tyr Ala Gln Lys Phe Gln Gly Arg Val Thr Met Thr Arg Asp
                325                 330                 335

Thr Ser Thr Ser Thr Val Tyr Met Glu Leu Ser Ser Leu Arg Ser Glu
            340                 345                 350

Asp Thr Ala Val Tyr Tyr Cys Ala Arg Gly Ser Ala Tyr Tyr Tyr Asp
            355                 360                 365

Phe Ala Asp Tyr Trp Gly Gln Gly Thr Leu Val Thr Val Ser Ser Gly
    370                 375                 380

Gly Ser Gly Gly Ser Gly Gly Ser Gln Val Gln Leu Val Gln Ser Gly
385                 390                 395                 400

Ala Glu Val Lys Lys Pro Gly Glu Ser Leu Lys Val Ser Cys Lys Ala
                405                 410                 415

Ser Gly Tyr Thr Phe Thr Ser Tyr Tyr Met His Trp Val Arg Gln Ala
            420                 425                 430

Pro Gly Gln Gly Leu Glu Trp Met Gly Ile Ile Asn Pro Ser Gly Gly
            435                 440                 445
```

```
Ser Thr Ser Tyr Ala Gln Lys Phe Gln Gly Arg Val Thr Met Thr Arg
    450                 455                 460
Asp Thr Ser Thr Ser Thr Val Tyr Met Glu Leu Ser Ser Leu Arg Ser
465                 470                 475                 480
Glu Asp Thr Ala Val Tyr Tyr Cys Ala Arg Gly Ser Ala Tyr Tyr Tyr
                485                 490                 495
Asp Phe Ala Asp Tyr Trp Gly Gln Gly Thr Leu Val Thr Val Ser Ser
            500                 505                 510
Gly Gly Ser Gly Gly Ser Gly Gly Ser Gln Val Gln Leu Gln Gln Ser
        515                 520                 525
Gly Ala Glu Leu Ala Arg Pro Gly Ala Ser Val Lys Met Ser Cys Lys
    530                 535                 540
Ala Ser Gly Tyr Thr Phe Thr Thr Tyr Thr Ile His Trp Val Arg Gln
545                 550                 555                 560
Arg Pro Gly His Asp Leu Glu Trp Ile Gly Tyr Ile Asn Pro Ser Ser
                565                 570                 575
Gly Tyr Ser Asp Tyr Asn Gln Asn Phe Lys Gly Lys Thr Thr Leu Thr
            580                 585                 590
Ala Asp Lys Ser Ser Asn Thr Ala Tyr Met Gln Leu Asn Ser Leu Thr
        595                 600                 605
Ser Glu Asp Ser Ala Val Tyr Tyr Cys Ala Arg Arg Ala Asp Tyr Gly
    610                 615                 620
Asn Tyr Glu Tyr Thr Trp Phe Ala Tyr Trp Gly Gln Gly Thr Thr Val
625                 630                 635                 640
Thr Val Ser Ser Gly Gly Ser Gly Gly Ser Gly Gly Ser Gly Gly Ser
                645                 650                 655
Gly Gly Ser Gly Gly Ser Asp Ile Val Met Thr Gln Ser Pro Lys Phe
            660                 665                 670
Met Ser Thr Ser Val Gly Asp Arg Val Thr Val Thr Cys Lys Ala Ser
        675                 680                 685
Gln Asn Val Gly Thr Asn Val Ala Trp Phe Gln Lys Pro Gly Gln
    690                 695                 700
Ser Pro Lys Val Leu Ile Tyr Ser Ala Ser Tyr Arg Tyr Ser Gly Val
705                 710                 715                 720
Pro Asp Arg Phe Thr Gly Ser Gly Ser Gly Thr Asp Phe Thr Leu Thr
                725                 730                 735
Ile Ser Asn Val Gln Ser Glu Asp Leu Ala Glu Tyr Phe Cys Gln Gln
            740                 745                 750
Tyr His Thr Tyr Pro Leu Thr Phe Gly Gly Gly Thr Lys Leu Glu Ile
        755                 760                 765
Asn Ala Ala Ala Gly Ser His His His His His His
    770                 775                 780

<210> SEQ ID NO 4
<211> LENGTH: 234
<212> TYPE: PRT
<213> ORGANISM: artificial sequence
<220> FEATURE:
<223> OTHER INFORMATION: Fv polypeptide

<400> SEQUENCE: 4

Ser Tyr Val Leu Thr Gln Pro Ser Ser Val Ser Val Ala Pro Gly Gln
1               5                   10                  15
Thr Ala Thr Ile Ser Cys Gly Gly His Asn Ile Gly Ser Lys Asn Val
                20                  25                  30
```

His Trp Tyr Gln Gln Arg Pro Gly Gln Ser Pro Val Leu Val Ile Tyr
            35                  40                  45

Gln Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Asn Tyr Ser Val Leu
                 85                  90                  95

Phe Gly Gly Gly Thr Lys Leu Thr Val Leu Gly Gly Ser Gly Gly Ser
            100                 105                 110

Gly Gly Ser Ser Tyr Val Leu Thr Gln Pro Ser Ser Val Ser Val Ala
        115                 120                 125

Pro Gly Gln Thr Ala Thr Ile Ser Cys Gly Gly His Asn Ile Gly Ser
130                 135                 140

Lys Asn Val His Trp Tyr Gln Gln Arg Pro Gly Gln Ser Pro Val Leu
145                 150                 155                 160

Val Ile Tyr Gln Asp Asn Lys Arg Pro Ser Gly Ile Pro Glu Arg Phe
                165                 170                 175

Ser Gly Ser Asn Ser Gly Asn Thr Ala Thr Leu Thr Ile Ser Gly Thr
            180                 185                 190

Gln Ala Met Asp Glu Ala Asp Tyr Tyr Cys Gln Val Trp Asp Asn Tyr
        195                 200                 205

Ser Val Leu Phe Gly Gly Gly Thr Lys Leu Thr Val Leu Ala Ala Ala
    210                 215                 220

Gly Ser Asp Tyr Lys Asp Asp Asp Lys
225                 230

<210> SEQ ID NO 5
<211> LENGTH: 752
<212> TYPE: PRT
<213> ORGANISM: artificial sequence
<220> FEATURE:
<223> OTHER INFORMATION: Fv polypeptide

<400> SEQUENCE: 5

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Thr Val
             20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Gly Thr Asp Trp Ser Asp His
                 85                  90                  95

Leu Gln Val Phe Gly Gly Gly Thr Lys Leu Thr Val Leu Gly Gly Ser
            100                 105                 110

Gly Gly Ser Gly Gly Ser Gly Gly Ser Gly Gly Ser Gly Gly Ser Gly
        115                 120                 125

Gly Ser Glu Val Gln Leu Val Gln Ser Gly Ala Glu Val Lys Lys Pro
130                 135                 140

Gly Glu Ser Leu Lys Ile Ser Cys Lys Gly Ser Gly Tyr Ser Phe Thr
145                 150                 155                 160

Ser Asn Trp Ile Gly Trp Val Arg Gln Met Pro Gly Lys Gly Leu Glu
            165                 170                 175

Trp Met Gly Met Ile Trp Pro Gly Asp Ser Asp Thr Met Tyr Ser Pro
            180                 185                 190

Ser Phe Gln Gly Gln Val Thr Ile Ser Ala Asp Glu Ser Ile Asn Thr
            195                 200                 205

Ala Tyr Leu Gln Trp Ser Ser Leu Lys Ala Ser Asp Thr Ala Met Tyr
            210                 215                 220

Tyr Cys Ala Arg Arg Glu Thr Thr Thr Val Gly Arg Tyr Tyr Tyr Ala
225                 230                 235                 240

Met Asp Tyr Trp Gly Gln Gly Thr Leu Val Thr Val Ser Ser Gly Gly
            245                 250                 255

Ser Gly Gly Ser Gly Gly Ser Ser Tyr Val Leu Thr Gln Pro Ser Ser
            260                 265                 270

Val Ser Val Ala Pro Gly Gln Thr Ala Thr Ile Ser Cys Gly Gly His
            275                 280                 285

Asn Ile Gly Ser Lys Asn Val His Trp Tyr Gln Gln Arg Pro Gly Gln
            290                 295                 300

Ser Pro Val Leu Val Ile Tyr Gln Asp Asn Lys Arg Pro Ser Gly Ile
305                 310                 315                 320

Pro Glu Arg Phe Ser Gly Ser Asn Ser Gly Asn Thr Ala Thr Leu Thr
            325                 330                 335

Ile Ser Gly Thr Gln Ala Met Asp Glu Ala Asp Tyr Tyr Cys Gln Val
            340                 345                 350

Trp Asp Asn Tyr Ser Val Leu Phe Gly Gly Gly Thr Lys Leu Thr Val
            355                 360                 365

Leu Gly Gly Ser Gly Gly Ser Gly Gly Ser Ser Tyr Val Leu Thr Gln
            370                 375                 380

Pro Ser Ser Val Ser Val Ala Pro Gly Gln Thr Ala Thr Ile Ser Cys
385                 390                 395                 400

Gly Gly His Asn Ile Gly Ser Lys Asn Val His Trp Tyr Gln Gln Arg
            405                 410                 415

Pro Gly Gln Ser Pro Val Leu Val Ile Tyr Gln Asp Asn Lys Arg Pro
            420                 425                 430

Ser Gly Ile Pro Glu Arg Phe Ser Gly Ser Asn Ser Gly Asn Thr Ala
            435                 440                 445

Thr Leu Thr Ile Ser Gly Thr Gln Ala Met Asp Glu Ala Asp Tyr Tyr
            450                 455                 460

Cys Gln Val Trp Asp Asn Tyr Ser Val Leu Phe Gly Gly Gly Thr Lys
465                 470                 475                 480

Leu Thr Val Leu Gly Gly Ser Gly Gly Ser Gly Gly Ser Gln Val Gln
            485                 490                 495

Leu Gln Gln Ser Gly Ala Glu Leu Ala Arg Pro Gly Ala Ser Val Lys
            500                 505                 510

Met Ser Cys Lys Ala Ser Gly Tyr Thr Phe Thr Thr Tyr Thr Ile His
            515                 520                 525

Trp Val Arg Gln Arg Pro Gly His Asp Leu Glu Trp Ile Gly Tyr Ile
            530                 535                 540

Asn Pro Ser Ser Gly Tyr Ser Asp Tyr Asn Gln Asn Phe Lys Gly Lys
545                 550                 555                 560

Thr Thr Leu Thr Ala Asp Lys Ser Ser Asn Thr Ala Tyr Met Gln Leu
            565                 570                 575

Asn Ser Leu Thr Ser Glu Asp Ser Ala Val Tyr Tyr Cys Ala Arg Arg

-continued

```
                   580                 585                 590
Ala Asp Tyr Gly Asn Tyr Glu Tyr Thr Trp Phe Ala Tyr Trp Gly Gln
                595                 600                 605

Gly Thr Thr Val Thr Val Ser Ser Gly Gly Ser Gly Gly Ser Gly Gly
610                 615                 620

Ser Gly Gly Ser Gly Gly Ser Gly Gly Ser Asp Ile Val Met Thr Gln
625                 630                 635                 640

Ser Pro Lys Phe Met Ser Thr Ser Val Gly Asp Arg Val Thr Val Thr
                645                 650                 655

Cys Lys Ala Ser Gln Asn Val Gly Thr Asn Val Ala Trp Phe Gln Gln
                660                 665                 670

Lys Pro Gly Gln Ser Pro Lys Val Leu Ile Tyr Ser Ala Ser Tyr Arg
                675                 680                 685

Tyr Ser Gly Val Pro Asp Arg Phe Thr Gly Ser Gly Ser Gly Thr Asp
                690                 695                 700

Phe Thr Leu Thr Ile Ser Asn Val Gln Ser Glu Asp Leu Ala Glu Tyr
705                 710                 715                 720

Phe Cys Gln Gln Tyr His Thr Tyr Pro Leu Thr Phe Gly Gly Gly Thr
                725                 730                 735

Lys Leu Glu Ile Asn Ala Ala Ala Gly Ser His His His His His His
                740                 745                 750

<210> SEQ ID NO 6
<211> LENGTH: 262
<212> TYPE: PRT
<213> ORGANISM: artificial sequence
<220> FEATURE:
<223> OTHER INFORMATION: Fv polypeptide

<400> SEQUENCE: 6

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Asp Phe Ala Asp Tyr Trp Gly Gln
                100                 105                 110

Gly Thr Leu Val Thr Val Ser Ser Gly Gly Ser Gly Gly Ser Gly Gly
            115                 120                 125

Ser Gln Val Gln Leu Val Gln Ser Gly Ala Glu Val Lys Lys Pro Gly
        130                 135                 140

Glu Ser Leu Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
```

```
                195                 200                 205
Tyr Met Glu Leu Ser Ser Leu Arg Ser Glu Asp Thr Ala Val Tyr Tyr
        210                 215                 220

Cys Ala Arg Gly Ser Ala Tyr Tyr Tyr Asp Phe Ala Asp Tyr Trp Gly
225                 230                 235                 240

Gln Gly Thr Leu Val Thr Val Ser Ser Ala Ala Ala Gly Ser Asp Tyr
                245                 250                 255

Lys Asp Asp Asp Asp Lys
                260

<210> SEQ ID NO 7
<211> LENGTH: 754
<212> TYPE: PRT
<213> ORGANISM: artificial sequence
<220> FEATURE:
<223> OTHER INFORMATION: Fv polypeptide

<400> SEQUENCE: 7

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Gln Arg Pro Gly His Asp Leu Glu Trp Ile
            35                  40                  45

Gly Tyr Ile Asn Pro Ser Ser Gly Tyr Ser Asp Tyr Asn Gln Asn Phe
        50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Ser Tyr Val Leu Thr Gln Pro Ser Ser Val Ser Val Ala Pro Gly
            260                 265                 270

Gln Thr Ala Thr Ile Ser Cys Gly Gly His Asn Ile Gly Ser Lys Asn
        275                 280                 285

Val His Trp Tyr Gln Gln Arg Pro Gly Gln Ser Pro Val Leu Val Ile
```

```
                290                 295                 300
Tyr Gln Asp Asn Lys Arg Pro Ser Gly Ile Pro Glu Arg Phe Ser Gly
305                 310                 315                 320

Ser Asn Ser Gly Asn Thr Ala Thr Leu Thr Ile Ser Gly Thr Gln Ala
                325                 330                 335

Met Asp Glu Ala Asp Tyr Tyr Cys Gln Val Trp Asp Asn Tyr Ser Val
                340                 345                 350

Leu Phe Gly Gly Gly Thr Lys Leu Thr Val Leu Gly Gly Ser Gly Gly
                355                 360                 365

Ser Gly Gly Ser Ser Tyr Val Leu Thr Gln Pro Ser Ser Val Ser Val
370                 375                 380

Ala Pro Gly Gln Thr Ala Thr Ile Ser Cys Gly Gly His Asn Ile Gly
385                 390                 395                 400

Ser Lys Asn Val His Trp Tyr Gln Gln Arg Pro Gly Gln Ser Pro Val
                405                 410                 415

Leu Val Ile Tyr Gln Asp Asn Lys Arg Pro Ser Gly Ile Pro Glu Arg
                420                 425                 430

Phe Ser Gly Ser Asn Ser Gly Asn Thr Ala Thr Leu Thr Ile Ser Gly
                435                 440                 445

Thr Gln Ala Met Asp Glu Ala Asp Tyr Tyr Cys Gln Val Trp Asp Asn
                450                 455                 460

Tyr Ser Val Leu Phe Gly Gly Gly Thr Lys Leu Thr Val Leu Gly Gly
465                 470                 475                 480

Ser Gly Gly Ser Gly Gly Ser Ser Tyr Val Leu Thr Gln Pro Pro Ser
                485                 490                 495

Val Ser Val Ala Pro Gly Gln Thr Ala Arg Ile Thr Cys Gly Gly Asn
                500                 505                 510

Asn Ile Gly Ser Lys Thr Val His Trp Tyr Gln Gln Lys Pro Gly Gln
                515                 520                 525

Ala Pro Val Leu Val Val Tyr Asp Asp Ser Asp Arg Pro Ser Gly Ile
                530                 535                 540

Pro Glu Arg Phe Ser Gly Ser Asn Ser Gly Asn Thr Ala Thr Leu Thr
545                 550                 555                 560

Ile Ser Arg Val Glu Ala Gly Asp Glu Ala Asp Tyr Tyr Cys Gln Val
                565                 570                 575

Gly Thr Asp Trp Ser Asp His Leu Gln Val Phe Gly Gly Gly Thr Lys
                580                 585                 590

Leu Thr Val Leu Gly Gly Ser Gly Gly Ser Gly Gly Ser Gly Gly Ser
                595                 600                 605

Gly Gly Ser Gly Gly Ser Gly Gly Ser Glu Val Gln Leu Val Gln Ser
                610                 615                 620

Gly Ala Glu Val Lys Lys Pro Gly Glu Ser Leu Lys Ile Ser Cys Lys
625                 630                 635                 640

Gly Ser Gly Tyr Ser Phe Thr Ser Asn Trp Ile Gly Trp Val Arg Gln
                645                 650                 655

Met Pro Gly Lys Gly Leu Glu Trp Met Gly Met Ile Trp Pro Gly Asp
                660                 665                 670

Ser Asp Thr Met Tyr Ser Pro Ser Phe Gln Gly Gln Val Thr Ile Ser
                675                 680                 685

Ala Asp Glu Ser Ile Asn Thr Ala Tyr Leu Gln Trp Ser Ser Leu Lys
                690                 695                 700

Ala Ser Asp Thr Ala Met Tyr Tyr Cys Ala Arg Arg Glu Thr Thr Thr
705                 710                 715                 720
```

```
Val Gly Arg Tyr Tyr Tyr Ala Met Asp Tyr Trp Gln Gly Thr Leu
                725                 730                 735

Val Thr Val Ser Ser Ala Ala Ala Gly Ser Asp Tyr Lys Asp Asp
            740                 745                 750

Asp Lys

<210> SEQ ID NO 8
<211> LENGTH: 260
<212> TYPE: PRT
<213> ORGANISM: artificial sequence
<220> FEATURE:
<223> OTHER INFORMATION: Fv polypeptide

<400> SEQUENCE: 8

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser Gly Gly Ser Gly Gly Ser Gly Gly
        115                 120                 125

Ser Gln Val Gln Leu Val Gln Ser Gly Ala Glu Val Lys Lys Pro Gly
    130                 135                 140

Glu Ser Leu Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Gly Ser Ala Tyr Tyr Tyr Asp Phe Ala Asp Tyr Trp Gly
225                 230                 235                 240

Gln Gly Thr Leu Val Thr Val Ser Ser Ala Ala Ala Gly Ser His His
                245                 250                 255

His His His His
        260

<210> SEQ ID NO 9
<211> LENGTH: 494
<212> TYPE: PRT
<213> ORGANISM: artificial sequence
<220> FEATURE:
<223> OTHER INFORMATION: Fv polypeptide

<400> SEQUENCE: 9
```

```
Asp Ile Val Met Thr Gln Ser Pro Lys Phe Met Ser Thr Ser Val Gly
 1               5                  10                  15

Asp Arg Val Thr Val Thr Cys Lys Ala Ser Gln Asn Val Gly Thr Asn
             20                  25                  30

Val Ala Trp Phe Gln Gln Lys Pro Gly Gln Ser Pro Lys Val Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr His Thr Tyr Pro Leu
                 85                  90                  95

Thr Phe Gly Gly Gly Thr Lys Leu Glu Ile Asn Gly Gly Ser Gly Gly
             100                 105                 110

Ser Gly Gly Ser Gln Val Gln Leu Val Gln Ser Gly Ala Glu Val Lys
             115                 120                 125

Lys Pro Gly Glu Ser Leu Lys Val Ser Cys Lys Ala Ser Gly Tyr Thr
130                 135                 140

Phe Thr Ser Tyr Tyr Met His Trp Val Arg Gln Ala Pro Gly Gln Gly
145                 150                 155                 160

Leu Glu Trp Met Gly Ile Ile Asn Pro Ser Gly Gly Ser Thr Ser Tyr
                 165                 170                 175

Ala Gln Lys Phe Gln Gly Arg Val Thr Met Thr Arg Asp Thr Ser Thr
             180                 185                 190

Ser Thr Val Tyr Met Glu Leu Ser Ser Leu Arg Ser Glu Asp Thr Ala
             195                 200                 205

Val Tyr Tyr Cys Ala Arg Gly Ser Ala Tyr Tyr Asp Phe Ala Asp
210                 215                 220

Tyr Trp Gly Gln Gly Thr Leu Val Thr Val Ser Ser Gly Gly Ser Gly
225                 230                 235                 240

Gly Ser Gly Gly Ser Gln Val Gln Leu Val Gln Ser Gly Ala Glu Val
             245                 250                 255

Lys Lys Pro Gly Glu Ser Leu Lys Val Ser Cys Lys Ala Ser Gly Tyr
             260                 265                 270

Thr Phe Thr Ser Tyr Tyr Met His Trp Val Arg Gln Ala Pro Gly Gln
             275                 280                 285

Gly Leu Glu Trp Met Gly Ile Ile Asn Pro Ser Gly Gly Ser Thr Ser
290                 295                 300

Tyr Ala Gln Lys Phe Gln Gly Arg Val Thr Met Thr Arg Asp Thr Ser
305                 310                 315                 320

Thr Ser Thr Val Tyr Met Glu Leu Ser Ser Leu Arg Ser Glu Asp Thr
                 325                 330                 335

Ala Val Tyr Tyr Cys Ala Arg Gly Ser Ala Tyr Tyr Asp Phe Ala
             340                 345                 350

Asp Tyr Trp Gly Gln Gly Thr Leu Val Thr Val Ser Ser Gly Gly Ser
             355                 360                 365

Gly Gly Ser Gly Gly Ser Ser Tyr Val Leu Thr Gln Pro Pro Ser Val
             370                 375                 380

Ser Val Ala Pro Gly Gln Thr Ala Arg Ile Thr Cys Gly Gly Asn Asn
385                 390                 395                 400

Ile Gly Ser Lys Thr Val His Trp Tyr Gln Gln Lys Pro Gly Gln Ala
                 405                 410                 415
```

```
Pro Val Leu Val Val Tyr Asp Asp Ser Asp Arg Pro Ser Gly Ile Pro
            420                 425                 430

Glu Arg Phe Ser Gly Ser Asn Ser Gly Asn Thr Ala Thr Leu Thr Ile
        435                 440                 445

Ser Arg Val Glu Ala Gly Asp Glu Ala Asp Tyr Tyr Cys Gln Val Gly
    450                 455                 460

Thr Asp Trp Ser Asp His Leu Gln Val Phe Gly Gly Thr Lys Leu
465                 470                 475                 480

Thr Val Leu Ala Ala Ala Gly Ser His His His His His His
                485                 490
```

<210> SEQ ID NO 10
<211> LENGTH: 499
<212> TYPE: PRT
<213> ORGANISM: artificial sequence
<220> FEATURE:
<223> OTHER INFORMATION: Fv polypeptide

<400> SEQUENCE: 10

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Met Ile Trp Pro Gly Asp Ser Asp Thr Met Tyr Ser Pro Ser Phe
    50                  55                  60

Gln Gly Gln Val Thr Ile Ser Ala Asp Glu Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Leu Val Thr Val Ser Ser Gly Gly Ser Gly
        115                 120                 125

Gly Ser Gly Gly Ser Ser Tyr Val Leu Thr Gln Pro Ser Ser Val Ser
    130                 135                 140

Val Ala Pro Gly Gln Thr Ala Thr Ile Ser Cys Gly Gly His Asn Ile
145                 150                 155                 160

Gly Ser Lys Asn Val His Trp Tyr Gln Gln Arg Pro Gly Gln Ser Pro
                165                 170                 175

Val Leu Val Ile Tyr Gln Asp Asn Lys Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Thr Gln Ala Met Asp Glu Ala Asp Tyr Tyr Cys Gln Val Trp Asp
    210                 215                 220

Asn Tyr Ser Val Leu Phe Gly Gly Gly Thr Lys Leu Thr Val Leu Gly
225                 230                 235                 240

Gly Ser Gly Gly Ser Gly Gly Ser Ser Tyr Val Leu Thr Gln Pro Ser
                245                 250                 255

Ser Val Ser Val Ala Pro Gly Gln Thr Ala Thr Ile Ser Cys Gly Gly
            260                 265                 270

His Asn Ile Gly Ser Lys Asn Val His Trp Tyr Gln Gln Arg Pro Gly
        275                 280                 285
```

-continued

```
Gln Ser Pro Val Leu Val Ile Tyr Gln Asp Asn Lys Arg Pro Ser Gly
        290                 295                 300

Ile Pro Glu Arg Phe Ser Gly Ser Asn Ser Gly Asn Thr Ala Thr Leu
305                 310                 315                 320

Thr Ile Ser Gly Thr Gln Ala Met Asp Glu Ala Asp Tyr Tyr Cys Gln
                325                 330                 335

Val Trp Asp Asn Tyr Ser Val Leu Phe Gly Gly Gly Thr Lys Leu Thr
                340                 345                 350

Val Leu Gly Gly Ser Gly Gly Ser Gly Gly Ser Gln Val Gln Leu Gln
                355                 360                 365

Gln Ser Gly Ala Glu Leu Ala Arg Pro Gly Ala Ser Val Lys Met Ser
370                 375                 380

Cys Lys Ala Ser Gly Tyr Thr Phe Thr Thr Tyr Thr Ile His Trp Val
385                 390                 395                 400

Arg Gln Arg Pro Gly His Asp Leu Glu Trp Ile Gly Tyr Ile Asn Pro
                405                 410                 415

Ser Ser Gly Tyr Ser Asp Tyr Asn Gln Asn Phe Lys Gly Lys Thr Thr
                420                 425                 430

Leu Thr Ala Asp Lys Ser Ser Asn Thr Ala Tyr Met Gln Leu Asn Ser
                435                 440                 445

Leu Thr Ser Glu Asp Ser Ala Val Tyr Tyr Cys Ala Arg Arg Ala Asp
450                 455                 460

Tyr Gly Asn Tyr Glu Tyr Thr Trp Phe Ala Tyr Trp Gly Gln Gly Thr
465                 470                 475                 480

Thr Val Thr Val Ser Ser Ala Ala Ala Gly Ser Asp Tyr Lys Asp Asp
                485                 490                 495

Asp Asp Lys

<210> SEQ ID NO 11
<211> LENGTH: 1019
<212> TYPE: PRT
<213> ORGANISM: artificial sequence
<220> FEATURE:
<223> OTHER INFORMATION: Fv polypeptide

<400> SEQUENCE: 11

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Gln Arg Pro Gly His Asp Leu Glu Trp Ile
            35                  40                  45

Gly Tyr Ile Asn Pro Ser Ser Gly Tyr Ser Asp Tyr Asn Gln Asn Phe
        50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
        130                 135                 140

Met Thr Gln Ser Pro Lys Phe Met Ser Thr Ser Val Gly Asp Arg Val
```

```
            145                 150                 155                 160
        Thr Val Thr Cys Lys Ala Ser Gln Asn Val Gly Thr Asn Val Ala Trp
                        165                 170                 175
        Phe Gln Gln Lys Pro Gly Gln Ser Pro Lys Val Leu Ile Tyr Ser Ala
                        180                 185                 190

Ser Tyr Arg Tyr Ser Gly Val Pro Asp Arg Phe Thr Gly Ser Gly Ser
                        195                 200                 205

Gly Thr Asp Phe Thr Leu Thr Ile Ser Asn Val Gln Ser Glu Asp Leu
                    210                 215                 220

Ala Glu Tyr Phe Cys Gln Gln Tyr His Thr Tyr Pro Leu Thr Phe Gly
        225                 230                 235                 240

Gly Gly Thr Lys Leu Glu Ile Asn Gly Gly Ser Gly Gly Ser Gly Gly
                        245                 250                 255

Ser Gln Val Gln Leu Val Gln Ser Gly Ala Glu Val Lys Lys Pro Gly
                    260                 265                 270

Glu Ser Leu Lys Val Ser Cys Lys Ala Ser Gly Tyr Thr Phe Thr Ser
                    275                 280                 285

Tyr Tyr Met His Trp Val Arg Gln Ala Pro Gly Gln Gly Leu Glu Trp
                290                 295                 300

Met Gly Ile Ile Asn Pro Ser Gly Gly Ser Thr Ser Tyr Ala Gln Lys
        305                 310                 315                 320

Phe Gln Gly Arg Val Thr Met Thr Arg Asp Thr Ser Thr Ser Thr Val
                        325                 330                 335

Tyr Met Glu Leu Ser Ser Leu Arg Ser Glu Asp Thr Ala Val Tyr Tyr
                    340                 345                 350

Cys Ala Arg Gly Ser Ala Tyr Tyr Asp Phe Ala Asp Tyr Trp Gly
                    355                 360                 365

Gln Gly Thr Leu Val Thr Val Ser Ser Gly Gly Ser Gly Gly Ser Gly
            370                 375                 380

Gly Ser Gln Val Gln Leu Val Gln Ser Gly Ala Glu Val Lys Lys Pro
        385                 390                 395                 400

Gly Glu Ser Leu Lys Val Ser Cys Lys Ala Ser Gly Tyr Thr Phe Thr
                        405                 410                 415

Ser Tyr Tyr Met His Trp Val Arg Gln Ala Pro Gly Gln Gly Leu Glu
                        420                 425                 430

Trp Met Gly Ile Ile Asn Pro Ser Gly Gly Ser Thr Ser Tyr Ala Gln
                    435                 440                 445

Lys Phe Gln Gly Arg Val Thr Met Thr Arg Asp Thr Ser Thr Ser Thr
                    450                 455                 460

Val Tyr Met Glu Leu Ser Ser Leu Arg Ser Glu Asp Thr Ala Val Tyr
        465                 470                 475                 480

Tyr Cys Ala Arg Gly Ser Ala Tyr Tyr Asp Phe Ala Asp Tyr Trp
                        485                 490                 495

Gly Gln Gly Thr Leu Val Thr Val Ser Ser Gly Gly Ser Gly Gly Ser
                    500                 505                 510

Gly Gly Ser Gly Gly Ser Gly Gly Ser Ser Tyr Val Leu
                    515                 520                 525

Thr Gln Pro Ser Ser Val Ser Val Ala Pro Gly Gln Thr Ala Thr Ile
                    530                 535                 540

Ser Cys Gly Gly His Asn Ile Gly Ser Lys Asn Val His Trp Tyr Gln
        545                 550                 555                 560

Gln Arg Pro Gly Gln Ser Pro Val Leu Val Ile Tyr Gln Asp Asn Lys
                        565                 570                 575
```

```
Arg Pro Ser Gly Ile Pro Glu Arg Phe Ser Gly Ser Asn Ser Gly Asn
            580                 585                 590

Thr Ala Thr Leu Thr Ile Ser Gly Thr Gln Ala Met Asp Glu Ala Asp
            595                 600             605

Tyr Tyr Cys Gln Val Trp Asp Asn Tyr Ser Val Leu Phe Gly Gly Gly
610                 615                 620

Thr Lys Leu Thr Val Leu Gly Gly Ser Gly Gly Ser Gly Gly Ser Ser
625                 630                 635                 640

Tyr Val Leu Thr Gln Pro Ser Ser Val Ser Val Ala Pro Gly Gln Thr
                645                 650                 655

Ala Thr Ile Ser Cys Gly Gly His Asn Ile Gly Ser Lys Asn Val His
            660                 665                 670

Trp Tyr Gln Gln Arg Pro Gly Gln Ser Pro Val Leu Val Ile Tyr Gln
            675                 680                 685

Asp Asn Lys Arg Pro Ser Gly Ile Pro Glu Arg Phe Ser Gly Ser Asn
            690                 695                 700

Ser Gly Asn Thr Ala Thr Leu Thr Ile Ser Gly Thr Gln Ala Met Asp
705                 710                 715                 720

Glu Ala Asp Tyr Tyr Cys Gln Val Trp Asp Asn Tyr Ser Val Leu Phe
                725                 730                 735

Gly Gly Gly Thr Lys Leu Thr Val Leu Gly Gly Ser Gly Gly Ser Gly
            740                 745                 750

Gly Ser Ser Tyr Val Leu Thr Gln Pro Pro Ser Val Ser Val Ala Pro
        755                 760                 765

Gly Gln Thr Ala Arg Ile Thr Cys Gly Gly Asn Asn Ile Gly Ser Lys
    770                 775                 780

Thr Val His Trp Tyr Gln Gln Lys Pro Gly Gln Ala Pro Val Leu Val
785                 790                 795                 800

Val Tyr Asp Asp Ser Asp Arg Pro Ser Gly Ile Pro Glu Arg Phe Ser
                805                 810                 815

Gly Ser Asn Ser Gly Asn Thr Ala Thr Leu Thr Ile Ser Arg Val Glu
            820                 825                 830

Ala Gly Asp Glu Ala Asp Tyr Tyr Cys Gln Val Gly Thr Asp Trp Ser
        835                 840                 845

Asp His Leu Gln Val Phe Gly Gly Gly Thr Lys Leu Thr Val Leu Gly
    850                 855                 860

Gly Ser Gly Gly Ser Gly Gly Ser Gly Gly Ser Gly Gly Ser Gly Gly
865                 870                 875                 880

Ser Gly Gly Ser Glu Val Gln Leu Val Gln Ser Gly Ala Glu Val Lys
                885                 890                 895

Lys Pro Gly Glu Ser Leu Lys Ile Ser Cys Lys Gly Ser Gly Tyr Ser
            900                 905                 910

Phe Thr Ser Asn Trp Ile Gly Trp Val Arg Gln Met Pro Gly Lys Gly
            915                 920                 925

Leu Glu Trp Met Gly Met Ile Trp Pro Gly Asp Ser Asp Thr Met Tyr
            930                 935                 940

Ser Pro Ser Phe Gln Gly Gln Val Thr Ile Ser Ala Asp Glu Ser Ile
945                 950                 955                 960

Asn Thr Ala Tyr Leu Gln Trp Ser Ser Leu Lys Ala Ser Asp Thr Ala
                965                 970                 975

Met Tyr Tyr Cys Ala Arg Arg Glu Thr Thr Thr Val Gly Arg Tyr Tyr
            980                 985                 990
```

```
Tyr Ala Met Asp Tyr Trp Gly Gln Gly Thr Leu Val Thr Val Ser Ser
            995                1000                1005

Ala Ala Ala Gly Ser His His  His His His His
    1010             1015
```

<210> SEQ ID NO 12
<211> LENGTH: 749
<212> TYPE: PRT
<213> ORGANISM: artificial
<220> FEATURE:
<223> OTHER INFORMATION: Fv polypeptide

<400> SEQUENCE: 12

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Ser Gly Gly Gly
        115                 120                 125

Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Ser Tyr Val Leu Thr Gln Pro Ser Ser Val Ser Val Ala Pro Gly
            260                 265                 270

Gln Thr Ala Thr Ile Ser Cys Gly Gly His Asn Ile Gly Ser Lys Asn
        275                 280                 285

Val His Trp Tyr Gln Gln Arg Pro Gly Gln Ser Pro Val Leu Val Ile
    290                 295                 300

Tyr Gln Asp Asn Lys Arg Pro Ser Gly Ile Pro Glu Arg Phe Ser Gly
305                 310                 315                 320

Ser Asn Ser Gly Asn Thr Ala Thr Leu Thr Ile Ser Gly Thr Gln Ala
                325                 330                 335
```

```
Met Asp Glu Ala Asp Tyr Tyr Cys Gln Val Trp Asp Asn Tyr Ser Val
            340                 345                 350
Leu Phe Gly Gly Gly Thr Lys Leu Thr Val Leu Gly Gly Ser Gly Gly
        355                 360                 365
Ser Gly Gly Ser Ser Tyr Val Leu Thr Gln Pro Ser Ser Val Ser Val
    370                 375                 380
Ala Pro Gly Gln Thr Ala Thr Ile Ser Cys Gly Gly His Asn Ile Gly
385                 390                 395                 400
Ser Lys Asn Val His Trp Tyr Gln Gln Arg Pro Gly Gln Ser Pro Val
                405                 410                 415
Leu Val Ile Tyr Gln Asp Asn Lys Arg Pro Ser Gly Ile Pro Glu Arg
            420                 425                 430
Phe Ser Gly Ser Asn Ser Gly Asn Thr Ala Thr Leu Thr Ile Ser Gly
        435                 440                 445
Thr Gln Ala Met Asp Glu Ala Asp Tyr Tyr Cys Gln Val Trp Asp Asn
    450                 455                 460
Tyr Ser Val Leu Phe Gly Gly Gly Thr Lys Leu Thr Val Leu Gly Gly
465                 470                 475                 480
Ser Gly Gly Ser Gly Gly Ser Glu Val Gln Leu Val Gln Ser Gly Ala
                485                 490                 495
Glu Val Lys Lys Pro Gly Glu Ser Leu Lys Ile Ser Cys Lys Gly Ser
            500                 505                 510
Gly Tyr Ser Phe Thr Ser Asn Trp Ile Gly Trp Val Arg Gln Met Pro
        515                 520                 525
Gly Lys Gly Leu Glu Trp Met Gly Met Ile Trp Pro Gly Asp Ser Asp
    530                 535                 540
Thr Met Tyr Ser Pro Ser Phe Gln Gly Gln Val Thr Ile Ser Ala Asp
545                 550                 555                 560
Glu Ser Ile Asn Thr Ala Tyr Leu Gln Trp Ser Ser Leu Lys Ala Ser
                565                 570                 575
Asp Thr Ala Met Tyr Tyr Cys Ala Arg Arg Glu Thr Thr Thr Val Gly
            580                 585                 590
Arg Tyr Tyr Tyr Ala Met Asp Tyr Trp Gly Gln Gly Thr Leu Val Thr
        595                 600                 605
Val Ser Ser Gly Gly Ser Gly Gly Ser Gly Gly Ser Gly Gly Ser Gly
    610                 615                 620
Gly Ser Gly Gly Ser Ser Tyr Val Leu Thr Gln Pro Pro Ser Val Ser
625                 630                 635                 640
Val Ala Pro Gly Gln Thr Ala Arg Ile Thr Cys Gly Gly Asn Asn Ile
                645                 650                 655
Gly Ser Lys Thr Val His Trp Tyr Gln Gln Lys Pro Gly Gln Ala Pro
            660                 665                 670
Val Leu Val Val Tyr Asp Asp Ser Asp Arg Pro Ser Gly Ile Pro Glu
        675                 680                 685
Arg Phe Ser Gly Ser Asn Ser Gly Asn Thr Ala Thr Leu Thr Ile Ser
    690                 695                 700
Arg Val Glu Ala Gly Asp Glu Ala Asp Tyr Tyr Cys Gln Val Gly Thr
705                 710                 715                 720
Asp Trp Ser Asp His Leu Gln Val Phe Gly Gly Gly Thr Lys Leu Thr
                725                 730                 735
Val Leu Ala Ala Ala Gly Ser His His His His His
            740                 745
```

```
<210> SEQ ID NO 13
<211> LENGTH: 262
<212> TYPE: PRT
<213> ORGANISM: artificial
<220> FEATURE:
<223> OTHER INFORMATION: Fv polypeptide

<400> SEQUENCE: 13

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser Gly Gly Ser Gly Gly Ser Gly Gly
        115                 120                 125

Ser Gln Val Gln Leu Val Gln Ser Gly Ala Glu Val Lys Lys Pro Gly
    130                 135                 140

Glu Ser Leu Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Gly Ser Ala Tyr Tyr Tyr Asp Phe Ala Asp Tyr Trp Gly
225                 230                 235                 240

Gln Gly Thr Leu Val Thr Val Ser Ser Ala Ala Gly Ser Asp Tyr
                245                 250                 255

Lys Asp Asp Asp Asp Lys
            260

<210> SEQ ID NO 14
<211> LENGTH: 749
<212> TYPE: PRT
<213> ORGANISM: artificial
<220> FEATURE:
<223> OTHER INFORMATION: Fv polypeptide

<400> SEQUENCE: 14

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Gln Arg Pro Gly His Asp Leu Glu Trp Ile
            35                  40                  45
```

```
Gly Tyr Ile Asn Pro Ser Ser Gly Tyr Ser Asp Tyr Asn Gln Asn Phe
        50              55                  60

Lys Gly Lys Thr Thr Leu Thr Ala Asp Lys Ser Ser Asn Thr Ala Tyr
65              70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Ser Gly Gly
            115                 120                 125

Ser Gly Gly Ser Gly Gly Ser Gly Gly Ser Gly Gly Ser Asp Ile Val
130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
            195                 200                 205

Gly Thr Asp Phe Thr Leu Thr Ile Ser Asn Val Gln Ser Glu Asp Leu
210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
            245                 250                 255

Ser Ser Tyr Val Leu Thr Gln Pro Ser Ser Val Ser Val Ala Pro Gly
            260                 265                 270

Gln Thr Ala Thr Ile Ser Cys Gly Gly His Asn Ile Gly Ser Lys Asn
            275                 280                 285

Val His Trp Tyr Gln Gln Arg Pro Gly Gln Ser Pro Val Leu Val Ile
            290                 295                 300

Tyr Gln Asp Asn Lys Arg Pro Ser Gly Ile Pro Glu Arg Phe Ser Gly
305                 310                 315                 320

Ser Asn Ser Gly Asn Thr Ala Thr Leu Thr Ile Ser Gly Thr Gln Ala
            325                 330                 335

Met Asp Glu Ala Asp Tyr Tyr Cys Gln Val Trp Asp Asn Tyr Ser Val
            340                 345                 350

Leu Phe Gly Gly Gly Thr Lys Leu Thr Val Leu Gly Gly Ser Gly Gly
            355                 360                 365

Ser Gly Gly Ser Ser Tyr Val Leu Thr Gln Pro Ser Ser Val Ser Val
            370                 375                 380

Ala Pro Gly Gln Thr Ala Thr Ile Ser Cys Gly Gly His Asn Ile Gly
385                 390                 395                 400

Ser Lys Asn Val His Trp Tyr Gln Gln Arg Pro Gly Gln Ser Pro Val
            405                 410                 415

Leu Val Ile Tyr Gln Asp Asn Lys Arg Pro Ser Gly Ile Pro Glu Arg
            420                 425                 430

Phe Ser Gly Ser Asn Ser Gly Asn Thr Ala Thr Leu Thr Ile Ser Gly
            435                 440                 445

Thr Gln Ala Met Asp Glu Ala Asp Tyr Tyr Cys Gln Val Trp Asp Asn
450                 455                 460

Tyr Ser Val Leu Phe Gly Gly Gly Thr Lys Leu Thr Val Leu Gly Gly
```

```
            465                 470                 475                 480
    Ser Gly Gly Ser Gly Gly Ser Glu Val Gln Leu Val Gln Ser Gly Ala
                    485                 490                 495
    Glu Val Lys Lys Pro Gly Glu Ser Leu Lys Ile Ser Cys Lys Gly Ser
                    500                 505                 510
    Gly Tyr Ser Phe Thr Ser Asn Trp Ile Gly Trp Val Arg Gln Met Pro
                    515                 520                 525
    Gly Lys Gly Leu Glu Trp Met Gly Met Ile Trp Pro Gly Asp Ser Asp
                    530                 535                 540
    Thr Met Tyr Ser Pro Ser Phe Gln Gly Gln Val Thr Ile Ser Ala Asp
    545                 550                 555                 560
    Glu Ser Ile Asn Thr Ala Tyr Leu Gln Trp Ser Ser Leu Lys Ala Ser
                    565                 570                 575
    Asp Thr Ala Met Tyr Tyr Cys Ala Arg Arg Glu Thr Thr Thr Val Gly
                    580                 585                 590
    Arg Tyr Tyr Tyr Ala Met Asp Tyr Trp Gly Gln Gly Thr Leu Val Thr
                    595                 600                 605
    Val Ser Ser Gly Gly Ser Gly Gly Ser Gly Gly Ser Gly Gly Ser Gly
                    610                 615                 620
    Gly Ser Gly Gly Ser Ser Tyr Val Leu Thr Gln Pro Pro Ser Val Ser
    625                 630                 635                 640
    Val Ala Pro Gly Gln Thr Ala Arg Ile Thr Cys Gly Gly Asn Asn Ile
                    645                 650                 655
    Gly Ser Lys Thr Val His Trp Tyr Gln Gln Lys Pro Gly Gln Ala Pro
                    660                 665                 670
    Val Leu Val Val Tyr Asp Asp Ser Asp Arg Pro Ser Gly Ile Pro Glu
                    675                 680                 685
    Arg Phe Ser Gly Ser Asn Ser Gly Asn Thr Ala Thr Leu Thr Ile Ser
                    690                 695                 700
    Arg Val Glu Ala Gly Asp Glu Ala Asp Tyr Tyr Cys Gln Val Gly Thr
    705                 710                 715                 720
    Asp Trp Ser Asp His Leu Gln Val Phe Gly Gly Gly Thr Lys Leu Thr
                    725                 730                 735
    Val Leu Ala Ala Ala Gly Ser His His His His His
                    740                 745

<210> SEQ ID NO 15
<211> LENGTH: 522
<212> TYPE: PRT
<213> ORGANISM: artificial
<220> FEATURE:
<223> OTHER INFORMATION: Fv polypeptide

<400> SEQUENCE: 15

Gln Val Gln Leu Val Gln Ser Gly Ala Glu Val Lys Lys Pro Gly Glu
    1               5                   10                  15
    Ser Leu Lys Val Ser Cys Lys Ala Ser Gly Tyr Thr Phe Thr Ser Tyr
                    20                  25                  30
    Tyr Met His Trp Val Arg Gln Ala Pro Gly Gln Gly Leu Glu Trp Met
                35                  40                  45
    Gly Ile Ile Asn Pro Ser Gly Gly Ser Thr Ser Tyr Ala Gln Lys Phe
                50                  55                  60
    Gln Gly Arg Val Thr Met Thr Arg Asp Thr Ser Thr Ser Thr Val Tyr
    65                  70                  75                  80
    Met Glu Leu Ser Ser Leu Arg Ser Glu Asp Thr Ala Val Tyr Tyr Cys
```

```
                    85                  90                  95

Ala Arg Gly Ser Ala Tyr Tyr Asp Phe Ala Asp Tyr Trp Gly Gln
                100                 105                 110

Gly Thr Leu Val Thr Val Ser Ser Gly Gly Ser Gly Gly
                115                 120                 125

Ser Gln Val Gln Leu Val Gln Ser Gly Ala Glu Val Lys Lys Pro Gly
            130                 135                 140

Glu Ser Leu Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
                180                 185                 190

Phe Gln Gly Arg Val Thr Met Thr Arg Asp Thr Ser Thr Ser Thr Val
                195                 200                 205

Tyr Met Glu Leu Ser Ser Leu Arg Ser Glu Asp Thr Ala Val Tyr Tyr
            210                 215                 220

Cys Ala Arg Gly Ser Ala Tyr Tyr Asp Phe Ala Asp Tyr Trp Gly
225                 230                 235                 240

Gln Gly Thr Leu Val Thr Val Ser Ser Gly Gly Ser Gly Gly Ser Gly
                245                 250                 255

Gly Ser Ser Tyr Glu Leu Thr Gln Pro Pro Ser Val Ser Val Ser Pro
                260                 265                 270

Gly Gln Thr Ala Arg Ile Thr Cys Ser Gly Asp Ala Leu Pro Lys Gln
                275                 280                 285

Tyr Ala Tyr Trp Tyr Gln Gln Lys Pro Gly Gln Ala Pro Val Leu Val
            290                 295                 300

Ile Tyr Lys Asp Ser Glu Arg Pro Ser Gly Ile Pro Glu Arg Phe Ser
305                 310                 315                 320

Gly Ser Ser Ser Gly Thr Thr Val Thr Leu Thr Ile Ser Gly Val Gln
                325                 330                 335

Ala Glu Asp Glu Ala Asp Tyr Tyr Cys Gln Ser Ala Asp Ser Ser Gly
                340                 345                 350

Thr Pro Leu Ile Val Phe Gly Thr Gly Thr Lys Leu Thr Val Leu Gly
            355                 360                 365

Gly Ser Gly Gly Ser Gly Gly Ser Gly Gly Ser Gly Gly
                370                 375                 380

Ser Gly Gly Ser Glu Val Gln Leu Val Gln Ser Gly Ala Glu Val Lys
385                 390                 395                 400

Lys Pro Gly Glu Ser Leu Lys Ile Ser Cys Lys Gly Ser Gly Tyr Ser
                405                 410                 415

Phe Thr Ser Tyr Trp Ile Gly Trp Val Arg Gln Met Pro Gly Lys Gly
            420                 425                 430

Leu Glu Trp Met Gly Ile Ile Tyr Pro Gly Asp Ser Asp Thr Arg Tyr
            435                 440                 445

Ser Pro Ser Phe Gln Gly Gln Val Thr Ile Ser Ala Asp Lys Ser Ile
450                 455                 460

Ser Thr Ala Tyr Leu Gln Trp Ser Ser Leu Lys Ala Ser Asp Thr Ala
465                 470                 475                 480

Met Tyr Tyr Cys Ala Arg Leu Gly Ser Ser Trp Thr Asn Asp Ala Phe
                485                 490                 495

Asp Ile Trp Gly Gln Gly Thr Met Val Thr Val Ser Ser Ala Ala Ala
                500                 505                 510
```

```
Gly Ser Asp Tyr Lys Asp Asp Asp Lys
            515             520

<210> SEQ ID NO 16
<211> LENGTH: 1264
<212> TYPE: PRT
<213> ORGANISM: artificial
<220> FEATURE:
<223> OTHER INFORMATION: Fv polypeptide

<400> SEQUENCE: 16

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Gln Arg Pro Gly His Asp Leu Glu Trp Ile
            35                  40                  45

Gly Tyr Ile Asn Pro Ser Ser Gly Tyr Ser Asp Tyr Asn Gln Asn Phe
        50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Asp Ile Val Met Thr Gln Ser Pro Lys Phe Met Ser
    130                 135                 140

Thr Ser Val Gly Asp Arg Val Thr Val Thr Cys Lys Ala Ser Gln Asn
145                 150                 155                 160

Val Gly Thr Asn Val Ala Trp Phe Gln Gln Lys Pro Gly Gln Ser Pro
                165                 170                 175

Lys Val Leu Ile Tyr Ser Ala Ser Tyr Arg Tyr Ser Gly Val Pro Asp
            180                 185                 190

Arg Phe Thr Gly Ser Gly Ser Gly Thr Asp Phe Thr Leu Thr Ile Ser
        195                 200                 205

Asn Val Gln Ser Glu Asp Leu Ala Glu Tyr Phe Cys Gln Gln Tyr His
    210                 215                 220

Thr Tyr Pro Leu Thr Phe Gly Gly Gly Thr Lys Leu Glu Ile Asn Gly
225                 230                 235                 240

Gly Ser Gly Gly Ser Gly Gly Ser Gly Gly Ser Gly Gly Ser Gly Gly
                245                 250                 255

Ser Gly Gly Ser Gln Val Gln Leu Gln Gln Ser Gly Ala Glu Leu Ala
            260                 265                 270

Arg Pro Gly Ala Ser Val Lys Met Ser Cys Lys Ala Ser Gly Tyr Thr
        275                 280                 285

Phe Thr Thr Tyr Thr Ile His Trp Val Arg Gln Arg Pro Gly His Asp
    290                 295                 300

Leu Glu Trp Ile Gly Tyr Ile Asn Pro Ser Ser Gly Tyr Ser Asp Tyr
305                 310                 315                 320

Asn Gln Asn Phe Lys Gly Lys Thr Thr Leu Thr Ala Asp Lys Ser Ser
                325                 330                 335

Asn Thr Ala Tyr Met Gln Leu Asn Ser Leu Thr Ser Glu Asp Ser Ala
            340                 345                 350
```

-continued

```
Val Tyr Tyr Cys Ala Arg Arg Ala Asp Tyr Gly Asn Tyr Glu Tyr Thr
        355                 360                 365

Trp Phe Ala Tyr Trp Gly Gln Gly Thr Thr Val Thr Val Ser Ser Gly
370                 375                 380

Gly Ser Gly Gly Ser Gly Gly Ser Asp Ile Val Met Thr Gln Ser Pro
385                 390                 395                 400

Lys Phe Met Ser Thr Ser Val Gly Asp Arg Val Thr Val Thr Cys Lys
                405                 410                 415

Ala Ser Gln Asn Val Gly Thr Asn Val Ala Trp Phe Gln Gln Lys Pro
                420                 425                 430

Gly Gln Ser Pro Lys Val Leu Ile Tyr Ser Ala Ser Tyr Arg Tyr Ser
            435                 440                 445

Gly Val Pro Asp Arg Phe Thr Gly Ser Gly Ser Gly Thr Asp Phe Thr
        450                 455                 460

Leu Thr Ile Ser Asn Val Gln Ser Glu Asp Leu Ala Glu Tyr Phe Cys
465                 470                 475                 480

Gln Gln Tyr His Thr Tyr Pro Leu Thr Phe Gly Gly Gly Thr Lys Leu
                485                 490                 495

Glu Ile Asn Gly Gly Ser Gly Gly Ser Gly Gly Ser Ser Tyr Val Leu
            500                 505                 510

Thr Gln Pro Ser Ser Val Ser Val Ala Pro Gly Gln Thr Ala Thr Ile
        515                 520                 525

Ser Cys Gly Gly His Asn Ile Gly Ser Lys Asn Val His Trp Tyr Gln
530                 535                 540

Gln Arg Pro Gly Gln Ser Pro Val Leu Val Ile Tyr Gln Asp Asn Lys
545                 550                 555                 560

Arg Pro Ser Gly Ile Pro Glu Arg Phe Ser Gly Ser Asn Ser Gly Asn
                565                 570                 575

Thr Ala Thr Leu Thr Ile Ser Gly Thr Gln Ala Met Asp Glu Ala Asp
                580                 585                 590

Tyr Tyr Cys Gln Val Trp Asp Asn Tyr Ser Val Leu Phe Gly Gly Gly
            595                 600                 605

Thr Lys Leu Thr Val Leu Gly Gly Ser Gly Gly Ser Gly Gly Ser Ser
        610                 615                 620

Tyr Val Leu Thr Gln Pro Ser Ser Val Ser Val Ala Pro Gly Gln Thr
625                 630                 635                 640

Ala Thr Ile Ser Cys Gly Gly His Asn Ile Gly Ser Lys Asn Val His
                645                 650                 655

Trp Tyr Gln Gln Arg Pro Gly Gln Ser Pro Val Leu Val Ile Tyr Gln
            660                 665                 670

Asp Asn Lys Arg Pro Ser Gly Ile Pro Glu Arg Phe Ser Gly Ser Asn
        675                 680                 685

Ser Gly Asn Thr Ala Thr Leu Thr Ile Ser Gly Thr Gln Ala Met Asp
690                 695                 700

Glu Ala Asp Tyr Tyr Cys Gln Val Trp Asp Asn Tyr Ser Val Leu Phe
705                 710                 715                 720

Gly Gly Gly Thr Lys Leu Thr Val Leu Gly Gly Ser Gly Gly Ser Gly
                725                 730                 735

Gly Ser Glu Val Gln Leu Val Gln Ser Gly Ala Glu Val Lys Lys Pro
            740                 745                 750

Gly Glu Ser Leu Lys Ile Ser Cys Lys Gly Ser Gly Tyr Ser Phe Thr
        755                 760                 765
```

-continued

```
Ser Asn Trp Ile Gly Trp Val Arg Gln Met Pro Gly Lys Gly Leu Glu
770                 775                 780

Trp Met Gly Met Ile Trp Pro Gly Asp Ser Asp Thr Met Tyr Ser Pro
785                 790                 795                 800

Ser Phe Gln Gly Gln Val Thr Ile Ser Ala Asp Glu Ser Ile Asn Thr
                805                 810                 815

Ala Tyr Leu Gln Trp Ser Ser Leu Lys Ala Ser Asp Thr Ala Met Tyr
            820                 825                 830

Tyr Cys Ala Arg Arg Glu Thr Thr Val Gly Arg Tyr Tyr Tyr Ala
        835                 840                 845

Met Asp Tyr Trp Gly Gln Gly Thr Leu Val Thr Val Ser Ser Gly Gly
850                 855                 860

Ser Gly Gly Ser Gly Gly Ser Ser Tyr Val Leu Thr Gln Pro Pro Ser
865                 870                 875                 880

Val Ser Val Ala Pro Gly Gln Thr Ala Arg Ile Thr Cys Gly Gly Asn
                885                 890                 895

Asn Ile Gly Ser Lys Thr Val His Trp Tyr Gln Gln Lys Pro Gly Gln
            900                 905                 910

Ala Pro Val Leu Val Val Tyr Asp Asp Ser Asp Arg Pro Ser Gly Ile
        915                 920                 925

Pro Glu Arg Phe Ser Gly Ser Asn Ser Gly Asn Thr Ala Thr Leu Thr
930                 935                 940

Ile Ser Arg Val Glu Ala Gly Asp Glu Ala Asp Tyr Tyr Cys Gln Val
945                 950                 955                 960

Gly Thr Asp Trp Ser Asp His Leu Gln Val Phe Gly Gly Gly Thr Lys
                965                 970                 975

Leu Thr Val Leu Gly Gly Ser Gly Gly Ser Gly Gly Ser Gly Gly Ser
            980                 985                 990

Gly Gly Ser Gly Gly Ser Gly Gly Ser Glu Val Gln Leu Val Gln Ser
        995                 1000                1005

Gly Ala Glu Val Lys Lys Pro Gly Glu Ser Leu Lys Ile Ser Cys
1010                1015                1020

Lys Gly Ser Gly Tyr Ser Phe Thr Ser Asn Trp Ile Gly Trp Val
1025                1030                1035

Arg Gln Met Pro Gly Lys Gly Leu Glu Trp Met Gly Met Ile Trp
1040                1045                1050

Pro Gly Asp Ser Asp Thr Met Tyr Ser Pro Ser Phe Gln Gly Gln
1055                1060                1065

Val Thr Ile Ser Ala Asp Glu Ser Ile Asn Thr Ala Tyr Leu Gln
1070                1075                1080

Trp Ser Ser Leu Lys Ala Ser Asp Thr Ala Met Tyr Tyr Cys Ala
1085                1090                1095

Arg Arg Glu Thr Thr Thr Val Gly Arg Tyr Tyr Tyr Ala Met Asp
1100                1105                1110

Tyr Trp Gly Gln Gly Thr Leu Val Thr Val Ser Ser Gly Gly Ser
1115                1120                1125

Gly Gly Ser Gly Gly Ser Ser Tyr Val Leu Thr Gln Pro Pro Ser
1130                1135                1140

Val Ser Val Ala Pro Gly Gln Thr Ala Arg Ile Thr Cys Gly Gly
1145                1150                1155

Asn Asn Ile Gly Ser Lys Thr Val His Trp Tyr Gln Gln Lys Pro
1160                1165                1170

Gly Gln Ala Pro Val Leu Val Val Tyr Asp Asp Ser Asp Arg Pro
```

Ser Gly Ile Pro Glu Arg Phe Ser Gly Ser Asn Ser Gly Asn Thr
    1190                1195                1200

Ala Thr Leu Thr Ile Ser Arg Val Glu Ala Gly Asp Glu Ala Asp
    1205                1210                1215

Tyr Tyr Cys Gln Val Gly Thr Asp Trp Ser Asp His Leu Gln Val
    1220                1225                1230

Phe Gly Gly Gly Thr Lys Leu Thr Val Leu Ala Ala Ala Gly Ser
    1235                1240                1245

His His His His His His Ala Arg Thr Ile Phe Ile Cys Ile Ala
    1250                1255                1260

Leu

<210> SEQ ID NO 17
<211> LENGTH: 262
<212> TYPE: PRT
<213> ORGANISM: artificial
<220> FEATURE:
<223> OTHER INFORMATION: Fv polypeptide

<400> SEQUENCE: 17

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser Gly Gly Ser Gly Gly Ser Gly Gly
        115                 120                 125

Ser Gln Val Gln Leu Val Gln Ser Gly Ala Glu Val Lys Lys Pro Gly
    130                 135                 140

Glu Ser Leu Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Gly Ser Ala Tyr Tyr Tyr Asp Phe Ala Asp Tyr Trp Gly
225                 230                 235                 240

Gln Gly Thr Leu Val Thr Val Ser Ser Ala Ala Ala Gly Ser Asp Tyr
                245                 250                 255

Lys Asp Asp Asp Asp Lys
            260

<210> SEQ ID NO 18
<211> LENGTH: 749
<212> TYPE: PRT
<213> ORGANISM: artificial
<220> FEATURE:
<223> OTHER INFORMATION: Fv polypeptide

<400> SEQUENCE: 18

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Ser Tyr Val Leu Thr Gln Pro Ser Ser Val Ser Val Ala Pro Gly
            260                 265                 270

Gln Thr Ala Thr Ile Ser Cys Gly Gly His Asn Ile Gly Ser Lys Asn
        275                 280                 285

Val His Trp Tyr Gln Gln Arg Pro Gly Gln Ser Pro Val Leu Val Ile
    290                 295                 300

Tyr Gln Asp Asn Lys Arg Pro Ser Gly Ile Pro Glu Arg Phe Ser Gly
305                 310                 315                 320

Ser Asn Ser Gly Asn Thr Ala Thr Leu Thr Ile Ser Gly Thr Gln Ala
                325                 330                 335

Met Asp Glu Ala Asp Tyr Tyr Cys Gln Val Trp Asp Asn Tyr Ser Val
            340                 345                 350

Leu Phe Gly Gly Gly Thr Lys Leu Thr Val Leu Gly Gly Ser Gly Gly
        355                 360                 365
```

```
Ser Gly Gly Ser Ser Tyr Val Leu Thr Gln Pro Ser Val Ser Val
        370                 375                 380

Ala Pro Gly Gln Thr Ala Thr Ile Ser Cys Gly His Asn Ile Gly
385                 390                 395                 400

Ser Lys Asn Val His Trp Tyr Gln Gln Arg Pro Gly Gln Ser Pro Val
                405                 410                 415

Leu Val Ile Tyr Gln Asp Asn Lys Arg Pro Ser Gly Ile Pro Glu Arg
            420                 425                 430

Phe Ser Gly Ser Asn Ser Gly Asn Thr Ala Thr Leu Thr Ile Ser Gly
        435                 440                 445

Thr Gln Ala Met Asp Glu Ala Asp Tyr Tyr Cys Gln Val Trp Asp Asn
    450                 455                 460

Tyr Ser Val Leu Phe Gly Gly Thr Lys Leu Thr Val Leu Gly Gly
465                 470                 475                 480

Ser Gly Gly Ser Gly Gly Ser Glu Val Gln Leu Val Gln Ser Gly Ala
                485                 490                 495

Glu Val Lys Lys Pro Gly Glu Ser Leu Lys Ile Ser Cys Lys Gly Ser
            500                 505                 510

Gly Tyr Ser Phe Thr Ser Asn Trp Ile Gly Trp Val Arg Gln Met Pro
        515                 520                 525

Gly Lys Gly Leu Glu Trp Met Gly Met Ile Trp Pro Gly Asp Ser Asp
    530                 535                 540

Thr Met Tyr Ser Pro Ser Phe Gln Gly Gln Val Thr Ile Ser Ala Asp
545                 550                 555                 560

Glu Ser Ile Asn Thr Ala Tyr Leu Gln Trp Ser Ser Leu Lys Ala Ser
                565                 570                 575

Asp Thr Ala Met Tyr Tyr Cys Ala Arg Arg Glu Thr Thr Thr Val Gly
            580                 585                 590

Arg Tyr Tyr Tyr Ala Met Asp Tyr Trp Gly Gln Gly Thr Leu Val Thr
        595                 600                 605

Val Ser Ser Gly Gly Ser Gly Gly Ser Gly Gly Ser Gly
    610                 615                 620

Gly Ser Gly Gly Ser Ser Tyr Val Leu Thr Gln Pro Pro Ser Val Ser
625                 630                 635                 640

Val Ala Pro Gly Gln Thr Ala Arg Ile Thr Cys Gly Gly Asn Asn Ile
                645                 650                 655

Gly Ser Lys Thr Val His Trp Tyr Gln Gln Lys Pro Gly Gln Ala Pro
            660                 665                 670

Val Leu Val Val Tyr Asp Asp Ser Asp Arg Pro Ser Gly Ile Pro Glu
        675                 680                 685

Arg Phe Ser Gly Ser Asn Ser Gly Asn Thr Ala Thr Leu Thr Ile Ser
    690                 695                 700

Arg Val Glu Ala Gly Asp Glu Ala Asp Tyr Tyr Cys Gln Val Gly Thr
705                 710                 715                 720

Asp Trp Ser Asp His Leu Gln Val Phe Gly Gly Thr Lys Leu Thr
                725                 730                 735

Val Leu Ala Ala Ala Gly Ser His His His His His His
            740                 745

<210> SEQ ID NO 19
<211> LENGTH: 778
<212> TYPE: PRT
<213> ORGANISM: artificial
<220> FEATURE:
```

<223> OTHER INFORMATION: Fv polypeptide

<400> SEQUENCE: 19

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Gln Val Gln Leu Val Gln Ser Gly Ala Glu Val Lys Lys Pro Gly
            260                 265                 270

Glu Ser Leu Lys Val Ser Cys Lys Ala Ser Gly Tyr Thr Phe Thr Ser
        275                 280                 285

Tyr Tyr Met His Trp Val Arg Gln Ala Pro Gly Gln Gly Leu Glu Trp
    290                 295                 300

Met Gly Ile Ile Asn Pro Ser Gly Gly Ser Thr Ser Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Gly Ser Ala Tyr Tyr Tyr Asp Phe Ala Asp Tyr Trp Gly
        355                 360                 365

Gln Gly Thr Leu Val Thr Val Ser Ser Gly Gly Ser Gly Gly Ser Gly
    370                 375                 380

Gly Ser Gln Val Gln Leu Val Gln Ser Gly Ala Glu Val Lys Lys Pro
385                 390                 395                 400

Gly Glu Ser Leu Lys Val Ser Cys Lys Ala Ser Gly Tyr Thr Phe Thr
            405                 410                 415

Ser Tyr Tyr Met His Trp Val Arg Gln Ala Pro Gly Gln Gly Leu Glu
        420                 425                 430

Trp Met Gly Ile Ile Asn Pro Ser Gly Gly Ser Thr Ser Tyr Ala Gln
            435                 440                 445

Lys Phe Gln Gly Arg Val Thr Met Thr Arg Asp Thr Ser Thr Ser Thr
450                 455                 460

Val Tyr Met Glu Leu Ser Ser Leu Arg Ser Glu Asp Thr Ala Val Tyr
465                 470                 475                 480

Tyr Cys Ala Arg Gly Ser Ala Tyr Tyr Tyr Asp Phe Ala Asp Tyr Trp
                485                 490                 495

Gly Gln Gly Thr Leu Val Thr Val Ser Ser Gly Gly Ser Gly Gly Ser
            500                 505                 510

Gly Gly Ser Ser Tyr Glu Leu Thr Gln Pro Pro Ser Val Ser Val Ser
        515                 520                 525

Pro Gly Gln Thr Ala Arg Ile Thr Cys Ser Gly Asp Ala Leu Pro Lys
    530                 535                 540

Gln Tyr Ala Tyr Trp Tyr Gln Gln Lys Pro Gly Gln Ala Pro Val Leu
545                 550                 555                 560

Val Ile Tyr Lys Asp Ser Glu Arg Pro Ser Gly Ile Pro Glu Arg Phe
                565                 570                 575

Ser Gly Ser Ser Ser Gly Thr Thr Val Thr Leu Thr Ile Ser Gly Val
            580                 585                 590

Gln Ala Glu Asp Glu Ala Asp Tyr Tyr Cys Gln Ser Ala Asp Ser Ser
        595                 600                 605

Gly Thr Pro Leu Ile Val Phe Gly Thr Gly Thr Lys Leu Thr Val Leu
    610                 615                 620

Gly Gly Ser Gly Gly Ser Gly Gly Ser Gly Gly Ser Gly Gly Ser Gly
625                 630                 635                 640

Gly Ser Gly Gly Ser Glu Val Gln Leu Val Gln Ser Gly Ala Glu Val
                645                 650                 655

Lys Lys Pro Gly Glu Ser Leu Lys Ile Ser Cys Lys Gly Ser Gly Tyr
            660                 665                 670

Ser Phe Thr Ser Tyr Trp Ile Gly Trp Val Arg Gln Met Pro Gly Lys
        675                 680                 685

Gly Leu Glu Trp Met Gly Ile Ile Tyr Pro Gly Asp Ser Asp Thr Arg
    690                 695                 700

Tyr Ser Pro Ser Phe Gln Gly Gln Val Thr Ile Ser Ala Asp Lys Ser
705                 710                 715                 720

Ile Ser Thr Ala Tyr Leu Gln Trp Ser Ser Leu Lys Ala Ser Asp Thr
                725                 730                 735

Ala Met Tyr Tyr Cys Ala Arg Leu Gly Ser Ser Trp Thr Asn Asp Ala
            740                 745                 750

Phe Asp Ile Trp Gly Gln Gly Thr Met Val Thr Val Ser Ser Ala Ala
        755                 760                 765

Ala Gly Ser Asp Tyr Lys Asp Asp Asp
    770                 775

<210> SEQ ID NO 20
<211> LENGTH: 749
<212> TYPE: PRT
<213> ORGANISM: artificial
<220> FEATURE:
<223> OTHER INFORMATION: Fv polypeptide

<400> SEQUENCE: 20

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Asp Ile Val
    130                 135                 140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Ser Tyr Val Leu Thr Gln Pro Ser Ser Val Ser Val Ala Pro Gly
            260                 265                 270

Gln Thr Ala Thr Ile Ser Cys Gly Gly His Asn Ile Gly Ser Lys Asn
        275                 280                 285

Val His Trp Tyr Gln Gln Arg Pro Gly Gln Ser Pro Val Leu Val Ile
    290                 295                 300

Tyr Gln Asp Asn Lys Arg Pro Ser Gly Ile Pro Glu Arg Phe Ser Gly
305                 310                 315                 320

Ser Asn Ser Gly Asn Thr Ala Thr Leu Thr Ile Ser Gly Thr Gln Ala
                325                 330                 335

Met Asp Glu Ala Asp Tyr Tyr Cys Gln Val Trp Asp Asn Tyr Ser Val
            340                 345                 350

Leu Phe Gly Gly Gly Thr Lys Leu Thr Val Leu Gly Gly Ser Gly Gly
        355                 360                 365

Ser Gly Gly Ser Ser Tyr Val Leu Thr Gln Pro Ser Ser Val Ser Val
    370                 375                 380

Ala Pro Gly Gln Thr Ala Thr Ile Ser Cys Gly Gly His Asn Ile Gly
385                 390                 395                 400

Ser Lys Asn Val His Trp Tyr Gln Gln Arg Pro Gly Gln Ser Pro Val
```

```
            405                 410                 415
Leu Val Ile Tyr Gln Asp Asn Lys Arg Pro Ser Gly Ile Pro Glu Arg
            420                 425                 430

Phe Ser Gly Ser Asn Ser Gly Asn Thr Ala Thr Leu Thr Ile Ser Gly
            435                 440                 445

Thr Gln Ala Met Asp Glu Ala Asp Tyr Tyr Cys Gln Val Trp Asp Asn
            450                 455                 460

Tyr Ser Val Leu Phe Gly Gly Thr Lys Leu Thr Val Leu Gly Gly
465                 470                 475                 480

Ser Gly Gly Ser Gly Gly Ser Glu Val Gln Leu Val Gln Ser Gly Ala
                485                 490                 495

Glu Val Lys Lys Pro Gly Glu Ser Leu Lys Ile Ser Cys Lys Gly Ser
            500                 505                 510

Gly Tyr Ser Phe Thr Ser Asn Trp Ile Gly Trp Val Arg Gln Met Pro
            515                 520                 525

Gly Lys Gly Leu Glu Trp Met Gly Met Ile Trp Pro Gly Asp Ser Asp
            530                 535                 540

Thr Met Tyr Ser Pro Ser Phe Gln Gly Gln Val Thr Ile Ser Ala Asp
545                 550                 555                 560

Glu Ser Ile Asn Thr Ala Tyr Leu Gln Trp Ser Ser Leu Lys Ala Ser
                565                 570                 575

Asp Thr Ala Met Tyr Tyr Cys Ala Arg Arg Glu Thr Thr Thr Val Gly
            580                 585                 590

Arg Tyr Tyr Tyr Ala Met Asp Tyr Trp Gly Gln Gly Thr Leu Val Thr
            595                 600                 605

Val Ser Ser Gly Gly Ser Gly Gly Ser Gly Gly Ser Gly Gly Ser Gly
610                 615                 620

Gly Ser Gly Gly Ser Ser Tyr Val Leu Thr Gln Pro Pro Ser Val Ser
625                 630                 635                 640

Val Ala Pro Gly Gln Thr Ala Arg Ile Thr Cys Gly Gly Asn Asn Ile
            645                 650                 655

Gly Ser Lys Thr Val His Trp Tyr Gln Gln Lys Pro Gly Gln Ala Pro
            660                 665                 670

Val Leu Val Val Tyr Asp Asp Ser Asp Arg Pro Ser Gly Ile Pro Glu
            675                 680                 685

Arg Phe Ser Gly Ser Asn Ser Gly Asn Thr Ala Thr Leu Thr Ile Ser
            690                 695                 700

Arg Val Glu Ala Gly Asp Glu Ala Asp Tyr Tyr Cys Gln Val Gly Thr
705                 710                 715                 720

Asp Trp Ser Asp His Leu Gln Val Phe Gly Gly Thr Lys Leu Thr
                725                 730                 735

Val Leu Ala Ala Ala Gly Ser His His His His His
            740                 745

<210> SEQ ID NO 21
<211> LENGTH: 519
<212> TYPE: PRT
<213> ORGANISM: artificial
<220> FEATURE:
<223> OTHER INFORMATION: Fv polypeptide

<400> SEQUENCE: 21

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
```

```
                20                  25                  30
Thr Ile His Trp Val Arg Gln Arg Pro Gly His Asp Leu Glu Trp Ile
                35                  40                  45
Gly Tyr Ile Asn Pro Ser Ser Gly Tyr Ser Asp Tyr Asn Gln Asn Phe
                50                  55                  60
Lys Gly Lys Thr Thr Leu Thr Ala Asp Lys Ser Asn Thr Ala Tyr
 65                  70                  75                  80
Met Gln Leu Asn Ser Leu Thr Ser Glu Asp Ser Ala Val Tyr Tyr Cys
                85                  90                  95
Ala Arg Arg Ala Asp Tyr Gly Asn Tyr Glu Tyr Thr Trp Phe Ala Tyr
                100                 105                 110
Trp Gly Gln Gly Thr Thr Val Thr Val Ser Ser Gly Gly Ser Gly Gly
                115                 120                 125
Ser Gly Gly Ser Gly Gly Ser Gly Gly Ser Gly Gly Ser Asp Ile Val
                130                 135                 140
Met Thr Gln Ser Pro Lys Phe Met Ser Thr Ser Val Gly Asp Arg Val
145                 150                 155                 160
Thr Val Thr Cys Lys Ala Ser Gln Asn Val Gly Thr Asn Val Ala Trp
                165                 170                 175
Phe Gln Gln Lys Pro Gly Gln Ser Pro Lys Val Leu Ile Tyr Ser Ala
                180                 185                 190
Ser Tyr Arg Tyr Ser Gly Val Pro Asp Arg Phe Thr Gly Ser Gly Ser
                195                 200                 205
Gly Thr Asp Phe Thr Leu Thr Ile Ser Asn Val Gln Ser Glu Asp Leu
                210                 215                 220
Ala Glu Tyr Phe Cys Gln Gln Tyr His Thr Tyr Pro Leu Thr Phe Gly
225                 230                 235                 240
Gly Gly Thr Lys Leu Glu Ile Asn Gly Gly Ser Gly Gly Ser Gly Gly
                245                 250                 255
Ser Gln Val Gln Leu Val Gln Ser Gly Ala Glu Val Lys Lys Pro Gly
                260                 265                 270
Glu Ser Leu Lys Val Ser Cys Lys Ala Ser Gly Tyr Thr Phe Thr Ser
                275                 280                 285
Tyr Tyr Met His Trp Val Arg Gln Ala Pro Gly Gln Gly Leu Glu Trp
                290                 295                 300
Met Gly Ile Ile Asn Pro Ser Gly Gly Ser Thr Ser Tyr Ala Gln Lys
305                 310                 315                 320
Phe Gln Gly Arg Val Thr Met Thr Arg Asp Thr Ser Thr Ser Thr Val
                325                 330                 335
Tyr Met Glu Leu Ser Ser Leu Arg Ser Glu Asp Thr Ala Val Tyr Tyr
                340                 345                 350
Cys Ala Arg Gly Ser Ala Tyr Tyr Tyr Asp Phe Ala Asp Tyr Trp Gly
                355                 360                 365
Gln Gly Thr Leu Val Thr Val Ser Ser Gly Gly Ser Gly Gly Ser Gly
                370                 375                 380
Gly Ser Gln Val Gln Leu Val Gln Ser Gly Ala Glu Val Lys Lys Pro
385                 390                 395                 400
Gly Glu Ser Leu Lys Val Ser Cys Lys Ala Ser Gly Tyr Thr Phe Thr
                405                 410                 415
Ser Tyr Tyr Met His Trp Val Arg Gln Ala Pro Gly Gln Gly Leu Glu
                420                 425                 430
Trp Met Gly Ile Ile Asn Pro Ser Gly Gly Ser Thr Ser Tyr Ala Gln
                435                 440                 445
```

```
Lys Phe Gln Gly Arg Val Thr Met Thr Arg Asp Thr Ser Thr Ser Thr
    450                 455                 460
Val Tyr Met Glu Leu Ser Ser Leu Arg Ser Glu Asp Thr Ala Val Tyr
465                 470                 475                 480
Tyr Cys Ala Arg Gly Ser Ala Tyr Tyr Asp Phe Ala Asp Tyr Trp
                485                 490                 495
Gly Gln Gly Thr Leu Val Thr Val Ser Ser Ala Ala Gly Ser Asp
            500                 505                 510
Tyr Lys Asp Asp Asp Lys
        515

<210> SEQ ID NO 22
<211> LENGTH: 497
<212> TYPE: PRT
<213> ORGANISM: artificial
<220> FEATURE:
<223> OTHER INFORMATION: Fv polypeptide

<400> SEQUENCE: 22

Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Thr Tyr
            20                  25                  30
Thr Ile His Trp Val Arg Gln Arg Pro Gly His Asp Leu Glu Trp Ile
        35                  40                  45
Gly Tyr Ile Asn Pro Ser Ser Gly Tyr Ser Asp Tyr Asn Gln Asn Phe
    50                  55                  60
Lys Gly Lys Thr Thr Leu Thr Ala Asp Lys Ser Ser Asn Thr Ala Tyr
65                  70                  75                  80
Met Gln Leu Asn Ser Leu Thr Ser Glu Asp Ser Ala Val Tyr Tyr Cys
                85                  90                  95
Ala Arg Arg Ala Asp Tyr Gly Asn Tyr Glu Tyr Thr Trp Phe Ala Tyr
            100                 105                 110
Trp Gly Gln Gly Thr Thr Val Thr Val Ser Ser Gly Gly Ser Gly Gly
        115                 120                 125
Ser Gly Gly Ser Ser Tyr Val Leu Thr Gln Pro Ser Ser Val Ser Val
    130                 135                 140
Ala Pro Gly Gln Thr Ala Thr Ile Ser Cys Gly Gly His Asn Ile Gly
145                 150                 155                 160
Ser Lys Asn Val His Trp Tyr Gln Gln Arg Pro Gly Gln Ser Pro Val
                165                 170                 175
Leu Val Ile Tyr Gln Asp Asn Lys Arg Pro Ser Gly Ile Pro Glu Arg
            180                 185                 190
Phe Ser Gly Ser Asn Ser Gly Asn Thr Ala Thr Leu Thr Ile Ser Gly
        195                 200                 205
Thr Gln Ala Met Asp Glu Ala Asp Tyr Tyr Cys Gln Val Trp Asp Asn
    210                 215                 220
Tyr Ser Val Leu Phe Gly Gly Gly Thr Lys Leu Thr Val Leu Gly Gly
225                 230                 235                 240
Ser Gly Gly Ser Gly Gly Ser Ser Tyr Val Leu Thr Gln Pro Ser Ser
                245                 250                 255
Val Ser Val Ala Pro Gly Gln Thr Ala Thr Ile Ser Cys Gly Gly His
            260                 265                 270
Asn Ile Gly Ser Lys Asn Val His Trp Tyr Gln Gln Arg Pro Gly Gln
        275                 280                 285
```

Ser Pro Val Leu Val Ile Tyr Gln Asp Asn Lys Arg Pro Ser Gly Ile
            290                 295                 300

Pro Glu Arg Phe Ser Gly Ser Asn Ser Gly Asn Thr Ala Thr Leu Thr
305                 310                 315                 320

Ile Ser Gly Thr Gln Ala Met Asp Glu Ala Asp Tyr Tyr Cys Gln Val
                325                 330                 335

Trp Asp Asn Tyr Ser Val Leu Phe Gly Gly Thr Lys Leu Thr Val
                340                 345                 350

Leu Gly Gly Ser Gly Gly Ser Gly Gly Ser Glu Val Gln Leu Val Gln
            355                 360                 365

Ser Gly Ala Glu Val Lys Lys Pro Gly Glu Ser Leu Lys Ile Ser Cys
            370                 375                 380

Lys Gly Ser Gly Tyr Ser Phe Thr Ser Asn Trp Ile Gly Trp Val Arg
385                 390                 395                 400

Gln Met Pro Gly Lys Gly Leu Glu Trp Met Gly Met Ile Trp Pro Gly
                405                 410                 415

Asp Ser Asp Thr Met Tyr Ser Pro Ser Phe Gln Gly Gln Val Thr Ile
                420                 425                 430

Ser Ala Asp Glu Ser Ile Asn Thr Ala Tyr Leu Gln Trp Ser Ser Leu
            435                 440                 445

Lys Ala Ser Asp Thr Ala Met Tyr Tyr Cys Ala Arg Arg Glu Thr Thr
450                 455                 460

Thr Val Gly Arg Tyr Tyr Tyr Ala Met Asp Tyr Trp Gly Gln Gly Thr
465                 470                 475                 480

Leu Val Thr Val Ser Ser Ala Ala Gly Ser His His His His
                485                 490                 495

His

<210> SEQ ID NO 23
<211> LENGTH: 493
<212> TYPE: PRT
<213> ORGANISM: artificial
<220> FEATURE:
<223> OTHER INFORMATION: Fv polypeptide

<400> SEQUENCE: 23

Ser Tyr Val Leu Thr Gln Pro Ser Val Ser Val Ala Pro Gly Gln
1               5                   10                  15

Thr Ala Arg Ile Thr Cys Gly Gly Asn Asn Ile Gly Ser Lys Thr Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Gly Thr Asp Trp Ser Asp His
                85                  90                  95

Leu Gln Val Phe Gly Gly Thr Lys Leu Thr Val Leu Gly Gly Ser
                100                 105                 110

Gly Gly Ser Gln Val Gln Leu Val Gln Ser Gly Ala Glu Val Lys Lys
            115                 120                 125

Pro Gly Glu Ser Leu Lys Val Ser Cys Lys Ala Ser Gly Tyr Thr Phe
130                 135                 140

Thr Ser Tyr Tyr Met His Trp Val Arg Gln Ala Pro Gly Gln Gly Leu
145                 150                 155                 160

Glu Trp Met Gly Ile Ile Asn Pro Ser Gly Gly Ser Thr Ser Tyr Ala
            165                 170                 175

Gln Lys Phe Gln Gly Arg Val Thr Met Thr Arg Asp Thr Ser Thr Ser
        180                 185                 190

Thr Val Tyr Met Glu Leu Ser Ser Leu Arg Ser Glu Asp Thr Ala Val
    195                 200                 205

Tyr Tyr Cys Ala Arg Gly Ser Ala Tyr Tyr Asp Phe Ala Asp Tyr
210                 215                 220

Trp Gly Gln Gly Thr Leu Val Thr Val Ser Ser Gly Gly Ser Gly Gly
225                 230                 235                 240

Ser Gly Gly Ser Gln Val Gln Leu Val Gln Ser Gly Ala Glu Val Lys
            245                 250                 255

Lys Pro Gly Glu Ser Leu Lys Val Ser Cys Lys Ala Ser Gly Tyr Thr
        260                 265                 270

Phe Thr Ser Tyr Tyr Met His Trp Val Arg Gln Ala Pro Gly Gln Gly
    275                 280                 285

Leu Glu Trp Met Gly Ile Ile Asn Pro Ser Gly Gly Ser Thr Ser Tyr
290                 295                 300

Ala Gln Lys Phe Gln Gly Arg Val Thr Met Thr Arg Asp Thr Ser Thr
305                 310                 315                 320

Ser Thr Val Tyr Met Glu Leu Ser Ser Leu Arg Ser Glu Asp Thr Ala
            325                 330                 335

Val Tyr Tyr Cys Ala Arg Gly Ser Ala Tyr Tyr Asp Phe Ala Asp
        340                 345                 350

Tyr Trp Gly Gln Gly Thr Leu Val Thr Val Ser Ser Gly Gly Ser Gly
    355                 360                 365

Gly Ser Gly Gly Ser Asp Ile Val Met Thr Gln Ser Pro Lys Phe Met
370                 375                 380

Ser Thr Ser Val Gly Asp Arg Val Thr Val Thr Cys Lys Ala Ser Gln
385                 390                 395                 400

Asn Val Gly Thr Asn Val Ala Trp Phe Gln Gln Lys Pro Gly Gln Ser
            405                 410                 415

Pro Lys Val Leu Ile Tyr Ser Ala Ser Tyr Arg Tyr Ser Gly Val Pro
        420                 425                 430

Asp Arg Phe Thr Gly Ser Gly Ser Gly Thr Asp Phe Thr Leu Thr Ile
    435                 440                 445

Ser Asn Val Gln Ser Glu Asp Leu Ala Glu Tyr Phe Cys Gln Gln Tyr
450                 455                 460

His Thr Tyr Pro Leu Thr Phe Gly Gly Gly Thr Lys Leu Glu Ile Asn
465                 470                 475                 480

Ala Ala Ala Gly Ser Asp Tyr Lys Asp Asp Asp Lys
            485                 490

<210> SEQ ID NO 24
<211> LENGTH: 757
<212> TYPE: PRT
<213> ORGANISM: artificial
<220> FEATURE:
<223> OTHER INFORMATION: Fv polypeptide

<400> SEQUENCE: 24

Gln Val Gln Leu Gln Gln Ser Gly Ala Glu Leu Ala Arg Pro Gly Ala
1               5                   10                  15

-continued

```
Ser Val Lys Met Ser Cys Lys Ala Ser Gly Tyr Thr Phe Thr Thr Tyr
             20                  25                  30

Thr Ile His Trp Val Arg Gln Arg Pro Gly His Asp Leu Glu Trp Ile
         35                  40                  45

Gly Tyr Ile Asn Pro Ser Ser Gly Tyr Ser Asp Tyr Asn Gln Asn Phe
     50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                 85                  90                  95

Ala Arg Arg Ala Asp Tyr Gly Asn Tyr Glu Tyr Thr Trp Phe Ala Tyr
                100                 105                 110

Trp Gly Gln Gly Thr Thr Val Thr Val Ser Ser Gly Gly Ser Gly Gly
            115                 120                 125

Ser Gly Gly Ser Ser Tyr Val Leu Thr Gln Pro Ser Ser Val Ser Val
        130                 135                 140

Ala Pro Gly Gln Thr Ala Thr Ile Ser Cys Gly Gly His Asn Ile Gly
145                 150                 155                 160

Ser Lys Asn Val His Trp Tyr Gln Gln Arg Pro Gly Gln Ser Pro Val
                165                 170                 175

Leu Val Ile Tyr Gln Asp Asn Lys Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Met Asp Glu Ala Asp Tyr Tyr Cys Gln Val Trp Asp Asn
210                 215                 220

Tyr Ser Val Leu Phe Gly Gly Gly Thr Lys Leu Thr Val Leu Gly Gly
225                 230                 235                 240

Ser Gly Gly Ser Gly Gly Ser Ser Tyr Val Leu Thr Gln Pro Ser Ser
                245                 250                 255

Val Ser Val Ala Pro Gly Gln Thr Ala Thr Ile Ser Cys Gly Gly His
            260                 265                 270

Asn Ile Gly Ser Lys Asn Val His Trp Tyr Gln Gln Arg Pro Gly Gln
        275                 280                 285

Ser Pro Val Leu Val Ile Tyr Gln Asp Asn Lys Arg Pro Ser Gly Ile
    290                 295                 300

Pro Glu Arg Phe Ser Gly Ser Asn Ser Gly Asn Thr Ala Thr Leu Thr
305                 310                 315                 320

Ile Ser Gly Thr Gln Ala Met Asp Glu Ala Asp Tyr Tyr Cys Gln Val
                325                 330                 335

Trp Asp Asn Tyr Ser Val Leu Phe Gly Gly Gly Thr Lys Leu Thr Val
            340                 345                 350

Leu Gly Gly Ser Gly Gly Ser Gly Gly Ser Glu Val Gln Leu Val Gln
        355                 360                 365

Ser Gly Ala Glu Val Lys Lys Pro Gly Glu Ser Leu Lys Ile Ser Cys
    370                 375                 380

Lys Gly Ser Gly Tyr Ser Phe Thr Ser Asn Trp Ile Gly Trp Val Arg
385                 390                 395                 400

Gln Met Pro Gly Lys Gly Leu Glu Trp Met Gly Met Ile Trp Pro Gly
                405                 410                 415

Asp Ser Asp Thr Met Tyr Ser Pro Ser Phe Gln Gly Gln Val Thr Ile
            420                 425                 430

Ser Ala Asp Glu Ser Ile Asn Thr Ala Tyr Leu Gln Trp Ser Ser Leu
```

```
               435                 440                 445
Lys Ala Ser Asp Thr Ala Met Tyr Tyr Cys Ala Arg Arg Glu Thr Thr
450                 455                 460

Thr Val Gly Arg Tyr Tyr Ala Met Asp Tyr Trp Gly Gln Gly Thr
465                 470                 475                 480

Leu Val Thr Val Ser Ser Gly Gly Ser Gly Gly Ser
                    485                 490                 495

Tyr Glu Leu Thr Gln Pro Pro Ser Val Ser Val Ser Pro Gly Gln Thr
                500                 505                 510

Ala Arg Ile Thr Cys Ser Gly Asp Ala Leu Pro Lys Gln Tyr Ala Tyr
                515                 520                 525

Trp Tyr Gln Gln Lys Pro Gly Gln Ala Pro Val Leu Val Ile Tyr Lys
                530                 535                 540

Asp Ser Glu Arg Pro Ser Gly Ile Pro Glu Arg Phe Ser Gly Ser Ser
545                 550                 555                 560

Ser Gly Thr Thr Val Thr Leu Thr Ile Ser Gly Val Gln Ala Glu Asp
                    565                 570                 575

Glu Ala Asp Tyr Tyr Cys Gln Ser Ala Asp Ser Ser Gly Thr Pro Leu
                580                 585                 590

Ile Val Phe Gly Thr Gly Thr Lys Leu Thr Val Leu Gly Gly Ser Gly
                595                 600                 605

Gly Ser Gly Gly Ser Gly Gly Ser Gly Gly Ser Gly Gly Ser Gly Gly
                    610                 615                 620

Ser Glu Val Gln Leu Val Gln Ser Gly Ala Glu Val Lys Lys Pro Gly
625                 630                 635                 640

Glu Ser Leu Lys Ile Ser Cys Lys Gly Ser Gly Tyr Ser Phe Thr Ser
                    645                 650                 655

Tyr Trp Ile Gly Trp Val Arg Gln Met Pro Gly Lys Gly Leu Glu Trp
                660                 665                 670

Met Gly Ile Ile Tyr Pro Gly Asp Ser Asp Thr Arg Tyr Ser Pro Ser
                675                 680                 685

Phe Gln Gly Gln Val Thr Ile Ser Ala Asp Lys Ser Ile Ser Thr Ala
690                 695                 700

Tyr Leu Gln Trp Ser Ser Leu Lys Ala Ser Asp Thr Ala Met Tyr Tyr
705                 710                 715                 720

Cys Ala Arg Leu Gly Ser Ser Trp Thr Asn Asp Ala Phe Asp Ile Trp
                    725                 730                 735

Gly Gln Gly Thr Met Val Thr Val Ser Ser Ala Ala Ala Gly Ser His
                740                 745                 750

His His His His His
        755

<210> SEQ ID NO 25
<211> LENGTH: 753
<212> TYPE: PRT
<213> ORGANISM: artificial
<220> FEATURE:
<223> OTHER INFORMATION: Fv polypeptide

<400> SEQUENCE: 25

Ser Tyr Val Leu Thr Gln Pro Pro Ser Val Ser Val Ala Pro Gly Gln
1                   5                   10                  15

Thr Ala Arg Ile Thr Cys Gly Gly Asn Asn Ile Gly Ser Lys Thr Val
                    20                  25                  30

His Trp Tyr Gln Gln Lys Pro Gly Gln Ala Pro Val Leu Val Val Tyr
```

```
                35                  40                  45
Asp Asp Ser Asp Arg Pro Ser Gly Ile Pro Glu Arg Phe Ser Gly Ser
                    50                  55                  60
Asn Ser Gly Asn Thr Ala Thr Leu Thr Ile Ser Arg Val Glu Ala Gly
 65                  70                  75                  80
Asp Glu Ala Asp Tyr Tyr Cys Gln Val Gly Thr Asp Trp Ser Asp His
                85                  90                  95
Leu Gln Val Phe Gly Gly Gly Thr Lys Leu Thr Val Leu Gly Gly Ser
                100                 105                 110
Gly Gly Ser Gln Val Gln Leu Val Gln Ser Gly Ala Glu Val Lys Lys
                115                 120                 125
Pro Gly Glu Ser Leu Lys Val Ser Cys Lys Ala Ser Gly Tyr Thr Phe
                130                 135                 140
Thr Ser Tyr Tyr Met His Trp Val Arg Gln Ala Pro Gly Gln Gly Leu
145                 150                 155                 160
Glu Trp Met Gly Ile Ile Asn Pro Ser Gly Gly Ser Thr Ser Tyr Ala
                165                 170                 175
Gln Lys Phe Gln Gly Arg Val Thr Met Thr Arg Asp Thr Ser Thr Ser
                180                 185                 190
Thr Val Tyr Met Glu Leu Ser Ser Leu Arg Ser Glu Asp Thr Ala Val
                195                 200                 205
Tyr Tyr Cys Ala Arg Gly Ser Ala Tyr Tyr Asp Phe Ala Asp Tyr
                210                 215                 220
Trp Gly Gln Gly Thr Leu Val Thr Val Ser Ser Gly Gly Ser Gly Gly
225                 230                 235                 240
Ser Gly Gly Ser Gln Val Gln Leu Val Gln Ser Gly Ala Glu Val Lys
                245                 250                 255
Lys Pro Gly Glu Ser Leu Lys Val Ser Cys Lys Ala Ser Gly Tyr Thr
                260                 265                 270
Phe Thr Ser Tyr Tyr Met His Trp Val Arg Gln Ala Pro Gly Gln Gly
                275                 280                 285
Leu Glu Trp Met Gly Ile Ile Asn Pro Ser Gly Gly Ser Thr Ser Tyr
                290                 295                 300
Ala Gln Lys Phe Gln Gly Arg Val Thr Met Thr Arg Asp Thr Ser Thr
305                 310                 315                 320
Ser Thr Val Tyr Met Glu Leu Ser Ser Leu Arg Ser Glu Asp Thr Ala
                325                 330                 335
Val Tyr Tyr Cys Ala Arg Gly Ser Ala Tyr Tyr Asp Phe Ala Asp
                340                 345                 350
Tyr Trp Gly Gln Gly Thr Leu Val Thr Val Ser Ser Gly Gly Ser Gly
                355                 360                 365
Gly Ser Gly Gly Ser Asp Ile Val Met Thr Gln Ser Pro Lys Phe Met
                370                 375                 380
Ser Thr Ser Val Gly Asp Arg Val Thr Val Thr Cys Lys Ala Ser Gln
385                 390                 395                 400
Asn Val Gly Thr Asn Val Ala Trp Phe Gln Gln Lys Pro Gly Gln Ser
                405                 410                 415
Pro Lys Val Leu Ile Tyr Ser Ala Ser Tyr Arg Tyr Ser Gly Val Pro
                420                 425                 430
Asp Arg Phe Thr Gly Ser Gly Ser Gly Thr Asp Phe Thr Leu Thr Ile
                435                 440                 445
Ser Asn Val Gln Ser Glu Asp Leu Ala Glu Tyr Phe Cys Gln Gln Tyr
                450                 455                 460
```

His Thr Tyr Pro Leu Thr Phe Gly Gly Gly Thr Lys Leu Glu Ile Asn
465                 470                 475                 480

Gly Gly Ser Gly Gly Ser Gly Ser Ser Tyr Glu Leu Thr Gln Pro
            485                 490                 495

Pro Ser Val Ser Val Ser Pro Gly Gln Thr Ala Arg Ile Thr Cys Ser
            500                 505                 510

Gly Asp Ala Leu Pro Lys Gln Tyr Ala Tyr Trp Tyr Gln Gln Lys Pro
            515                 520                 525

Gly Gln Ala Pro Val Leu Val Ile Tyr Lys Asp Ser Glu Arg Pro Ser
530                 535                 540

Gly Ile Pro Glu Arg Phe Ser Gly Ser Ser Ser Gly Thr Thr Val Thr
545                 550                 555                 560

Leu Thr Ile Ser Gly Val Gln Ala Glu Asp Glu Ala Asp Tyr Tyr Cys
                565                 570                 575

Gln Ser Ala Asp Ser Ser Gly Thr Pro Leu Ile Val Phe Gly Thr Gly
                580                 585                 590

Thr Lys Leu Thr Val Leu Gly Gly Gly Ser Gly Gly Ser Gly
            595                 600                 605

Gly Ser Gly Gly Ser Gly Gly Ser Glu Val Gln Leu Val
610                 615                 620

Gln Ser Gly Ala Glu Val Lys Lys Pro Gly Glu Ser Leu Lys Ile Ser
625                 630                 635                 640

Cys Lys Gly Ser Gly Tyr Ser Phe Thr Ser Tyr Trp Ile Gly Trp Val
                645                 650                 655

Arg Gln Met Pro Gly Lys Gly Leu Glu Trp Met Gly Ile Ile Tyr Pro
            660                 665                 670

Gly Asp Ser Asp Thr Arg Tyr Ser Pro Ser Phe Gln Gly Gln Val Thr
            675                 680                 685

Ile Ser Ala Asp Lys Ser Ile Ser Thr Ala Tyr Leu Gln Trp Ser Ser
690                 695                 700

Leu Lys Ala Ser Asp Thr Ala Met Tyr Tyr Cys Ala Arg Leu Gly Ser
705                 710                 715                 720

Ser Trp Thr Asn Asp Ala Phe Asp Ile Trp Gly Gln Gly Thr Met Val
                725                 730                 735

Thr Val Ser Ser Ala Ala Ala Gly Ser Asp Tyr Lys Asp Asp Asp Asp
            740                 745                 750

Lys

<210> SEQ ID NO 26
<211> LENGTH: 754
<212> TYPE: PRT
<213> ORGANISM: artificial
<220> FEATURE:
<223> OTHER INFORMATION: Fv polypeptide

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

-continued

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Ser Ser Trp Thr Asn Asp Ala Phe Asp Ile Trp Gly
            100                 105                 110

Gln Gly Thr Met Val Thr Val Ser Ser Gly Ser Gly Gly Ser Gly
        115                 120                 125

Gly Ser Gly Gly Ser Gly Gly Ser Gly Gly Ser Ser Tyr Glu Leu Thr
    130                 135                 140

Gln Pro Pro Ser Val Ser Val Ser Pro Gly Gln Thr Ala Arg Ile Thr
145                 150                 155                 160

Cys Ser Gly Asp Ala Leu Pro Lys Gln Tyr Ala Tyr Trp Tyr Gln Gln
                165                 170                 175

Lys Pro Gly Gln Ala Pro Val Leu Val Ile Tyr Lys Asp Ser Glu Arg
            180                 185                 190

Pro Ser Gly Ile Pro Glu Arg Phe Ser Gly Ser Ser Ser Gly Thr Thr
        195                 200                 205

Val Thr Leu Thr Ile Ser Gly Val Gln Ala Glu Asp Glu Ala Asp Tyr
    210                 215                 220

Tyr Cys Gln Ser Ala Asp Ser Ser Gly Thr Pro Leu Ile Val Phe Gly
225                 230                 235                 240

Thr Gly Thr Lys Leu Thr Val Leu Gly Gly Ser Gly Gly Ser Gly Gly
                245                 250                 255

Ser Gln Val Gln Leu Gln Gln Ser Gly Ala Glu Leu Ala Arg Pro Gly
            260                 265                 270

Ala Ser Val Lys Met Ser Cys Lys Ala Ser Gly Tyr Thr Phe Thr Thr
        275                 280                 285

Tyr Thr Ile His Trp Val Arg Gln Arg Pro Gly His Asp Leu Glu Trp
    290                 295                 300

Ile Gly Tyr Ile Asn Pro Ser Ser Gly Tyr Ser Asp Tyr Asn Gln Asn
305                 310                 315                 320

Phe Lys Gly Lys Thr Thr Leu Thr Ala Asp Lys Ser Ser Asn Thr Ala
                325                 330                 335

Tyr Met Gln Leu Asn Ser Leu Thr Ser Glu Asp Ser Ala Val Tyr Tyr
            340                 345                 350

Cys Ala Arg Arg Ala Asp Tyr Gly Asn Tyr Glu Tyr Thr Trp Phe Ala
        355                 360                 365

Tyr Trp Gly Gln Gly Thr Thr Val Thr Val Ser Ser Gly Gly Ser Gly
    370                 375                 380

Gly Ser Gly Gly Ser Ser Tyr Val Leu Thr Gln Pro Ser Ser Val Ser
385                 390                 395                 400

Val Ala Pro Gly Gln Thr Ala Thr Ile Ser Cys Gly Gly His Asn Ile
                405                 410                 415

Gly Ser Lys Asn Val His Trp Tyr Gln Gln Arg Pro Gly Gln Ser Pro
            420                 425                 430

Val Leu Val Ile Tyr Gln Asp Asn Lys Arg Pro Ser Gly Ile Pro Glu
        435                 440                 445

Arg Phe Ser Gly Ser Asn Ser Gly Asn Thr Ala Thr Leu Thr Ile Ser
    450                 455                 460

Gly Thr Gln Ala Met Asp Glu Ala Asp Tyr Tyr Cys Gln Val Trp Asp
465                 470                 475                 480

Asn Tyr Ser Val Leu Phe Gly Gly Gly Thr Lys Leu Thr Val Leu Gly
```

```
            485                 490                 495
Gly Ser Gly Gly Ser Gly Gly Ser Ser Tyr Val Leu Thr Gln Pro Ser
            500                 505                 510

Ser Val Ser Val Ala Pro Gly Gln Thr Ala Thr Ile Ser Cys Gly Gly
            515                 520                 525

His Asn Ile Gly Ser Lys Asn Val His Trp Tyr Gln Gln Arg Pro Gly
            530                 535                 540

Gln Ser Pro Val Leu Val Ile Tyr Gln Asp Asn Lys Arg Pro Ser Gly
545                 550                 555                 560

Ile Pro Glu Arg Phe Ser Gly Ser Asn Ser Gly Asn Thr Ala Thr Leu
                565                 570                 575

Thr Ile Ser Gly Thr Gln Ala Met Asp Glu Ala Asp Tyr Tyr Cys Gln
            580                 585                 590

Val Trp Asp Asn Tyr Ser Val Leu Phe Gly Gly Gly Thr Lys Leu Thr
            595                 600                 605

Val Leu Gly Gly Ser Gly Gly Ser Gly Gly Ser Glu Val Gln Leu Val
            610                 615                 620

Gln Ser Gly Ala Glu Val Lys Lys Pro Gly Glu Ser Leu Lys Ile Ser
625                 630                 635                 640

Cys Lys Gly Ser Gly Tyr Ser Phe Thr Ser Asn Trp Ile Gly Trp Val
                645                 650                 655

Arg Gln Met Pro Gly Lys Gly Leu Glu Trp Met Gly Met Ile Trp Pro
                660                 665                 670

Gly Asp Ser Asp Thr Met Tyr Ser Pro Ser Phe Gln Gly Gln Val Thr
            675                 680                 685

Ile Ser Ala Asp Glu Ser Ile Asn Thr Ala Tyr Leu Gln Trp Ser Ser
            690                 695                 700

Leu Lys Ala Ser Asp Thr Ala Met Tyr Tyr Cys Ala Arg Arg Glu Thr
705                 710                 715                 720

Thr Thr Val Gly Arg Tyr Tyr Tyr Ala Met Asp Tyr Trp Gly Gln Gly
                725                 730                 735

Thr Leu Val Thr Val Ser Ser Ala Ala Ala Gly Ser His His His His
            740                 745                 750

His His

<210> SEQ ID NO 27
<211> LENGTH: 750
<212> TYPE: PRT
<213> ORGANISM: artificial
<220> FEATURE:
<223> OTHER INFORMATION: Fv polypeptide

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65              70                  75                  80

Leu Gln Trp Ser Ser Leu Lys Ala Ser Asp Thr Ala Met Tyr Tyr Cys
            85                  90                  95
```

```
Ala Arg Leu Gly Ser Ser Trp Thr Asn Asp Ala Phe Asp Ile Trp Gly
            100                 105                 110

Gln Gly Thr Met Val Thr Val Ser Gly Gly Ser Gly Gly Ser Gly
            115                 120                 125

Gly Ser Gly Gly Ser Gly Gly Ser Gly Gly Ser Ser Tyr Glu Leu Thr
            130                 135                 140

Gln Pro Pro Ser Val Ser Val Ser Pro Gly Gln Thr Ala Arg Ile Thr
145                 150                 155                 160

Cys Ser Gly Asp Ala Leu Pro Lys Gln Tyr Ala Tyr Trp Tyr Gln Gln
                165                 170                 175

Lys Pro Gly Gln Ala Pro Val Leu Val Ile Tyr Lys Asp Ser Glu Arg
                180                 185                 190

Pro Ser Gly Ile Pro Glu Arg Phe Ser Gly Ser Ser Ser Gly Thr Thr
                195                 200                 205

Val Thr Leu Thr Ile Ser Gly Val Gln Ala Glu Asp Glu Ala Asp Tyr
            210                 215                 220

Tyr Cys Gln Ser Ala Asp Ser Ser Gly Thr Pro Leu Ile Val Phe Gly
225                 230                 235                 240

Thr Gly Thr Lys Leu Thr Val Leu Gly Gly Ser Gly Gly Ser Gly Gly
                245                 250                 255

Ser Ser Tyr Val Leu Thr Gln Pro Pro Ser Val Ser Val Ala Pro Gly
                260                 265                 270

Gln Thr Ala Arg Ile Thr Cys Gly Gly Asn Asn Ile Gly Ser Lys Thr
            275                 280                 285

Val His Trp Tyr Gln Gln Lys Pro Gly Gln Ala Pro Val Leu Val Val
            290                 295                 300

Tyr Asp Asp Ser Asp Arg Pro Ser Gly Ile Pro Glu Arg Phe Ser Gly
305                 310                 315                 320

Ser Asn Ser Gly Asn Thr Ala Thr Leu Thr Ile Ser Arg Val Glu Ala
                325                 330                 335

Gly Asp Glu Ala Asp Tyr Tyr Cys Gln Val Gly Thr Asp Trp Ser Asp
                340                 345                 350

His Leu Gln Val Phe Gly Gly Gly Thr Lys Leu Thr Val Leu Gly Gly
            355                 360                 365

Ser Gly Gly Ser Gln Val Gln Leu Val Gln Ser Gly Ala Glu Val Lys
            370                 375                 380

Lys Pro Gly Glu Ser Leu Lys Val Ser Cys Lys Ala Ser Gly Tyr Thr
385                 390                 395                 400

Phe Thr Ser Tyr Tyr Met His Trp Val Arg Gln Ala Pro Gly Gln Gly
                405                 410                 415

Leu Glu Trp Met Gly Ile Ile Asn Pro Ser Gly Gly Ser Thr Ser Tyr
                420                 425                 430

Ala Gln Lys Phe Gln Gly Arg Val Thr Met Thr Arg Asp Thr Ser Thr
            435                 440                 445

Ser Thr Val Tyr Met Glu Leu Ser Ser Leu Arg Ser Glu Asp Thr Ala
            450                 455                 460

Val Tyr Tyr Cys Ala Arg Gly Ser Ala Tyr Tyr Asp Phe Ala Asp
465                 470                 475                 480

Tyr Trp Gly Gln Gly Thr Leu Val Thr Val Ser Ser Gly Gly Ser Gly
                485                 490                 495

Gly Ser Gly Gly Ser Gln Val Gln Leu Val Gln Ser Gly Ala Glu Val
            500                 505                 510
```

Lys Lys Pro Gly Glu Ser Leu Lys Val Ser Cys Lys Ala Ser Gly Tyr
            515                 520                 525

Thr Phe Thr Ser Tyr Tyr Met His Trp Val Arg Gln Ala Pro Gly Gln
        530                 535                 540

Gly Leu Glu Trp Met Gly Ile Ile Asn Pro Ser Gly Gly Ser Thr Ser
545                 550                 555                 560

Tyr Ala Gln Lys Phe Gln Gly Arg Val Thr Met Thr Arg Asp Thr Ser
                565                 570                 575

Thr Ser Thr Val Tyr Met Glu Leu Ser Ser Leu Arg Ser Glu Asp Thr
                580                 585                 590

Ala Val Tyr Tyr Cys Ala Arg Gly Ser Ala Tyr Tyr Asp Phe Ala
            595                 600                 605

Asp Tyr Trp Gly Gln Gly Thr Leu Val Thr Val Ser Ser Gly Gly Ser
        610                 615                 620

Gly Gly Ser Gly Gly Ser Asp Ile Val Met Thr Gln Ser Pro Lys Phe
625                 630                 635                 640

Met Ser Thr Ser Val Gly Asp Arg Val Thr Val Thr Cys Lys Ala Ser
                645                 650                 655

Gln Asn Val Gly Thr Asn Val Ala Trp Phe Gln Gln Lys Pro Gly Gln
                660                 665                 670

Ser Pro Lys Val Leu Ile Tyr Ser Ala Ser Tyr Arg Tyr Ser Gly Val
            675                 680                 685

Pro Asp Arg Phe Thr Gly Ser Gly Ser Gly Thr Asp Phe Thr Leu Thr
        690                 695                 700

Ile Ser Asn Val Gln Ser Glu Asp Leu Ala Glu Tyr Phe Cys Gln Gln
705                 710                 715                 720

Tyr His Thr Tyr Pro Leu Thr Phe Gly Gly Gly Thr Lys Leu Glu Ile
                725                 730                 735

Asn Ala Ala Ala Gly Ser Asp Tyr Lys Asp Asp Asp Lys
            740                 745                 750

<210> SEQ ID NO 28
<211> LENGTH: 1016
<212> TYPE: PRT
<213> ORGANISM: artificial
<220> FEATURE:
<223> OTHER INFORMATION: Fv polypeptide

<400> SEQUENCE: 28

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

```
Ser Gly Gly Ser Gly Gly Ser Gly Gly Ser Asp Ile Val
    130             135             140

Met Thr Gln Ser Pro Lys Phe Met Ser Thr Ser Val Gly Asp Arg Val
145                 150                 155                 160

Thr Val Thr Cys Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Asn Gly Gly Ser Gly Gly Ser Gly Gly
                245                 250                 255

Ser Gln Val Gln Leu Val Gln Ser Gly Ala Glu Val Lys Lys Pro Gly
            260                 265                 270

Glu Ser Leu Lys Val Ser Cys Lys Ala Ser Gly Tyr Thr Phe Thr Ser
        275                 280                 285

Tyr Tyr Met His Trp Val Arg Gln Ala Pro Gly Gln Gly Leu Glu Trp
    290                 295                 300

Met Gly Ile Ile Asn Pro Ser Gly Gly Ser Thr Ser Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Gly Ser Ala Tyr Tyr Asp Phe Ala Asp Tyr Trp Gly
        355                 360                 365

Gln Gly Thr Leu Val Thr Val Ser Ser Gly Gly Ser Gly
    370                 375                 380

Gly Ser Gln Val Gln Leu Val Gln Ser Gly Ala Glu Val Lys Lys Pro
385                 390                 395                 400

Gly Glu Ser Leu Lys Val Ser Cys Lys Ala Ser Gly Tyr Thr Phe Thr
                405                 410                 415

Ser Tyr Tyr Met His Trp Val Arg Gln Ala Pro Gly Gln Gly Leu Glu
            420                 425                 430

Trp Met Gly Ile Ile Asn Pro Ser Gly Gly Ser Thr Ser Tyr Ala Gln
        435                 440                 445

Lys Phe Gln Gly Arg Val Thr Met Thr Arg Asp Thr Ser Thr Ser Thr
    450                 455                 460

Val Tyr Met Glu Leu Ser Ser Leu Arg Ser Glu Asp Thr Ala Val Tyr
465                 470                 475                 480

Tyr Cys Ala Arg Gly Ser Ala Tyr Tyr Asp Phe Ala Asp Tyr Trp
                485                 490                 495

Gly Gln Gly Thr Leu Val Thr Val Ser Ser Gly Gly Ser Gly Gly Ser
            500                 505                 510

Gly Gly Ser Gly Gly Ser Gly Gly Ser Ser Tyr Val Leu
        515                 520                 525

Thr Gln Pro Ser Ser Val Ser Val Ala Pro Gly Gln Thr Ala Thr Ile
    530                 535                 540

Ser Cys Gly Gly His Asn Ile Gly Ser Lys Asn Val His Trp Tyr Gln
```

```
545                 550                 555                 560
Gln Arg Pro Gly Gln Ser Pro Val Leu Val Ile Tyr Gln Asp Asn Lys
                565                 570                 575
Arg Pro Ser Gly Ile Pro Glu Arg Phe Ser Gly Ser Asn Ser Gly Asn
                580                 585                 590
Thr Ala Thr Leu Thr Ile Ser Gly Thr Gln Ala Met Asp Glu Ala Asp
                595                 600                 605
Tyr Tyr Cys Gln Val Trp Asp Asn Tyr Ser Val Leu Phe Gly Gly Gly
            610                 615                 620
Thr Lys Leu Thr Val Leu Gly Ser Gly Gly Ser Gly Gly Ser Ser
625                 630                 635                 640
Tyr Val Leu Thr Gln Pro Ser Ser Val Ser Val Ala Pro Gly Gln Thr
                645                 650                 655
Ala Thr Ile Ser Cys Gly Gly His Asn Ile Gly Ser Lys Asn Val His
                660                 665                 670
Trp Tyr Gln Gln Arg Pro Gly Gln Ser Pro Val Leu Val Ile Tyr Gln
            675                 680                 685
Asp Asn Lys Arg Pro Ser Gly Ile Pro Glu Arg Phe Ser Gly Ser Asn
            690                 695                 700
Ser Gly Asn Thr Ala Thr Leu Thr Ile Ser Gly Thr Gln Ala Met Asp
705                 710                 715                 720
Glu Ala Asp Tyr Tyr Cys Gln Val Trp Asp Asn Tyr Ser Val Leu Phe
                725                 730                 735
Gly Gly Gly Thr Lys Leu Thr Val Leu Gly Ser Gly Gly Ser Gly Ser
                740                 745                 750
Gly Ser Glu Val Gln Leu Val Gln Ser Gly Ala Glu Val Lys Lys Pro
            755                 760                 765
Gly Glu Ser Leu Lys Ile Ser Cys Lys Gly Ser Gly Tyr Ser Phe Thr
            770                 775                 780
Ser Asn Trp Ile Gly Trp Val Arg Gln Met Pro Gly Lys Gly Leu Glu
785                 790                 795                 800
Trp Met Gly Met Ile Trp Pro Gly Asp Ser Asp Thr Met Tyr Ser Pro
                805                 810                 815
Ser Phe Gln Gly Gln Val Thr Ile Ser Ala Asp Glu Ser Ile Asn Thr
                820                 825                 830
Ala Tyr Leu Gln Trp Ser Ser Leu Lys Ala Ser Asp Thr Ala Met Tyr
                835                 840                 845
Tyr Cys Ala Arg Arg Glu Thr Thr Thr Val Gly Arg Tyr Tyr Tyr Ala
850                 855                 860
Met Asp Tyr Trp Gly Gln Gly Thr Leu Val Thr Val Ser Ser Gly Gly
865                 870                 875                 880
Ser Gly Gly Ser Gly Gly Ser Gly Gly Ser Gly Gly Ser Gly Gly Ser
                885                 890                 895
Ser Tyr Val Leu Thr Gln Pro Pro Ser Val Ser Val Ala Pro Gly Gln
                900                 905                 910
Thr Ala Arg Ile Thr Cys Gly Gly Asn Asn Ile Gly Ser Lys Thr Val
                915                 920                 925
His Trp Tyr Gln Gln Lys Pro Gly Gln Ala Pro Val Leu Val Val Tyr
            930                 935                 940
Asp Asp Ser Asp Arg Pro Ser Gly Ile Pro Glu Arg Phe Ser Gly Ser
945                 950                 955                 960
Asn Ser Gly Asn Thr Ala Thr Leu Thr Ile Ser Arg Val Glu Ala Gly
                965                 970                 975
```

```
Asp Glu Ala Asp Tyr Tyr Cys Gln Val Gly Thr Asp Trp Ser Asp His
            980                 985                 990

Leu Gln Val Phe Gly Gly Gly Thr Lys Leu Thr Val Leu Ala Ala Ala
            995                1000                1005

Gly Ser His His His His His His
    1010                1015

<210> SEQ ID NO 29
<211> LENGTH: 1521
<212> TYPE: PRT
<213> ORGANISM: artificial
<220> FEATURE:
<223> OTHER INFORMATION: Fv polypeptide

<400> SEQUENCE: 29

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Asp Ile Val Met Thr Gln Ser Pro Lys Phe Met Ser
    130                 135                 140

Thr Ser Val Gly Asp Arg Val Thr Val Thr Cys Lys Ala Ser Gln Asn
145                 150                 155                 160

Val Gly Thr Asn Val Ala Trp Phe Gln Gln Lys Pro Gly Gln Ser Pro
                165                 170                 175

Lys Val Leu Ile Tyr Ser Ala Ser Tyr Arg Tyr Ser Gly Val Pro Asp
            180                 185                 190

Arg Phe Thr Gly Ser Gly Ser Gly Thr Asp Phe Thr Leu Thr Ile Ser
        195                 200                 205

Asn Val Gln Ser Glu Asp Leu Ala Glu Tyr Phe Cys Gln Gln Tyr His
    210                 215                 220

Thr Tyr Pro Leu Thr Phe Gly Gly Gly Thr Lys Leu Glu Ile Asn Gly
225                 230                 235                 240

Gly Ser Gly Gly Ser Gly Gly Ser Gly Gly Ser Gly Gly Ser Gly Gly
                245                 250                 255

Ser Gly Gly Ser Gln Val Gln Leu Gln Gln Ser Gly Ala Glu Leu Ala
            260                 265                 270

Arg Pro Gly Ala Ser Val Lys Met Ser Cys Lys Ala Ser Gly Tyr Thr
        275                 280                 285

Phe Thr Thr Tyr Thr Ile His Trp Val Arg Gln Arg Pro Gly His Asp
    290                 295                 300

Leu Glu Trp Ile Gly Tyr Ile Asn Pro Ser Ser Gly Tyr Ser Asp Tyr
305                 310                 315                 320
```

-continued

```
Asn Gln Asn Phe Lys Gly Lys Thr Thr Leu Thr Ala Asp Lys Ser Ser
                325                 330                 335

Asn Thr Ala Tyr Met Gln Leu Asn Ser Leu Thr Ser Glu Asp Ser Ala
            340                 345                 350

Val Tyr Tyr Cys Ala Arg Arg Ala Asp Tyr Gly Asn Tyr Glu Tyr Thr
        355                 360                 365

Trp Phe Ala Tyr Trp Gly Gln Gly Thr Thr Val Thr Val Ser Ser Gly
    370                 375                 380

Gly Ser Gly Gly Ser Gly Gly Ser Asp Ile Val Met Thr Gln Ser Pro
385                 390                 395                 400

Lys Phe Met Ser Thr Ser Val Gly Asp Arg Val Thr Val Thr Cys Lys
                405                 410                 415

Ala Ser Gln Asn Val Gly Thr Asn Val Ala Trp Phe Gln Gln Lys Pro
            420                 425                 430

Gly Gln Ser Pro Lys Val Leu Ile Tyr Ser Ala Ser Tyr Arg Tyr Ser
        435                 440                 445

Gly Val Pro Asp Arg Phe Thr Gly Ser Gly Ser Gly Thr Asp Phe Thr
    450                 455                 460

Leu Thr Ile Ser Asn Val Gln Ser Glu Asp Leu Ala Glu Tyr Phe Cys
465                 470                 475                 480

Gln Gln Tyr His Thr Tyr Pro Leu Thr Phe Gly Gly Gly Thr Lys Leu
                485                 490                 495

Glu Ile Asn Gly Gly Gly Ser Gly Gly Ser Gln Val Gln Leu
            500                 505                 510

Val Gln Ser Gly Ala Glu Val Lys Lys Pro Gly Glu Ser Leu Lys Val
            515                 520                 525

Ser Cys Lys Ala Ser Gly Tyr Thr Phe Thr Ser Tyr Tyr Met His Trp
    530                 535                 540

Val Arg Gln Ala Pro Gly Gln Gly Leu Glu Trp Met Gly Ile Ile Asn
545                 550                 555                 560

Pro Ser Gly Gly Ser Thr Ser Tyr Ala Gln Lys Phe Gln Gly Arg Val
                565                 570                 575

Thr Met Thr Arg Asp Thr Ser Thr Ser Thr Val Tyr Met Glu Leu Ser
            580                 585                 590

Ser Leu Arg Ser Glu Asp Thr Ala Val Tyr Tyr Cys Ala Arg Gly Ser
        595                 600                 605

Ala Tyr Tyr Tyr Asp Phe Ala Asp Tyr Trp Gly Gln Gly Thr Leu Val
    610                 615                 620

Thr Val Ser Ser Gly Gly Gly Gly Ser Gly Gly Ser Gln Val Gln
625                 630                 635                 640

Leu Val Gln Ser Gly Ala Glu Val Lys Lys Pro Gly Glu Ser Leu Lys
                645                 650                 655

Val Ser Cys Lys Ala Ser Gly Tyr Thr Phe Thr Ser Tyr Tyr Met His
            660                 665                 670

Trp Val Arg Gln Ala Pro Gly Gln Gly Leu Glu Trp Met Gly Ile Ile
        675                 680                 685

Asn Pro Ser Gly Gly Ser Thr Ser Tyr Ala Gln Lys Phe Gln Gly Arg
    690                 695                 700

Val Thr Met Thr Arg Asp Thr Ser Thr Ser Thr Val Tyr Met Glu Leu
705                 710                 715                 720

Ser Ser Leu Arg Ser Glu Asp Thr Ala Val Tyr Tyr Cys Ala Arg Gly
                725                 730                 735
```

```
Ser Ala Tyr Tyr Tyr Asp Phe Ala Asp Tyr Trp Gly Gln Gly Thr Leu
            740                 745                 750

Val Thr Val Ser Ser Gly Gly Ser Gly Gly Ser Gly Gly Ser Gly Gly
            755                 760                 765

Ser Gly Gly Ser Gly Gly Ser Ser Tyr Val Leu Thr Gln Pro Ser Ser
            770                 775                 780

Val Ser Val Ala Pro Gly Gln Thr Ala Thr Ile Ser Cys Gly Gly His
785                 790                 795                 800

Asn Ile Gly Ser Lys Asn Val His Trp Tyr Gln Gln Arg Pro Gly Gln
                805                 810                 815

Ser Pro Val Leu Val Ile Tyr Gln Asp Asn Lys Arg Pro Ser Gly Ile
            820                 825                 830

Pro Glu Arg Phe Ser Gly Ser Asn Ser Gly Asn Thr Ala Thr Leu Thr
            835                 840                 845

Ile Ser Gly Thr Gln Ala Met Asp Glu Ala Asp Tyr Tyr Cys Gln Val
            850                 855                 860

Trp Asp Asn Tyr Ser Val Leu Phe Gly Gly Gly Thr Lys Leu Thr Val
865                 870                 875                 880

Leu Gly Gly Ser Gly Gly Ser Gly Gly Ser Ser Tyr Val Leu Thr Gln
                885                 890                 895

Pro Ser Ser Val Ser Val Ala Pro Gly Gln Thr Ala Thr Ile Ser Cys
            900                 905                 910

Gly Gly His Asn Ile Gly Ser Lys Asn Val His Trp Tyr Gln Gln Arg
            915                 920                 925

Pro Gly Gln Ser Pro Val Leu Val Ile Tyr Gln Asp Asn Lys Arg Pro
            930                 935                 940

Ser Gly Ile Pro Glu Arg Phe Ser Gly Ser Asn Ser Gly Asn Thr Ala
945                 950                 955                 960

Thr Leu Thr Ile Ser Gly Thr Gln Ala Met Asp Glu Ala Asp Tyr Tyr
                965                 970                 975

Cys Gln Val Trp Asp Asn Tyr Ser Val Leu Phe Gly Gly Gly Thr Lys
            980                 985                 990

Leu Thr Val Leu Gly Gly Ser Gly Gly Ser Gly Gly Ser Glu Val Gln
            995                 1000                1005

Leu Val Gln Ser Gly Ala Glu Val Lys Lys Pro Gly Glu Ser Leu
            1010                1015                1020

Lys Ile Ser Cys Lys Gly Ser Gly Tyr Ser Phe Thr Ser Asn Trp
            1025                1030                1035

Ile Gly Trp Val Arg Gln Met Pro Gly Lys Gly Leu Glu Trp Met
            1040                1045                1050

Gly Met Ile Trp Pro Gly Asp Ser Asp Thr Met Tyr Ser Pro Ser
            1055                1060                1065

Phe Gln Gly Gln Val Thr Ile Ser Ala Asp Glu Ser Ile Asn Thr
            1070                1075                1080

Ala Tyr Leu Gln Trp Ser Ser Leu Lys Ala Ser Asp Thr Ala Met
            1085                1090                1095

Tyr Tyr Cys Ala Arg Arg Glu Thr Thr Thr Val Gly Arg Tyr Tyr
            1100                1105                1110

Tyr Ala Met Asp Tyr Trp Gly Gln Gly Thr Leu Val Thr Val Ser
            1115                1120                1125

Ser Gly Gly Ser Gly Gly Ser Gly Gly Ser Ser Tyr Val Leu Thr
            1130                1135                1140

Gln Pro Pro Ser Val Ser Val Ala Pro Gly Gln Thr Ala Arg Ile
```

|     |     |     | 1145 |     |     |     | 1150 |     |     |     | 1155 |
| --- | --- | --- | --- | --- | --- | --- | --- | --- | --- | --- | --- |
| Thr | Cys | Gly | Gly | Asn | Asn | Ile | Gly | Ser | Lys | Thr | Val | His | Trp | Tyr |
|     |     |     | 1160 |     |     |     | 1165 |     |     |     | 1170 |

Gln Gln Lys Pro Gly Gln Ala Pro Val Leu Val Val Tyr Asp Asp
    1175            1180            1185

Ser Asp Arg Pro Ser Gly Ile Pro Glu Arg Phe Ser Gly Ser Asn
    1190            1195            1200

Ser Gly Asn Thr Ala Thr Leu Thr Ile Ser Arg Val Glu Ala Gly
    1205            1210            1215

Asp Glu Ala Asp Tyr Tyr Cys Gln Val Gly Thr Asp Trp Ser Asp
    1220            1225            1230

His Leu Gln Val Phe Gly Gly Gly Thr Lys Leu Thr Val Leu Gly
    1235            1240            1245

Gly Ser Gly Gly Ser Gly Gly Ser Gly Ser Gly Gly Ser Gly
    1250            1255            1260

Gly Ser Gly Gly Ser Glu Val Gln Leu Val Gln Ser Gly Ala Glu
    1265            1270            1275

Val Lys Lys Pro Gly Glu Ser Leu Lys Ile Ser Cys Lys Gly Ser
    1280            1285            1290

Gly Tyr Ser Phe Thr Ser Asn Trp Ile Gly Trp Val Arg Gln Met
    1295            1300            1305

Pro Gly Lys Gly Leu Glu Trp Met Gly Met Ile Trp Pro Gly Asp
    1310            1315            1320

Ser Asp Thr Met Tyr Ser Pro Ser Phe Gln Gly Gln Val Thr Ile
    1325            1330            1335

Ser Ala Asp Glu Ser Ile Asn Thr Ala Tyr Leu Gln Trp Ser Ser
    1340            1345            1350

Leu Lys Ala Ser Asp Thr Ala Met Tyr Tyr Cys Ala Arg Arg Glu
    1355            1360            1365

Thr Thr Thr Val Gly Arg Tyr Tyr Tyr Ala Met Asp Tyr Trp Gly
    1370            1375            1380

Gln Gly Thr Leu Val Thr Val Ser Ser Gly Gly Ser Gly Gly Ser
    1385            1390            1395

Gly Gly Ser Ser Tyr Val Leu Thr Gln Pro Pro Ser Val Ser Val
    1400            1405            1410

Ala Pro Gly Gln Thr Ala Arg Ile Thr Cys Gly Gly Asn Asn Ile
    1415            1420            1425

Gly Ser Lys Thr Val His Trp Tyr Gln Gln Lys Pro Gly Gln Ala
    1430            1435            1440

Pro Val Leu Val Val Tyr Asp Asp Ser Asp Arg Pro Ser Gly Ile
    1445            1450            1455

Pro Glu Arg Phe Ser Gly Ser Asn Ser Gly Asn Thr Ala Thr Leu
    1460            1465            1470

Thr Ile Ser Arg Val Glu Ala Gly Asp Glu Ala Asp Tyr Tyr Cys
    1475            1480            1485

Gln Val Gly Thr Asp Trp Ser Asp His Leu Gln Val Phe Gly Gly
    1490            1495            1500

Gly Thr Lys Leu Thr Val Leu Ala Ala Ala Gly Ser His His His
    1505            1510            1515

His His His
    1520

<210> SEQ ID NO 30

```
<211> LENGTH: 767
<212> TYPE: PRT
<213> ORGANISM: artificial
<220> FEATURE:
<223> OTHER INFORMATION: Fv polypeptide

<400> SEQUENCE: 30
```

| | | | | | | | | | | | | | | | |
|---|---|---|---|---|---|---|---|---|---|---|---|---|---|---|---|
| Gln | Val | Gln | Leu | Gln | Gln | Ser | Gly | Ala | Glu | Leu | Ala | Arg | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Thr | Tyr |
| | | | 20 | | | | | 25 | | | | | 30 | | |
| Thr | Ile | His | Trp | Val | Arg | Gln | Arg | Pro | Gly | His | Asp | Leu | Glu | Trp | Ile |
| | | 35 | | | | | 40 | | | | | 45 | | | |
| Gly | Tyr | Ile | Asn | Pro | Ser | Ser | Gly | Tyr | Ser | Asp | Tyr | Asn | Gln | Asn | Phe |
| 50 | | | | | 55 | | | | | 60 | | | | | |
| Lys | Gly | Lys | Thr | Thr | Leu | Thr | Ala | Asp | Lys | Ser | Ser | Asn | Thr | Ala | Tyr |
| 65 | | | | 70 | | | | | 75 | | | | | 80 | |
| Met | Gln | Leu | Asn | Ser | Leu | Thr | Ser | Glu | Asp | Ser | Ala | Val | Tyr | Tyr | Cys |
| | | | | 85 | | | | | 90 | | | | | 95 | |
| Ala | Arg | Arg | Ala | Asp | Tyr | Gly | Asn | Tyr | Glu | Tyr | Thr | Trp | Phe | Ala | Tyr |
| | | | 100 | | | | | 105 | | | | | 110 | | |
| Trp | Gly | Gln | Gly | Thr | Thr | Val | Thr | Val | Ser | Ser | Gly | Gly | Ser | Gly | Gly |
| | | 115 | | | | | 120 | | | | | 125 | | | |
| Ser | Gly | Gly | Ser | Gly | Gly | Ser | Gly | Gly | Ser | Gly | Gly | Ser | Gly | Gly | Ser |
| | | 130 | | | | | 135 | | | | | 140 | | | |
| Asp | Ile | Val | Met | Thr | Gln | Ser | Pro | Lys | Phe | Met | Ser | Thr | Ser | Val | Gly |
| 145 | | | | | 150 | | | | | 155 | | | | | 160 |
| Asp | Arg | Val | Thr | Val | Thr | Cys | Lys | Ala | Ser | Gln | Asn | Val | Gly | Thr | Asn |
| | | | | 165 | | | | | 170 | | | | | 175 | |
| Val | Ala | Trp | Phe | Gln | Gln | Lys | Pro | Gly | Gln | Ser | Pro | Lys | Val | Leu | Ile |
| | | | 180 | | | | | 185 | | | | | 190 | | |
| Tyr | Ser | Ala | Ser | Tyr | Arg | Tyr | Ser | Gly | Val | Pro | Asp | Arg | Phe | Thr | Gly |
| | | | 195 | | | | | 200 | | | | | 205 | | |
| Ser | Gly | Ser | Gly | Thr | Asp | Phe | Thr | Leu | Thr | Ile | Ser | Asn | Val | Gln | Ser |
| | | 210 | | | | | 215 | | | | | 220 | | | |
| Glu | Asp | Leu | Ala | Glu | Tyr | Phe | Cys | Gln | Gln | Tyr | His | Thr | Tyr | Pro | Leu |
| 225 | | | | | 230 | | | | | 235 | | | | | 240 |
| Thr | Phe | Gly | Gly | Gly | Thr | Lys | Leu | Glu | Ile | Asn | Gly | Gly | Ser | Gly | Gly |
| | | | | 245 | | | | | 250 | | | | | 255 | |
| Ser | Gly | Gly | Ser | Ser | Tyr | Val | Leu | Thr | Gln | Pro | Ser | Ser | Val | Ser | Val |
| | | | 260 | | | | | 265 | | | | | 270 | | |
| Ala | Pro | Gly | Gln | Thr | Ala | Thr | Ile | Ser | Cys | Gly | Gly | His | Asn | Ile | Gly |
| | | 275 | | | | | 280 | | | | | 285 | | | |
| Ser | Lys | Asn | Val | His | Trp | Tyr | Gln | Gln | Arg | Pro | Gly | Gln | Ser | Pro | Val |
| | 290 | | | | | 295 | | | | | 300 | | | | |
| Leu | Val | Ile | Tyr | Gln | Asp | Asn | Lys | Arg | Pro | Ser | Gly | Ile | Pro | Glu | Arg |
| 305 | | | | | 310 | | | | | 315 | | | | | 320 |
| Phe | Ser | Gly | Ser | Asn | Ser | Gly | Asn | Thr | Ala | Thr | Leu | Thr | Ile | Ser | Gly |
| | | | | 325 | | | | | 330 | | | | | 335 | |
| Thr | Gln | Ala | Met | Asp | Glu | Ala | Asp | Tyr | Tyr | Cys | Gln | Val | Trp | Asp | Asn |
| | | | 340 | | | | | 345 | | | | | 350 | | |
| Tyr | Ser | Val | Leu | Phe | Gly | Gly | Gly | Thr | Lys | Leu | Thr | Val | Leu | Gly | Gly |
| | | | 355 | | | | | 360 | | | | | 365 | | |
| Ser | Gly | Gly | Ser | Gly | Gly | Ser | Glu | Val | Gln | Leu | Val | Gln | Ser | Gly | Ala |
| | | 370 | | | | | 375 | | | | | 380 | | | |

Glu Val Lys Lys Pro Gly Glu Ser Leu Lys Ile Ser Cys Lys Gly Ser
385                 390                 395                 400

Gly Tyr Ser Phe Thr Ser Tyr Trp Ile Gly Trp Val Arg Gln Met Pro
            405                 410                 415

Gly Lys Gly Leu Glu Trp Met Gly Ile Ile Tyr Pro Gly Asp Ser Asp
            420                 425                 430

Thr Arg Tyr Ser Pro Ser Phe Gln Gly Gln Val Thr Ile Ser Ala Asp
            435                 440                 445

Lys Ser Ile Ser Thr Ala Tyr Leu Gln Trp Ser Ser Leu Lys Ala Ser
            450                 455                 460

Asp Thr Ala Met Tyr Tyr Cys Ala Arg Leu Gly Ser Ser Trp Thr Asn
465                 470                 475                 480

Asp Ala Phe Asp Ile Trp Gly Gln Gly Thr Met Val Thr Val Ser Ser
            485                 490                 495

Gly Gly Ser Gly Gly Ser Gly Gly Ser Gln Val Gln Leu Gln Gln Ser
            500                 505                 510

Gly Ala Glu Leu Ala Arg Pro Gly Ala Ser Val Lys Met Ser Cys Lys
            515                 520                 525

Ala Ser Gly Tyr Thr Phe Thr Thr Tyr Thr Ile His Trp Val Arg Gln
530                 535                 540

Arg Pro Gly His Asp Leu Glu Trp Ile Gly Tyr Ile Asn Pro Ser Ser
545                 550                 555                 560

Gly Tyr Ser Asp Tyr Asn Gln Asn Phe Lys Gly Lys Thr Thr Leu Thr
            565                 570                 575

Ala Asp Lys Ser Ser Asn Thr Ala Tyr Met Gln Leu Asn Ser Leu Thr
            580                 585                 590

Ser Glu Asp Ser Ala Val Tyr Tyr Cys Ala Arg Arg Ala Asp Tyr Gly
            595                 600                 605

Asn Tyr Glu Tyr Thr Trp Phe Ala Tyr Trp Gly Gln Gly Thr Thr Val
            610                 615                 620

Thr Val Ser Ser Gly Gly Ser Gly Gly Ser Gly Gly Ser Gly Gly Ser
625                 630                 635                 640

Gly Gly Ser Gly Gly Ser Gly Gly Ser Asp Ile Val Met Thr Gln Ser
            645                 650                 655

Pro Lys Phe Met Ser Thr Ser Val Gly Asp Arg Val Thr Val Thr Cys
            660                 665                 670

Lys Ala Ser Gln Asn Val Gly Thr Asn Val Ala Trp Phe Gln Gln Lys
            675                 680                 685

Pro Gly Gln Ser Pro Lys Val Leu Ile Tyr Ser Ala Ser Tyr Arg Tyr
            690                 695                 700

Ser Gly Val Pro Asp Arg Phe Thr Gly Ser Gly Ser Gly Thr Asp Phe
705                 710                 715                 720

Thr Leu Thr Ile Ser Asn Val Gln Ser Glu Asp Leu Ala Glu Tyr Phe
            725                 730                 735

Cys Gln Gln Tyr His Thr Tyr Pro Leu Thr Phe Gly Gly Gly Thr Lys
            740                 745                 750

Leu Glu Ile Asn Ala Ala Ala Gly Ser His His His His His
            755                 760                 765

<210> SEQ ID NO 31
<211> LENGTH: 251
<212> TYPE: PRT
<213> ORGANISM: artificial
<220> FEATURE:

<223> OTHER INFORMATION: Fv polypeptide

<400> SEQUENCE: 31

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Pro
                85                  90                  95

Leu Ile Val Phe Gly Thr Gly Thr Lys Leu Thr Val Leu Gly Gly Ser
            100                 105                 110

Gly Gly Ser Gly Gly Ser Gln Val Gln Leu Val Gln Ser Gly Ala Glu
        115                 120                 125

Val Lys Lys Pro Gly Glu Ser Leu Lys Val Ser Cys Lys Ala Ser Gly
    130                 135                 140

Tyr Thr Phe Thr Ser Tyr Tyr Met His Trp Val Arg Gln Ala Pro Gly
145                 150                 155                 160

Gln Gly Leu Glu Trp Met Gly Ile Ile Asn Pro Ser Gly Gly Ser Thr
                165                 170                 175

Ser Tyr Ala Gln Lys Phe Gln Gly Arg Val Thr Met Thr Arg Asp Thr
            180                 185                 190

Ser Thr Ser Thr Val Tyr Met Glu Leu Ser Ser Leu Arg Ser Glu Asp
        195                 200                 205

Thr Ala Val Tyr Tyr Cys Ala Arg Gly Ser Ala Tyr Tyr Tyr Asp Phe
    210                 215                 220

Ala Asp Tyr Trp Gly Gln Gly Thr Leu Val Thr Val Ser Ser Ala Ala
225                 230                 235                 240

Ala Gly Ser Asp Tyr Lys Asp Asp Asp Lys
                245                 250
```

<210> SEQ ID NO 32
<211> LENGTH: 769
<212> TYPE: PRT
<213> ORGANISM: artificial
<220> FEATURE:
<223> OTHER INFORMATION: Fv polypeptide

<400> SEQUENCE: 32

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95
```

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Ser Gly Gly
            115                 120                 125

Ser Gly Gly Ser Gly Gly Ser Gly Gly Ser Gly Gly Ser
    130                 135                 140

Asp Ile Val Met Thr Gln Ser Pro Lys Phe Met Ser Thr Ser Val Gly
145                 150                 155                 160

Asp Arg Val Thr Val Thr Cys Lys Ala Ser Gln Asn Val Gly Thr Asn
                165                 170                 175

Val Ala Trp Phe Gln Gln Lys Pro Gly Gln Ser Pro Lys Val Leu Ile
            180                 185                 190

Tyr Ser Ala Ser Tyr Arg Tyr Ser Gly Val Pro Asp Arg Phe Thr Gly
            195                 200                 205

Ser Gly Ser Gly Thr Asp Phe Thr Leu Thr Ile Ser Asn Val Gln Ser
    210                 215                 220

Glu Asp Leu Ala Glu Tyr Phe Cys Gln Gln Tyr His Thr Tyr Pro Leu
225                 230                 235                 240

Thr Phe Gly Gly Gly Thr Lys Leu Glu Ile Asn Gly Gly Ser Gly Gly
            245                 250                 255

Ser Gly Gly Ser Gln Val Gln Leu Val Gln Ser Gly Ala Glu Val Lys
    260                 265                 270

Lys Pro Gly Glu Ser Leu Lys Val Ser Cys Lys Ala Ser Gly Tyr Thr
            275                 280                 285

Phe Thr Ser Tyr Tyr Met His Trp Val Arg Gln Ala Pro Gly Gln Gly
            290                 295                 300

Leu Glu Trp Met Gly Ile Ile Asn Pro Ser Gly Gly Ser Thr Ser Tyr
305                 310                 315                 320

Ala Gln Lys Phe Gln Gly Arg Val Thr Met Thr Arg Asp Thr Ser Thr
            325                 330                 335

Ser Thr Val Tyr Met Glu Leu Ser Ser Leu Arg Ser Glu Asp Thr Ala
            340                 345                 350

Val Tyr Tyr Cys Ala Arg Gly Ser Ala Tyr Tyr Asp Phe Ala Asp
            355                 360                 365

Tyr Trp Gly Gln Gly Thr Leu Val Thr Val Ser Ser Gly Gly Ser Gly
    370                 375                 380

Gly Ser Gly Gly Ser Ser Tyr Glu Leu Thr Gln Pro Pro Ser Val Ser
385                 390                 395                 400

Val Ser Pro Gly Gln Thr Ala Arg Ile Thr Cys Ser Gly Asp Ala Leu
            405                 410                 415

Pro Lys Gln Tyr Ala Tyr Trp Tyr Gln Gln Lys Pro Gly Gln Ala Pro
            420                 425                 430

Val Leu Val Ile Tyr Lys Asp Ser Glu Arg Pro Ser Gly Ile Pro Glu
            435                 440                 445

Arg Phe Ser Gly Ser Ser Ser Gly Thr Thr Val Thr Leu Thr Ile Ser
            450                 455                 460

Gly Val Gln Ala Glu Asp Glu Ala Asp Tyr Tyr Cys Gln Ser Ala Asp
465                 470                 475                 480

Ser Ser Gly Thr Pro Leu Ile Val Phe Gly Thr Gly Thr Lys Leu Thr
                485                 490                 495

Val Leu Gly Gly Ser Gly Gly Ser Gly Gly Ser Gln Val Gln Leu Gln
            500                 505                 510

```
Gln Ser Gly Ala Glu Leu Ala Arg Pro Gly Ala Ser Val Lys Met Ser
            515                 520                 525

Cys Lys Ala Ser Gly Tyr Thr Phe Thr Thr Tyr Thr Ile His Trp Val
    530                 535                 540

Arg Gln Arg Pro Gly His Asp Leu Glu Trp Ile Gly Tyr Ile Asn Pro
545                 550                 555                 560

Ser Ser Gly Tyr Ser Asp Tyr Asn Gln Asn Phe Lys Gly Lys Thr Thr
                565                 570                 575

Leu Thr Ala Asp Lys Ser Ser Asn Thr Ala Tyr Met Gln Leu Asn Ser
            580                 585                 590

Leu Thr Ser Glu Asp Ser Ala Val Tyr Tyr Cys Ala Arg Arg Ala Asp
        595                 600                 605

Tyr Gly Asn Tyr Glu Tyr Thr Trp Phe Ala Tyr Trp Gly Gln Gly Thr
    610                 615                 620

Thr Val Thr Val Ser Ser Gly Gly Ser Gly Gly Ser Gly Gly Ser Gly
625                 630                 635                 640

Gly Ser Gly Gly Ser Gly Gly Ser Gly Gly Ser Asp Ile Val Met Thr
                645                 650                 655

Gln Ser Pro Lys Phe Met Ser Thr Ser Val Gly Asp Arg Val Thr Val
            660                 665                 670

Thr Cys Lys Ala Ser Gln Asn Val Gly Thr Asn Val Ala Trp Phe Gln
        675                 680                 685

Gln Lys Pro Gly Gln Ser Pro Lys Val Leu Ile Tyr Ser Ala Ser Tyr
    690                 695                 700

Arg Tyr Ser Gly Val Pro Asp Arg Phe Thr Gly Ser Gly Ser Gly Thr
705                 710                 715                 720

Asp Phe Thr Leu Thr Ile Ser Asn Val Gln Ser Glu Asp Leu Ala Glu
                725                 730                 735

Tyr Phe Cys Gln Gln Tyr His Thr Tyr Pro Leu Thr Phe Gly Gly Gly
            740                 745                 750

Thr Lys Leu Glu Ile Asn Ala Ala Ala Gly Ser His His His His His
        755                 760                 765

His

<210> SEQ ID NO 33
<211> LENGTH: 249
<212> TYPE: PRT
<213> ORGANISM: artificial
<220> FEATURE:
<223> OTHER INFORMATION: Fv polypeptide

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
```

```
                    100                 105                 110
Gln Gly Thr Met Val Thr Val Ser Gly Gly Ser Gly Gly Ser Gly
            115                 120                 125
Gly Ser Ser Tyr Val Leu Thr Gln Pro Ser Ser Val Ser Val Ala Pro
130                 135                 140
Gly Gln Thr Ala Thr Ile Ser Cys Gly Gly His Asn Ile Gly Ser Lys
145                 150                 155                 160
Asn Val His Trp Tyr Gln Gln Arg Pro Gly Gln Ser Pro Val Leu Val
            165                 170                 175
Ile Tyr Gln Asp Asn Lys Arg Pro Ser Gly Ile Pro Glu Arg Phe Ser
            180                 185                 190
Gly Ser Asn Ser Gly Asn Thr Ala Thr Leu Thr Ile Ser Gly Thr Gln
            195                 200                 205
Ala Met Asp Glu Ala Asp Tyr Tyr Cys Gln Val Trp Asp Asn Tyr Ser
            210                 215                 220
Val Leu Phe Gly Gly Gly Thr Lys Leu Thr Val Leu Ala Ala Ala Gly
225                 230                 235                 240
Ser Asp Tyr Lys Asp Asp Asp Lys
            245

<210> SEQ ID NO 34
<211> LENGTH: 781
<212> TYPE: PRT
<213> ORGANISM: artificial
<220> FEATURE:
<223> OTHER INFORMATION: Fv polypeptide

<400> SEQUENCE: 34

Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Thr Tyr
            20                  25                  30
Thr Ile His Trp Val Arg Gln Arg Pro Gly His Asp Leu Glu Trp Ile
        35                  40                  45
Gly Tyr Ile Asn Pro Ser Ser Gly Tyr Ser Asp Tyr Asn Gln Asn Phe
50                  55                  60
Lys Gly Lys Thr Thr Leu Thr Ala Asp Lys Ser Ser Asn Thr Ala Tyr
65                  70                  75                  80
Met Gln Leu Asn Ser Leu Thr Ser Glu Asp Ser Ala Val Tyr Tyr Cys
                85                  90                  95
Ala Arg Arg Ala Asp Tyr Gly Asn Tyr Glu Tyr Thr Trp Phe Ala Tyr
            100                 105                 110
Trp Gly Gln Gly Thr Thr Val Thr Val Ser Ser Gly Gly Ser Gly Gly
            115                 120                 125
Ser Gly Gly Ser Gly Gly Ser Gly Gly Ser Gly Gly Ser Gly Gly Ser
130                 135                 140
Asp Ile Val Met Thr Gln Ser Pro Lys Phe Met Ser Thr Ser Val Gly
145                 150                 155                 160
Asp Arg Val Thr Val Thr Cys Lys Ala Ser Gln Asn Val Gly Thr Asn
            165                 170                 175
Val Ala Trp Phe Gln Gln Lys Pro Gly Gln Ser Pro Lys Val Leu Ile
            180                 185                 190
Tyr Ser Ala Ser Tyr Arg Tyr Ser Gly Val Pro Asp Arg Phe Thr Gly
            195                 200                 205
Ser Gly Ser Gly Thr Asp Phe Thr Leu Thr Ile Ser Asn Val Gln Ser
```

```
            210                 215                 220
Glu Asp Leu Ala Glu Tyr Phe Cys Gln Gln Tyr His Thr Tyr Pro Leu
225                 230                 235                 240

Thr Phe Gly Gly Gly Thr Lys Leu Glu Ile Asn Gly Gly Ser Gly Gly
                245                 250                 255

Ser Gly Gly Ser Gln Val Gln Leu Val Gln Ser Gly Ala Glu Val Lys
                260                 265                 270

Lys Pro Gly Glu Ser Leu Lys Val Ser Cys Lys Ala Ser Gly Tyr Thr
                275                 280                 285

Phe Thr Ser Tyr Tyr Met His Trp Val Arg Gln Ala Pro Gly Gln Gly
                290                 295                 300

Leu Glu Trp Met Gly Ile Ile Asn Pro Ser Gly Gly Ser Thr Ser Tyr
305                 310                 315                 320

Ala Gln Lys Phe Gln Gly Arg Val Thr Met Thr Arg Asp Thr Ser Thr
                325                 330                 335

Ser Thr Val Tyr Met Glu Leu Ser Ser Leu Arg Ser Glu Asp Thr Ala
                340                 345                 350

Val Tyr Tyr Cys Ala Arg Gly Ser Ala Tyr Tyr Asp Phe Ala Asp
                355                 360                 365

Tyr Trp Gly Gln Gly Thr Leu Val Thr Val Ser Ser Gly Gly Ser Gly
                370                 375                 380

Gly Ser Gly Gly Ser Glu Val Gln Leu Val Gln Ser Gly Ala Glu Val
385                 390                 395                 400

Lys Lys Pro Gly Glu Ser Leu Lys Ile Ser Cys Lys Gly Ser Gly Tyr
                405                 410                 415

Ser Phe Thr Ser Tyr Trp Ile Gly Trp Val Arg Gln Met Pro Gly Lys
                420                 425                 430

Gly Leu Glu Trp Met Gly Ile Ile Tyr Pro Gly Asp Ser Asp Thr Arg
                435                 440                 445

Tyr Ser Pro Ser Phe Gln Gly Gln Val Thr Ile Ser Ala Asp Lys Ser
450                 455                 460

Ile Ser Thr Ala Tyr Leu Gln Trp Ser Ser Leu Lys Ala Ser Asp Thr
465                 470                 475                 480

Ala Met Tyr Tyr Cys Ala Arg Leu Gly Ser Ser Trp Thr Asn Asp Ala
                485                 490                 495

Phe Asp Ile Trp Gly Gln Gly Thr Met Val Thr Val Ser Ser Gly Gly
                500                 505                 510

Ser Gly Gly Ser Gly Gly Ser Gln Val Gln Leu Gln Gln Ser Gly Ala
                515                 520                 525

Glu Leu Ala Arg Pro Gly Ala Ser Val Lys Met Ser Cys Lys Ala Ser
                530                 535                 540

Gly Tyr Thr Phe Thr Thr Tyr Thr Ile His Trp Val Arg Gln Arg Pro
545                 550                 555                 560

Gly His Asp Leu Glu Trp Ile Gly Tyr Ile Asn Pro Ser Ser Gly Tyr
                565                 570                 575

Ser Asp Tyr Asn Gln Asn Phe Lys Gly Lys Thr Thr Leu Thr Ala Asp
                580                 585                 590

Lys Ser Ser Asn Thr Ala Tyr Met Gln Leu Asn Ser Leu Thr Ser Glu
                595                 600                 605

Asp Ser Ala Val Tyr Tyr Cys Ala Arg Arg Ala Asp Tyr Gly Asn Tyr
                610                 615                 620

Glu Tyr Thr Trp Phe Ala Tyr Trp Gly Gln Gly Thr Thr Val Thr Val
625                 630                 635                 640
```

```
Ser Ser Gly Gly Ser Gly Gly Ser Gly Gly Ser Gly Gly
            645                 650                 655

Ser Gly Gly Ser Gly Gly Ser Asp Ile Val Met Thr Gln Ser Pro Lys
            660                 665                 670

Phe Met Ser Thr Ser Val Gly Asp Arg Val Thr Val Thr Cys Lys Ala
            675                 680                 685

Ser Gln Asn Val Gly Thr Asn Val Ala Trp Phe Gln Gln Lys Pro Gly
            690                 695                 700

Gln Ser Pro Lys Val Leu Ile Tyr Ser Ala Ser Tyr Arg Tyr Ser Gly
705                 710                 715                 720

Val Pro Asp Arg Phe Thr Gly Ser Gly Ser Gly Thr Asp Phe Thr Leu
                    725                 730                 735

Thr Ile Ser Asn Val Gln Ser Glu Asp Leu Ala Glu Tyr Phe Cys Gln
                    740                 745                 750

Gln Tyr His Thr Tyr Pro Leu Thr Phe Gly Gly Gly Thr Lys Leu Glu
                    755                 760                 765

Ile Asn Ala Ala Ala Gly Ser His His His His His
            770                 775                 780

<210> SEQ ID NO 35
<211> LENGTH: 237
<212> TYPE: PRT
<213> ORGANISM: artificial
<220> FEATURE:
<223> OTHER INFORMATION: Fv polypeptide

<400> SEQUENCE: 35

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Pro
                85                  90                  95

Leu Ile Val Phe Gly Thr Gly Thr Lys Leu Thr Val Leu Gly Gly Ser
            100                 105                 110

Gly Gly Ser Gly Gly Ser Ser Tyr Val Leu Thr Gln Pro Ser Ser Val
            115                 120                 125

Ser Val Ala Pro Gly Gln Thr Ala Thr Ile Ser Cys Gly Gly His Asn
        130                 135                 140

Ile Gly Ser Lys Asn Val His Trp Tyr Gln Gln Arg Pro Gly Gln Ser
145                 150                 155                 160

Pro Val Leu Val Ile Tyr Gln Asp Asn Lys Arg Pro Ser Gly Ile Pro
                165                 170                 175

Glu Arg Phe Ser Gly Ser Asn Ser Gly Asn Thr Ala Thr Leu Thr Ile
            180                 185                 190

Ser Gly Thr Gln Ala Met Asp Glu Ala Asp Tyr Tyr Cys Gln Val Trp
        195                 200                 205

Asp Asn Tyr Ser Val Leu Phe Gly Gly Gly Thr Lys Leu Thr Val Leu
    210                 215                 220
```

Ala Ala Ala Gly Ser Asp Tyr Lys Asp Asp Asp Lys
225                 230                 235

<210> SEQ ID NO 36
<211> LENGTH: 755
<212> TYPE: PRT
<213> ORGANISM: artificial
<220> FEATURE:
<223> OTHER INFORMATION: Fv polypeptide

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser Gly Gly Ser Gly Gly
        115                 120                 125

Ser Gly Gly Ser Gly Gly Ser Gly Gly Ser Gly Gly Ser Gly Gly Ser
    130                 135                 140

Asp Ile Val Met Thr Gln Ser Pro Lys Phe Met Ser Thr Ser Val Gly
145                 150                 155                 160

Asp Arg Val Thr Val Thr Cys Lys Ala Ser Gln Asn Val Gly Thr Asn
                165                 170                 175

Val Ala Trp Phe Gln Gln Lys Pro Gly Gln Ser Pro Lys Val Leu Ile
            180                 185                 190

Tyr Ser Ala Ser Tyr Arg Tyr Ser Gly Val Pro Asp Arg Phe Thr Gly
        195                 200                 205

Ser Gly Ser Gly Thr Asp Phe Thr Leu Thr Ile Ser Asn Val Gln Ser
    210                 215                 220

Glu Asp Leu Ala Glu Tyr Phe Cys Gln Gln Tyr His Thr Tyr Pro Leu
225                 230                 235                 240

Thr Phe Gly Gly Gly Thr Lys Leu Glu Ile Asn Gly Gly Ser Gly Gly
                245                 250                 255

Ser Gly Gly Ser Ser Tyr Val Leu Thr Gln Pro Ser Ser Val Ser Val
            260                 265                 270

Ala Pro Gly Gln Thr Ala Thr Ile Ser Cys Gly Gly His Asn Ile Gly
        275                 280                 285

Ser Lys Asn Val His Trp Tyr Gln Gln Arg Pro Gly Gln Ser Pro Val
    290                 295                 300

Leu Val Ile Tyr Gln Asp Asn Lys Arg Pro Ser Gly Ile Pro Glu Arg
305                 310                 315                 320

Phe Ser Gly Ser Asn Ser Gly Asn Thr Ala Thr Leu Thr Ile Ser Gly
                325                 330                 335

Thr Gln Ala Met Asp Glu Ala Asp Tyr Tyr Cys Gln Val Trp Asp Asn
            340                 345                 350

```
Tyr Ser Val Leu Phe Gly Gly Gly Thr Lys Leu Thr Val Leu Gly Gly
            355                 360                 365

Ser Gly Gly Ser Gly Gly Ser Ser Tyr Glu Leu Thr Gln Pro Pro Ser
    370                 375                 380

Val Ser Val Ser Pro Gly Gln Thr Ala Arg Ile Thr Cys Ser Gly Asp
385                 390                 395                 400

Ala Leu Pro Lys Gln Tyr Ala Tyr Trp Tyr Gln Gln Lys Pro Gly Gln
                405                 410                 415

Ala Pro Val Leu Val Ile Tyr Lys Asp Ser Glu Arg Pro Ser Gly Ile
                420                 425                 430

Pro Glu Arg Phe Ser Gly Ser Ser Ser Gly Thr Thr Val Thr Leu Thr
            435                 440                 445

Ile Ser Gly Val Gln Ala Glu Asp Glu Ala Asp Tyr Tyr Cys Gln Ser
        450                 455                 460

Ala Asp Ser Ser Gly Thr Pro Leu Ile Val Phe Gly Thr Gly Thr Lys
465                 470                 475                 480

Leu Thr Val Leu Gly Gly Ser Gly Gly Ser Gly Gly Ser Gln Val Gln
                485                 490                 495

Leu Gln Gln Ser Gly Ala Glu Leu Ala Arg Pro Gly Ala Ser Val Lys
            500                 505                 510

Met Ser Cys Lys Ala Ser Gly Tyr Thr Phe Thr Tyr Thr Ile His
        515                 520                 525

Trp Val Arg Gln Arg Pro Gly His Asp Leu Glu Trp Ile Gly Tyr Ile
    530                 535                 540

Asn Pro Ser Ser Gly Tyr Ser Asp Tyr Asn Gln Asn Phe Lys Gly Lys
545                 550                 555                 560

Thr Thr Leu Thr Ala Asp Lys Ser Ser Asn Thr Ala Tyr Met Gln Leu
                565                 570                 575

Asn Ser Leu Thr Ser Glu Asp Ser Ala Val Tyr Tyr Cys Ala Arg Arg
            580                 585                 590

Ala Asp Tyr Gly Asn Tyr Glu Tyr Thr Trp Phe Ala Tyr Trp Gly Gln
        595                 600                 605

Gly Thr Thr Val Thr Val Ser Ser Gly Gly Ser Gly Gly Ser Gly Gly
    610                 615                 620

Ser Gly Gly Ser Gly Gly Ser Gly Gly Ser Gly Gly Ser Asp Ile Val
625                 630                 635                 640

Met Thr Gln Ser Pro Lys Phe Met Ser Thr Ser Val Gly Asp Arg Val
                645                 650                 655

Thr Val Thr Cys Lys Ala Ser Gln Asn Val Gly Thr Asn Val Ala Trp
            660                 665                 670

Phe Gln Gln Lys Pro Gly Gln Ser Pro Lys Val Leu Ile Tyr Ser Ala
        675                 680                 685

Ser Tyr Arg Tyr Ser Gly Val Pro Asp Arg Phe Thr Gly Ser Gly Ser
    690                 695                 700

Gly Thr Asp Phe Thr Leu Thr Ile Ser Asn Val Gln Ser Glu Asp Leu
705                 710                 715                 720

Ala Glu Tyr Phe Cys Gln Gln Tyr His Thr Tyr Pro Leu Thr Phe Gly
                725                 730                 735

Gly Gly Thr Lys Leu Glu Ile Asn Ala Ala Ala Gly Ser His His His
            740                 745                 750

His His His
    755
```

```
<210> SEQ ID NO 37
<211> LENGTH: 263
<212> TYPE: PRT
<213> ORGANISM: artificial
<220> FEATURE:
<223> OTHER INFORMATION: Fv polypeptide

<400> SEQUENCE: 37

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Met Val Thr Val Ser Ser Gly Ser Gly Gly Ser Gly
        115                 120                 125

Gly Ser Gln Val Gln Leu Val Gln Ser Gly Ala Glu Val Lys Lys Pro
    130                 135                 140

Gly Glu Ser Leu Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Gly Ser Ala Tyr Tyr Tyr Asp Phe Ala Asp Tyr Trp
225                 230                 235                 240

Gly Gln Gly Thr Leu Val Thr Val Ser Ser Ala Ala Ala Gly Ser Asp
                245                 250                 255

Tyr Lys Asp Asp Asp Asp Lys
            260

<210> SEQ ID NO 38
<211> LENGTH: 8
<212> TYPE: PRT
<213> ORGANISM: artificial
<220> FEATURE:
<223> OTHER INFORMATION: FLAG tag

<400> SEQUENCE: 38

Asp Tyr Lys Asp Asp Asp Asp Lys
1               5

<210> SEQ ID NO 39
<211> LENGTH: 8
<212> TYPE: PRT
<213> ORGANISM: artificial
```

```
<220> FEATURE:
<223> OTHER INFORMATION: STREP II Tag

<400> SEQUENCE: 39

Trp Ser His Pro Gln Phe Glu Lys
1               5

<210> SEQ ID NO 40
<211> LENGTH: 4
<212> TYPE: PRT
<213> ORGANISM: artificial
<220> FEATURE:
<223> OTHER INFORMATION: C Tag

<400> SEQUENCE: 40

Glu Pro Glu Ala
1
```